(12) United States Patent
Rana et al.

(10) Patent No.: US 7,754,773 B2
(45) Date of Patent: Jul. 13, 2010

(54) COMPOSITION AND SYNTHESIS OF NEW REAGENTS FOR INHIBITION OF HIV REPLICATION

(75) Inventors: Tariq M. Rana, San Diego, CA (US); Mario Stevenson, Worcester, MA (US); Robin Scott Nathans, Norfolk, MA (US); Hong Cao, Westborough, MA (US); Akbar Ali, Worcester, MA (US)

(73) Assignee: University of Massachusetts, Boston, MA (US)

( * ) Notice: Subject to any disclaimer, the term of this patent is extended or adjusted under 35 U.S.C. 154(b) by 326 days.

(21) Appl. No.: 11/544,068

(22) Filed: Oct. 6, 2006

(65) Prior Publication Data

US 2007/0099919 A1    May 3, 2007

Related U.S. Application Data

(60) Provisional application No. 60/725,043, filed on Oct. 6, 2005.

(51) Int. Cl.
*A61K 31/075*    (2006.01)
(52) U.S. Cl. .................................................. 514/721
(58) Field of Classification Search .................. None
See application file for complete search history.

(56) References Cited

U.S. PATENT DOCUMENTS

2005/0123906 A1    6/2005    Rana

FOREIGN PATENT DOCUMENTS

| WO | WO 0006146 | * | 2/2000 |
| WO | WO 0046203 | * | 8/2000 |

OTHER PUBLICATIONS

Gu et al., "A Powerful Arm of the Cellular Defence Against Microbial Invaders has been Characterized. APOBEC3G, a Protein that can Fight off HIV, Works by Introducing 'Typographical Errors' During Viral Replication", Nature 424-21-22, Jul. 3, 2003.
Wichroski et al, "Analysis of HIV—Viral Infectivity Factor-mediated Proteasome-dependent Depletion of APOBEC3G", The Journal of Biological Chemistry 280:8387-8396, 2005.
Cho et al., "APOBEC3F and APOBEC3G mRNA Levels Do Not Correlate with Human Immunodeficiency Virus Type 1 Plasma Viremia or CD4+ T-Cell Count," J. Virol., 80:2069-72 (2006).
Fouchier et al., "Human immunodeficiency virus type 1 Vif does not influence expression or virion incorporation of *gag-*, *pol-*, and *env-* encoded proteins," J. Virol., 70:8263-69 (1996).
Madani and Kabat, "Cellular and Viral Specificities of Human Immunodeficiency Virus Type 1 Vif Protein," J. Virol., 74:5982-87 (2000).
Sharova et al., "Primate lentiviral Vpx commandeers DDB1 to counteract a macrophage restriction," PLoS Pathog., 4:e1000057 (2008).
Simon et al., "Complementation of *vif*-defective human immunodeficiency virus type 1 by primate, but not nonprimate, lentivirus *vif* genes," J. Virol., 69:4166-72 (1995).
Simon et al., "Mutational Analysis of the Human Immunodeficiency Virus Type 1 Vif Protein," J. Virol., 73:2675-81 (1999).
Simon et al., "The Vif and Gag proteins of human immunodeficiency virus type 1 colocalize in infected human T cells," J. Virol., 71:5259-67 (1997).
Wichroski et al., "Analysis of HIV-1 viral infectivity factor-mediated proteasome-dependent depletion of APOBEC3G: correlating function and subcellular localization," J. Biol. Chem., 280:8387-96 (2005).
Wichroski et al., "Human retroviral host restriction factors APOBEC3G and APOBEC3F localize to mRNA processing bodies," PLoS Pathog., 2:e41 (2006).

* cited by examiner

*Primary Examiner*—James O Wilson
*Assistant Examiner*—Noble Jarrell
(74) *Attorney, Agent, or Firm*—Fish & Richardson P.C.

(57) ABSTRACT

The present invention provides compounds and compositions for inhibiting Vif and methods for treating viral infection, e.g., HIV infection.

17 Claims, 62 Drawing Sheets

| No | Structure |
|----|-----------|
| 1. | 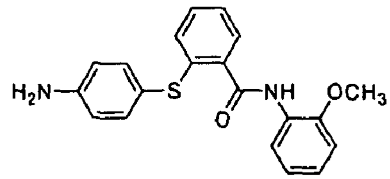 |
| 2. | 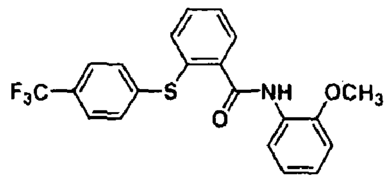 |
| 3. | 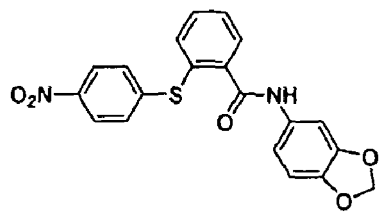 |
| 4. | 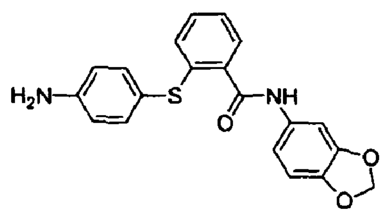 |
| 5. | 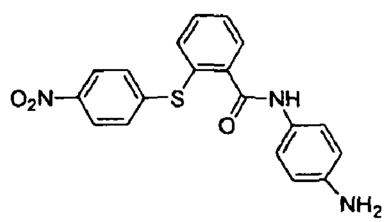 |
| 6. | 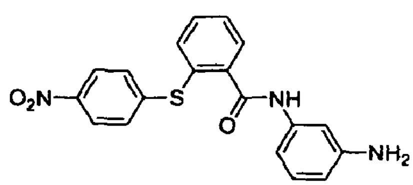 |
| 7. | 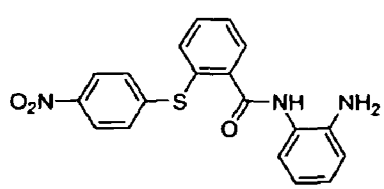 |

| No | Structure | CAS Number |
|---|---|---|
| 1. | 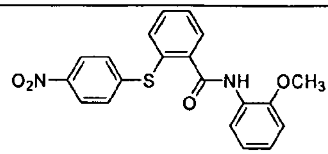 | 431980-38-0 |
| 2. | 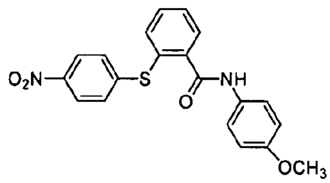 | 431935-07-8 |
| 3. | 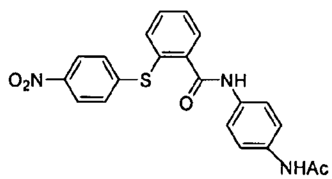 | 431999-29-0 |
| 4. | 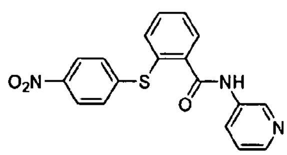 | 805944-15-4 |
| 5. | 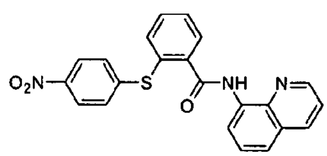 | 431998-85-5 |
| 6. | 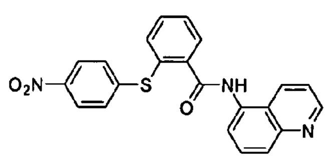 | 432014-80-7 |
| 7. | 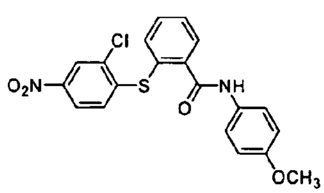 | 694448-06-1 |

8.  694444-55-8

9.  693829-97-9

10.  701258-34-6

11.  404846-79-3

12.  331653-81-7

Vif Inhibitor 1

| Class | Structure | X | Y | R1 |
|---|---|---|---|---|
| A | 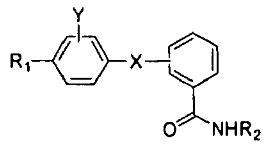 | S, O, NH, CH₂, – | F, Cl | NO₂, NH₂, NHAc, CN, CO₂R |
| B | 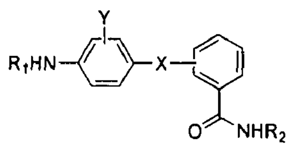 | S, O, NH, CH₂, – | F, Cl | R–C(O)–Cl |
| C | 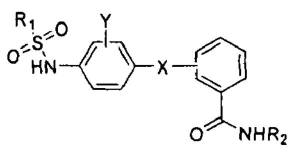 | S, O, NH, CH₂, – | F, Cl | R–S(O)₂–Cl |
| D | 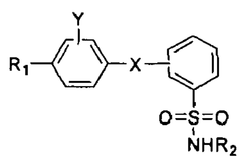 | S, O, NH, CH₂, – | F, Cl | NO₂, NH₂, NHAc, CN, CO₂R |
| E | 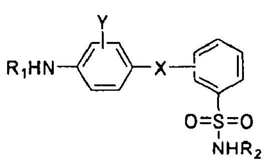 | S, O, NH, CH₂, – | F, Cl | R–C(O)–Cl |
| F | 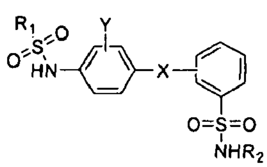 | S, O, NH, CH₂, – | F, Cl | R–S(O)₂–Cl |
| G | 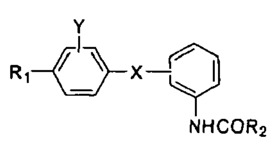 | S, O, NH, CH₂, – | F, Cl | NO₂, NH₂, NHAc, CN, CO₂R |
| H | 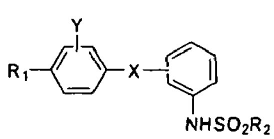 | S, O, NH, CH₂, – | F, Cl | NO₂, NH₂, NHAc, CN, CO₂R |

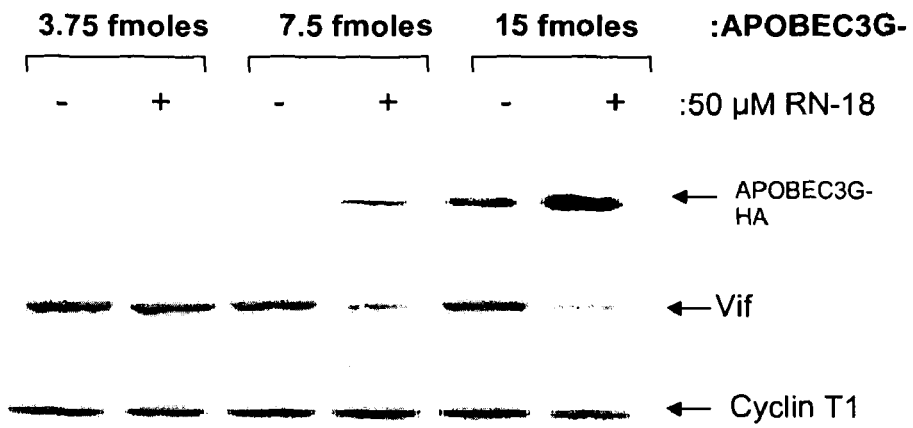
Figure 21B
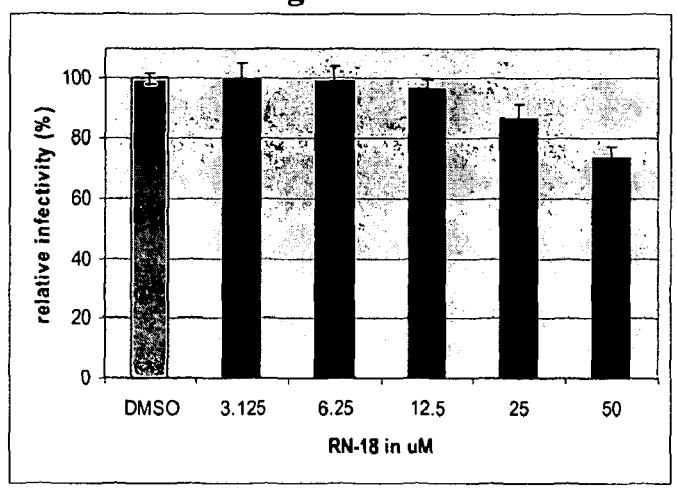
Figure 21C
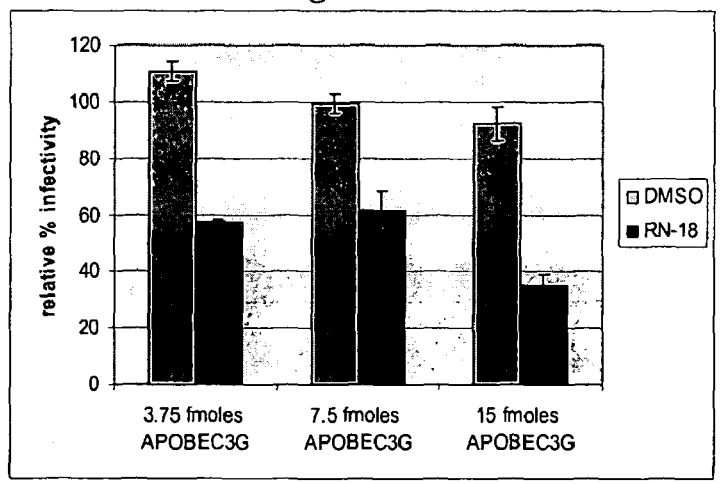
Figure 21D
Figure 22A

Figure 22B
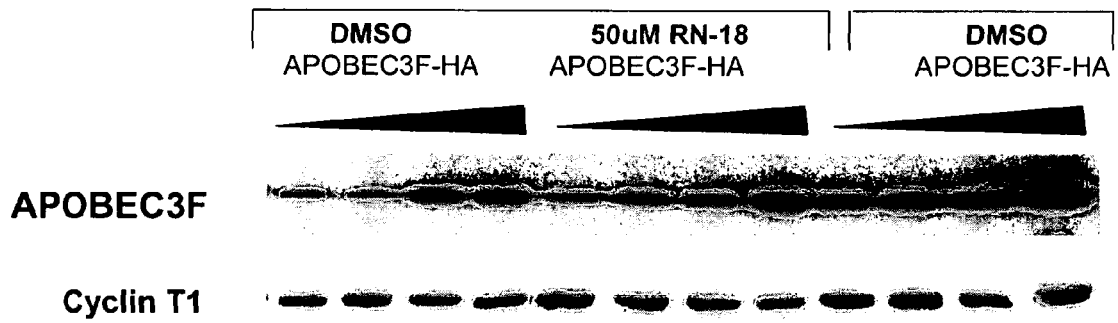

pNL4-3Luc-E-R- pNL4-3 ΔVif Luc-E-R-

SEQUENCE LISTING

<160> NUMBER OF SEQ ID NOS: 4

<210> SEQ ID NO 1
<211> LENGTH: 5
<212> TYPE: RNA
<213> ORGANISM: Artificial Sequence
<220> FEATURE:
<223> OTHER INFORMATION: Consensus sequence

<400> SEQUENCE: 1 ccacc                                                                  5

<210> SEQ ID NO 2
<211> LENGTH: 10
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 2
<223> OTHER INFORMATION: n = zero, one or more c, g, a or u

```
-continued

<400> SEQUENCE: 2 gnccaccaug                                                              10

<210> SEQ ID NO 3
<211> LENGTH: 8
<212> TYPE: RNA
<213> ORGANISM: Artificial Sequence
<220> FEATURE:
<223> OTHER INFORMATION: Synthetically generated oligonucleotide

<400> SEQUENCE: 3 ccaccaug                                                                 8

<210> SEQ ID NO 4
<211> LENGTH: 7
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 4
<223> OTHER INFORMATION: n = zero, one or more c, g, a or u

<400> SEQUENCE: 4 uganaaa                                                                  7
```

COMPOSITION AND SYNTHESIS OF NEW REAGENTS FOR INHIBITION OF HIV REPLICATION

CLAIM OF PRIORITY

This application claims the benefit under 35 USC §119(e) of U.S. Provisional Patent Application Ser. No. 60/725,043, filed on Oct. 6, 2005, the entire contents of which are hereby incorporated by reference.

FEDERALLY SPONSORED RESEARCH OR DEVELOPMENT

This invention was made with Government support under Grant Nos. AI041404 and AI043198, awarded by the National Institutes of Health. The Government has certain rights in the invention.

TECHNICAL FIELD

This invention relates to compounds that inhibit human immunodeficiency virus (HIV) replication.

BACKGROUND

HIV-1 infectivity is highly dependent on the viral-encoded gene Virion Infectivity Factor (Vif). Vif has been implicated in HIV-1 infectivity based on the discovery of varied responses that different types of human cells have to HIV-1 lacking Vif. Some cell types infected with HIV-1 lacking Vif still produce infectious virus and are called permissive cell types. In other cell types, designated non-permissive, HIV-1 encoding Vif can produce infectious virus while HIV-1 lacking Vif cannot.

One protein, called "apolipoprotein B mRNA-editing enzyme, catalytic polypeptide-like 3G" (APOBEC3G) (previously named Cem15), has been discovered that can cause cells to become immune to HIV-1 lacking Vif (i.e., they become non-permissive) (Madani and Kabat, J. Virol. 74:5982-5987(2000)). As a DNA editing enzyme, APOBEC3G severely mutates newly made viral cDNA, which is DNA synthesized from viral RNA during HIV-1 reverse transcription (Gu and Sundquist, Nature 424:21-22 (2003)). In the absence of Vif, APOBEC3G is packaged with the virus and exerts its effect after the virus infects another host cell. Highly mutating viral cDNA during the early stages of reverse transcription leads to destruction of the HIV-1 genome and a detrimentally high mutation rate within genes encoded by the HIV-1 genome (Gu et al., supra). Thus, APOBEC3G has damaging effects on HIV-1 that are prevented by the presence of Vif during HIV-1 infection. Apolipoprotein B mRNA editing enzyme, catalytic polypeptide-like 3F (APOBEC3F) is closely related to APOBEC3G, and has also been shown to have antiretroviral activity in vitro (Cho et al., J Virol. 80(4):2069-2072 (2006)).

SUMMARY

The invention is based, in part, on the discovery that certain compounds described herein inhibit Virion Infectivity Factor (Vif) involved in HIV replication. These inhibitors of protein function also affect the cellular levels of a second protein. In some embodiments, the first protein is Vif and the second protein is apolipoprotein B mRNA-editing enzyme, catalytic polypeptide-like 3G (APOBEC3G) and/or APBEC3F.

In one aspect, the invention features the small molecules identified and described herein, e.g., Vif inhibitors, and compositions including one or more small molecule inhibitors of Vif and a pharmaceutically acceptable carrier, e.g., having a formula shown in FIGS. 1-10B (e.g., FIGS. 1, 2, 3, 4, 5, 6, 7, 8, 9A, 9B, 9C, 9D, 9E, 9F, 9G, 9H, 9I, 9J, 9K, 9L, 9M, 9N, 9O, 9P, 9Q, 9R, 9S, 9T, 9U, 9V, 9W, 9X, 9Y, 9Z, 9AA, 9BB, 9CC, 9DD, 9EE, 9FF, 9GG, 10A, and/or 10B), FIG. 18, and/or FIGS. 19A-D (e.g., FIGS. 19A, 19B, 19C, and/or 19D), or an enantiomer, diastereomer, or a pharmaceutically acceptable salt thereof, and pharmaceutical compositions for inhibiting Vif that include a pharmaceutically carrier and a therapeutically effective amount of an inhibitor described herein. A Vif inhibitor, as described herein, is a small molecule compound that can have one or more of the following activities: compounds that enhance Vif degradation/turnover; compounds that stabilize APOBEC3G and/or APOBEC3F; compounds that interfere with Vif-APOBEC3G and/or APOBEC3F interactions; and compounds that enhance cellular concentration of APOBEC3G and/or APOBEC3F. In some embodiments, the compounds described herein are purified.

In a further aspect, the invention provides methods of treating subjects infected with a virus containing a VIF, e.g., HIV. The methods include administering to the subject a therapeutically effective amount of a compound or composition described herein. In some embodiments, the methods further include administering a second therapeutic agent, e.g., a non-nucleoside reverse transcriptase inhibitor (NNRTI) such as efavirenz (Sustiva™), nevirapine (Viramune™) and delavirdine (Rescriptor™); a nucleoside reverse transcriptase inhibitor (NRTI) such as AZT (zidovudine, Retrovir™)/3TC (lamivudine, Epivir™) and d4T (stavudine, Zerit™)/3TC, and d-drugs (ddI [didanosine, Videx™/VidexEC™], ddC [zalcitabine, Hivid™], d4T); a nucleotide reverse transcriptase inhibitor, such as tenofovir (Viread™); and a fusion inhibitor, such as enfuvirtide (Fuzeon™). In some embodiments, the compound or pharmaceutical composition is administered as part of a highly active antiretroviral therapy (HAART) regimen.

In a further aspect, the invention provides methods of synthesis of Vif inhibitors as described herein, e.g., including copper-catalyzed coupling of a haloaryl and a thioaryl using microwave irradiation.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 10A-10B are lists of known compounds that are shown herein to be inhibitors of HIV replication.

FIG. 11B, CFP-APOBEC3G co-transfected with increasing molar ratios of YFP-Vif; FIG. 11C, CFP-APOBEC3G co-transfected with increasing molar ratios of NL4GFP-HIV proviral DNA. Virus production was measured by virus-derived Green Fluorescent Protein (GFP). FIG. 11D, cells co-transfected with a constant amount of pNL-A1Δvif or pNL-A1 and a range of pCFP-APO. The molar ratio of each vector (pHIV:pAPO) is presented (1=130 fmoles).

FIG. 15A, 293T Cells expressing only YFP-Vif. FIG. 15B, 293T Cells expressing the target protein, APOBEC3G FIG. 15C, 293T cells expressing YFP-Vif, CFP-ABOBEC3G or both are cultured in a 96 well plate. After treating each well of cells with a different small molecule, a fluorimeter can be used to screen the 96-well plate for cells emitting increased CFP fluorescence. The symbol ⊘ represents small molecules.

FIG. 21B is a set of Western blots of APOBEC3G, Vif and, cyclin T1 in lysates from 293T cells transfected with pNL-Luc-E-R-, pVSV-G, and 3.75, 7.5 or 15 fmoles APOBEC3G-HA, treated with DMSO (−) or 50 μM Vif inhibitor 1 (+).

FIGS. 21C-D are bar graphs showing infectivity determined by infecting 293T cells for 48 hours with 1 ng virus produced from the producer cells in 21A (results shown in 21C) and 21B (results in 21D). The infectivity of each virus produced without APOBEC3G was normalized to 100%, and data was representative of three independent experiments.

FIGS. 22A-B are Western blots showing that Vif inhibitor 1 increases APOBEC3G (22A) and APOBEC3F (23B) in a dose-dependent manner. Cyclin T1 was used as an internal control.

DETAILED DESCRIPTION

Figure 1:
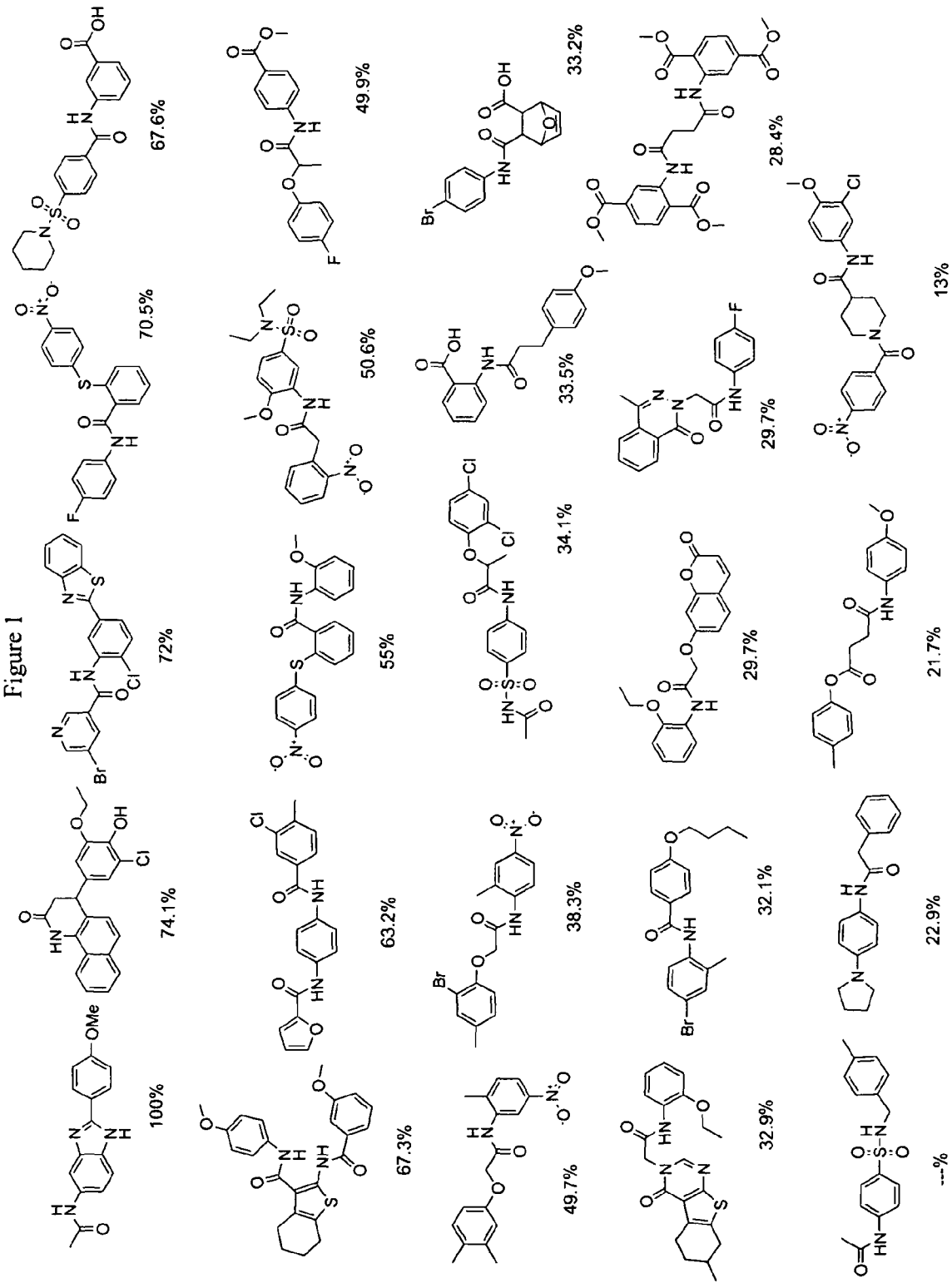
FIGS. 1-7 are lists of compounds that have been identified as Vif inhibitors using the screening method described herein. Compounds have a percent Vif inhibition value provided next to the structure with deltaVif/APOBEC3G having a standard value of 100%.
Figure 2:
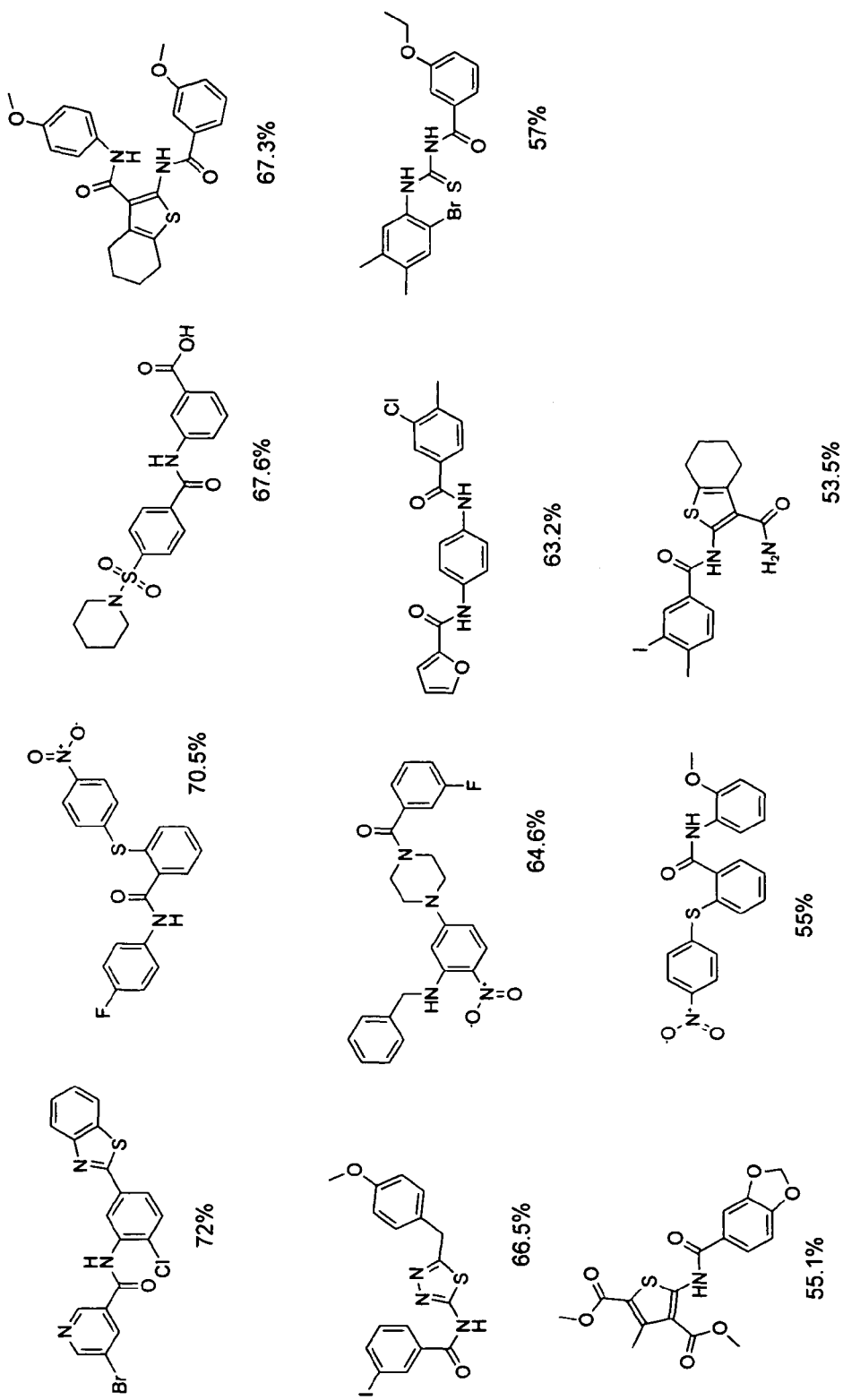
Figure 3:
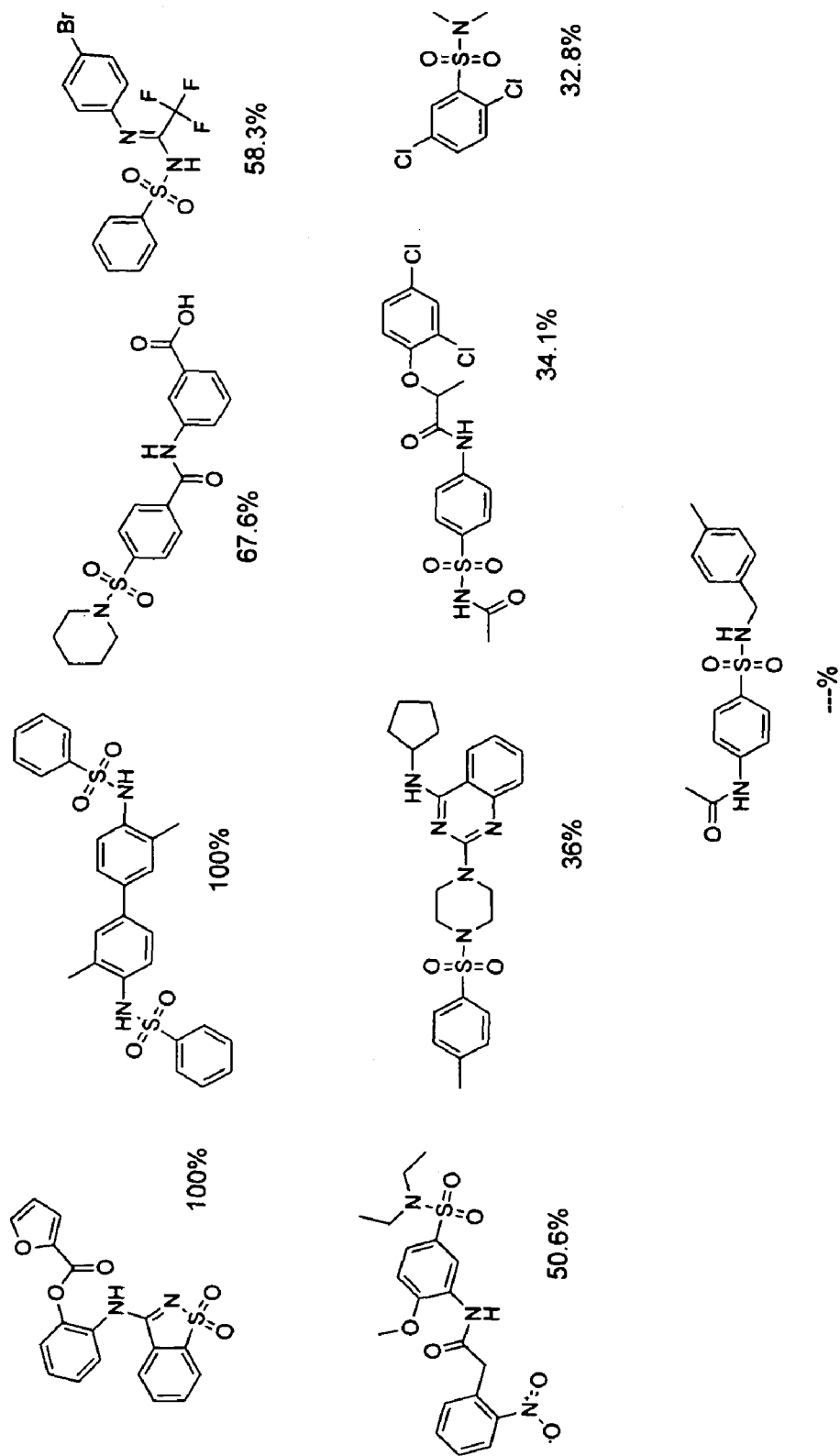
Figure 4:
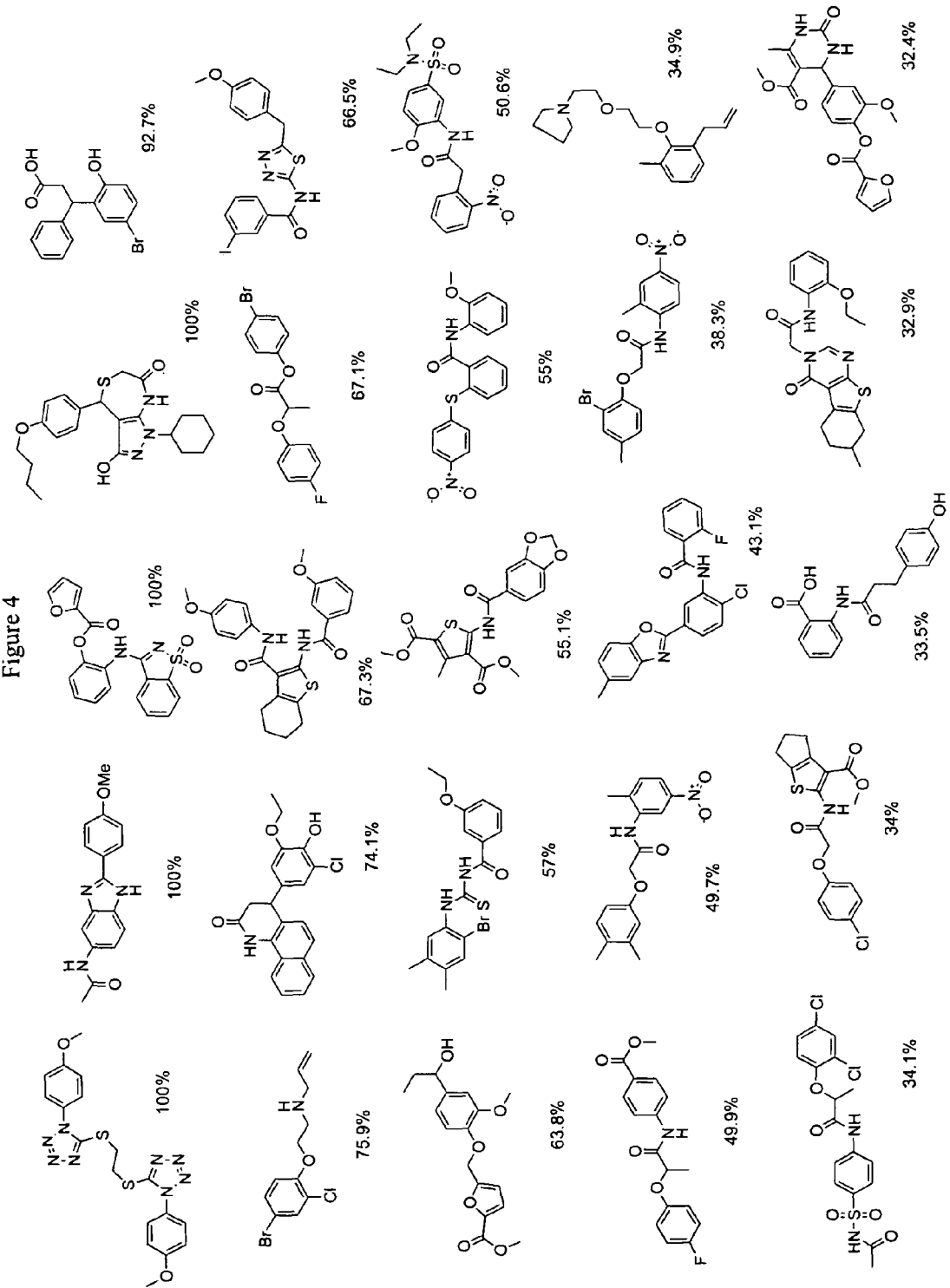
Figure 5:
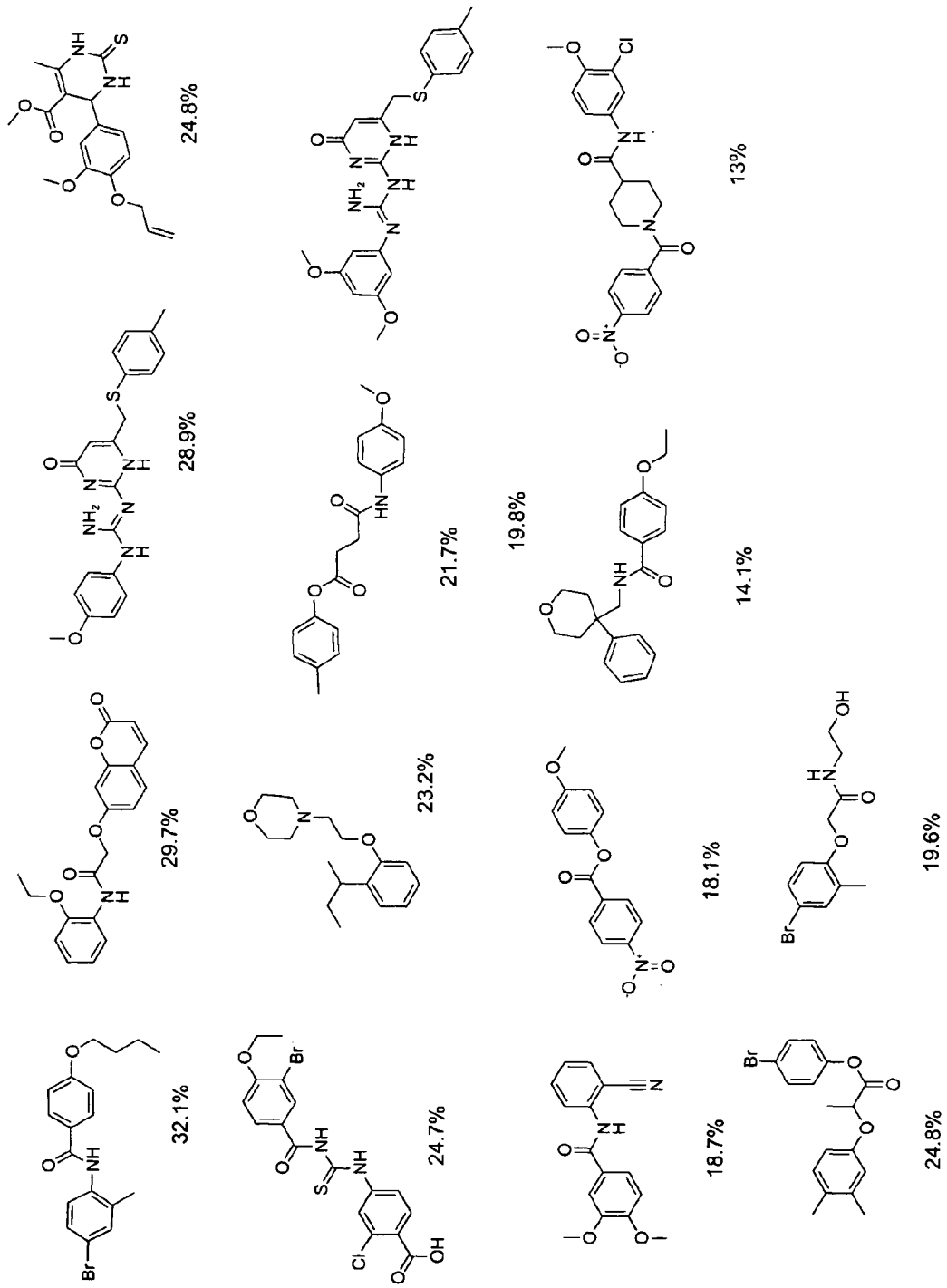
Figure 6:
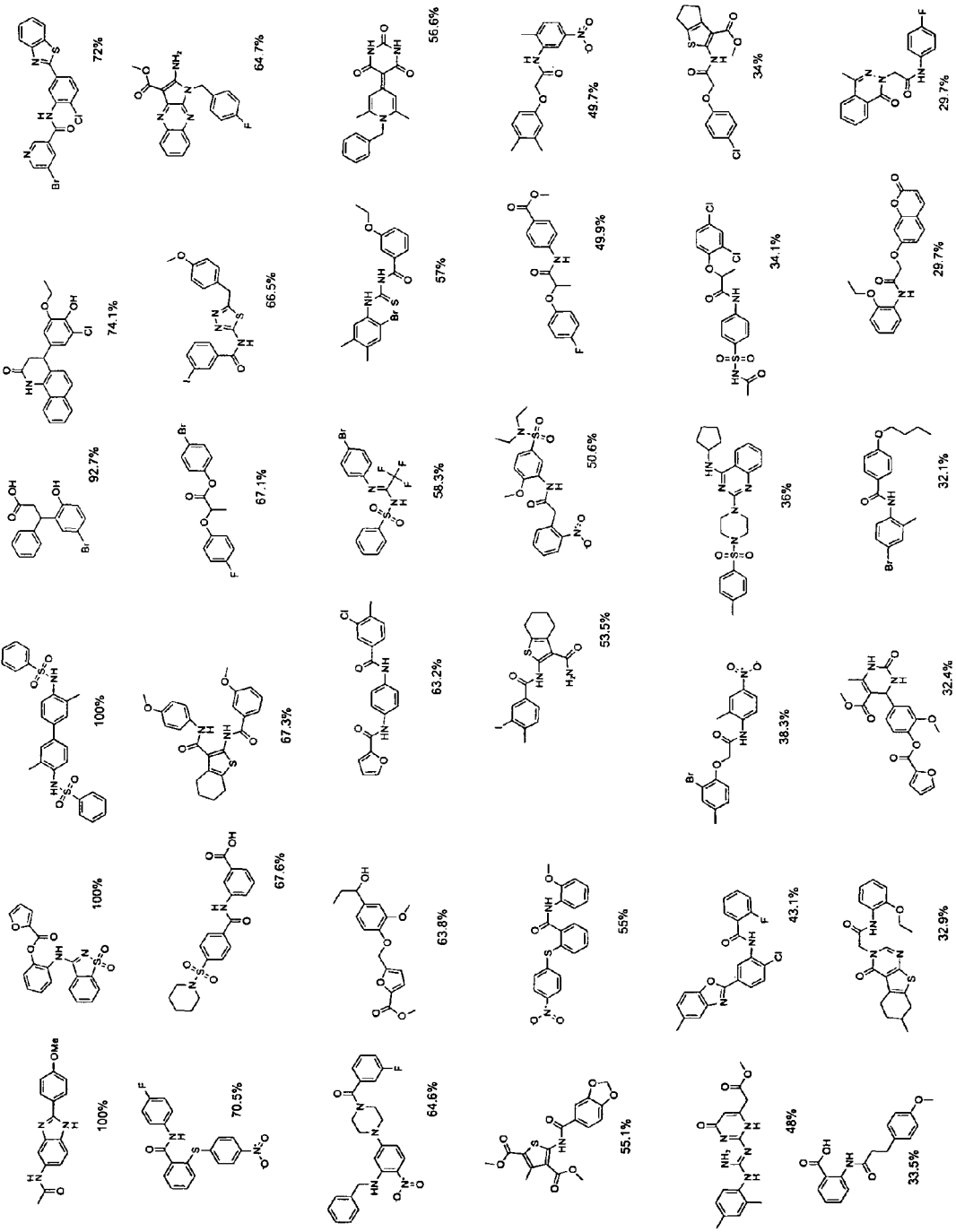
Figure 7:
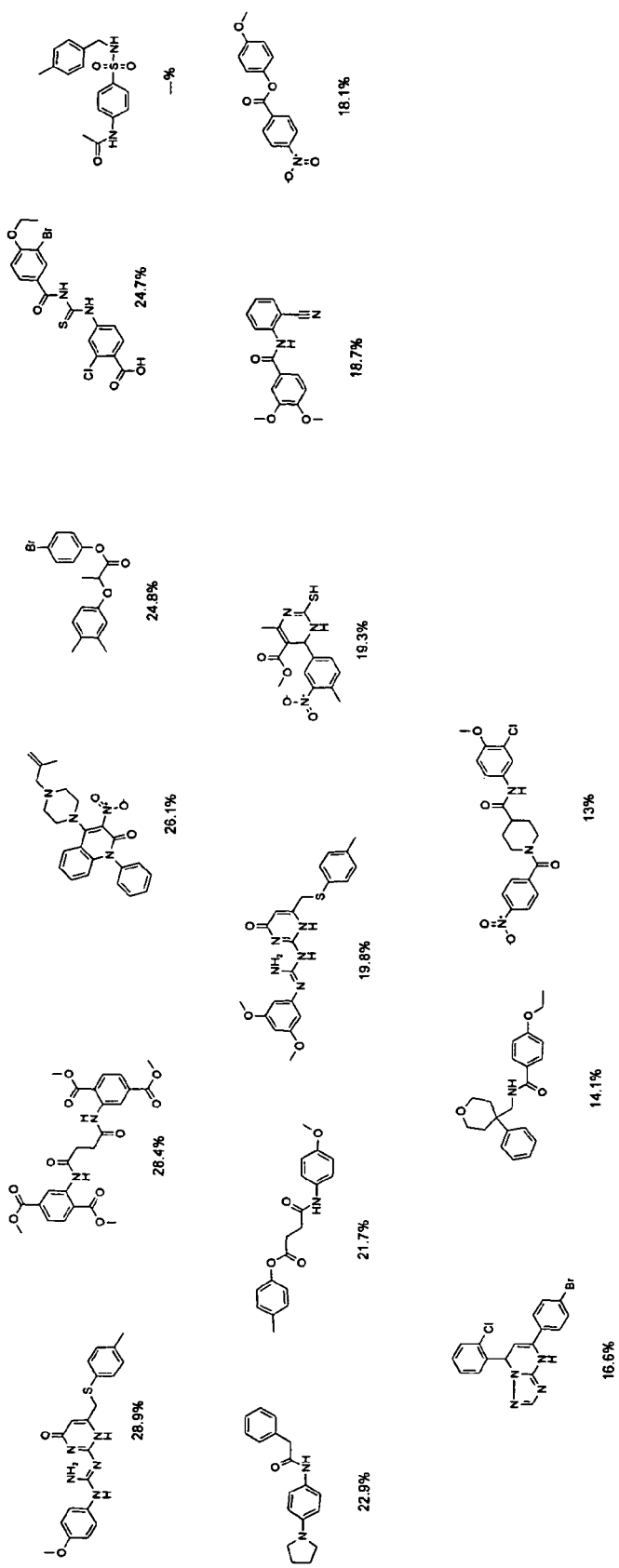
Figure 8:
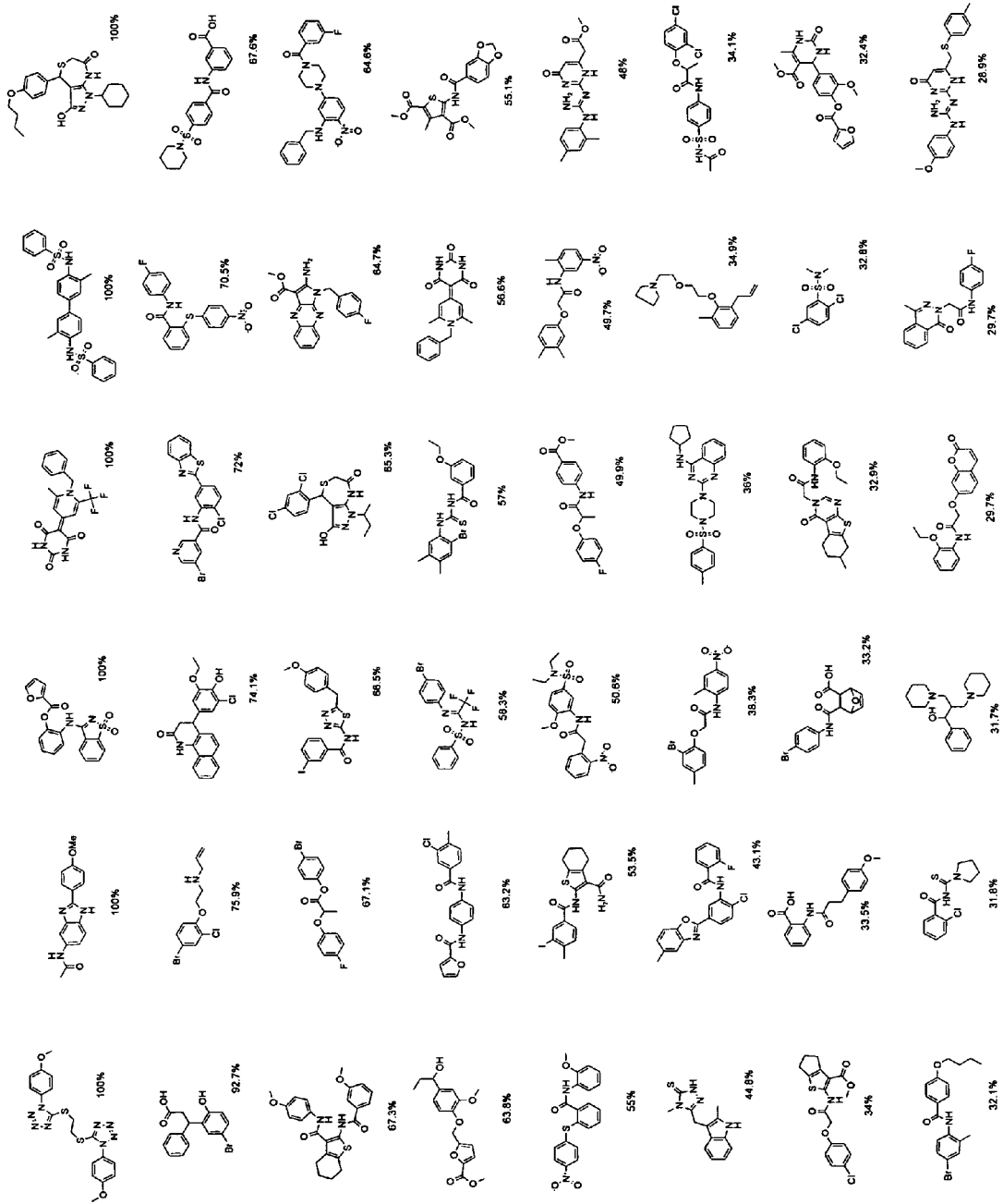
FIG. 8 is a list of compounds that have been selected by the screening method for further analysis. Compounds have a percent Vif inhibition value provided next to the structure with deltaVif/APOBEC3G having a standard value of 100%.
Figure 9A:
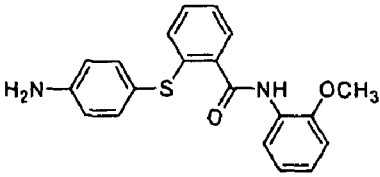
FIGS. 9A-9GG are lists of compounds that are structural analogs of the Vif inhibitors shown in FIGS. 1-8 and 10A-10B.
Figure 9A:
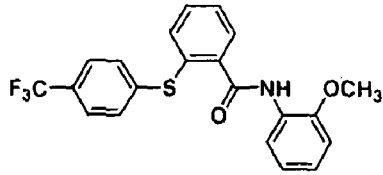
Figure 9A:
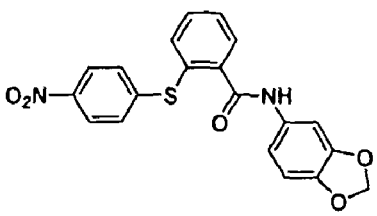
Figure 9A:
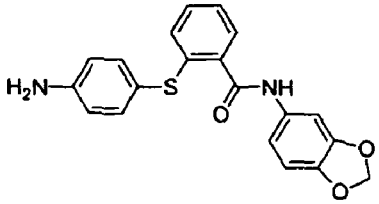
Figure 9A:
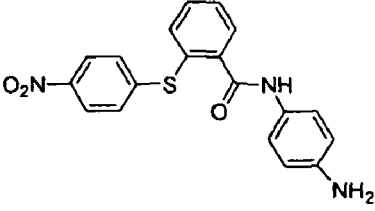
Figure 9A:
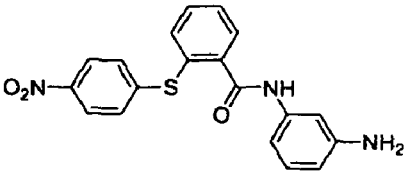
Figure 9A:
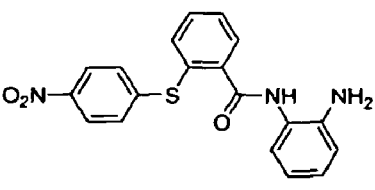
Figure 9B:
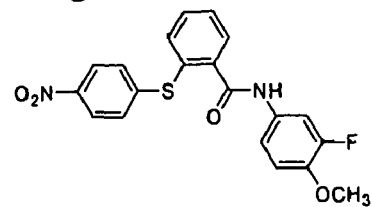
Figure 9B:
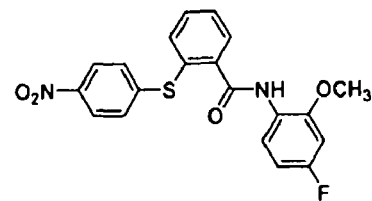
Figure 9B:
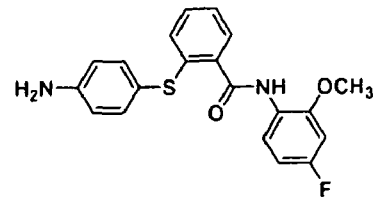
Figure 9B:
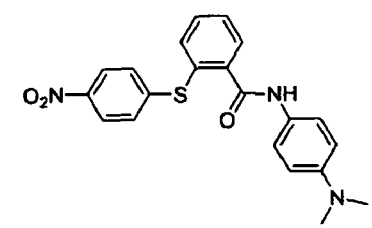
Figure 9B:
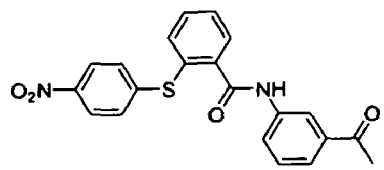
Figure 9B:
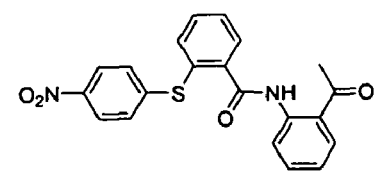
Figure 9B:
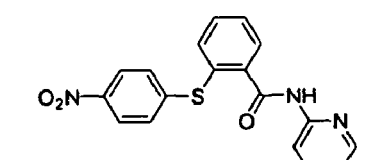
Figure 9B:
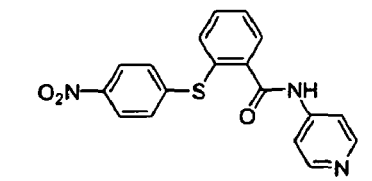
Figure 9C:
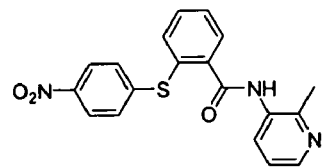
Figure 9C:
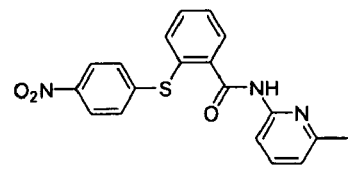
Figure 9C:
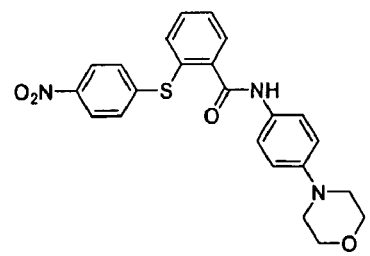
Figure 9C:
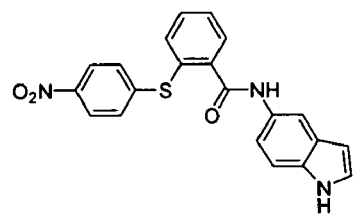
Figure 9C:
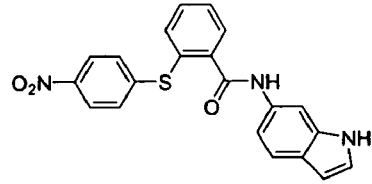
Figure 9C:
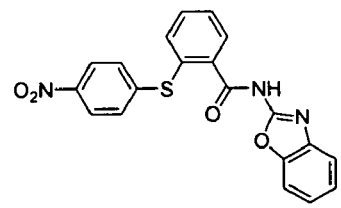
Figure 9C:
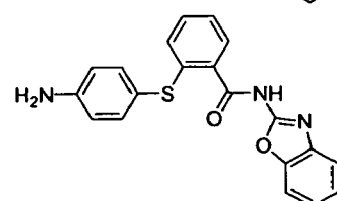
Figure 9C:
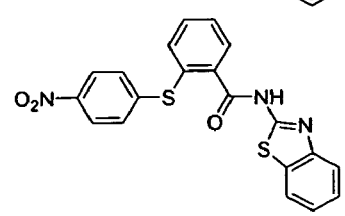
Figure 9D:
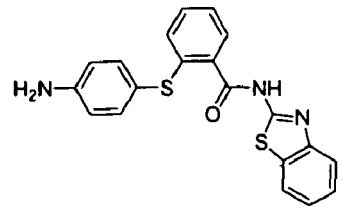
Figure 9D:
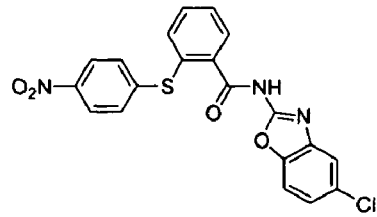
Figure 9D:
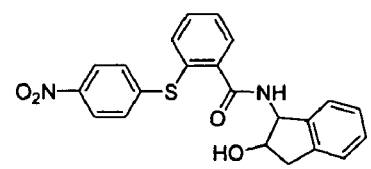
Figure 9D:
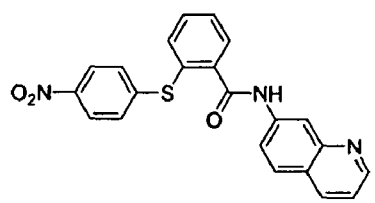
Figure 9D:
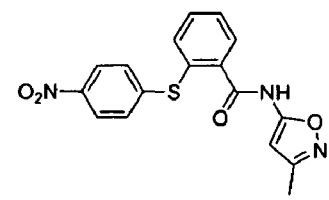
Figure 9D:
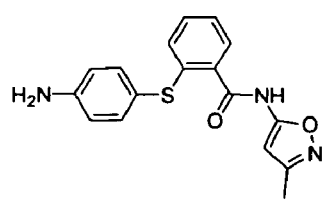
Figure 9D:
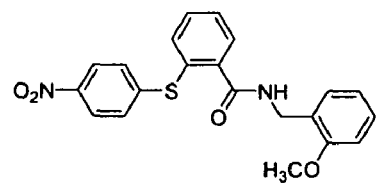
Figure 9D:
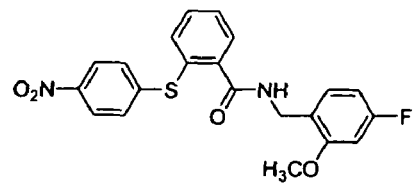
Figure 9E:
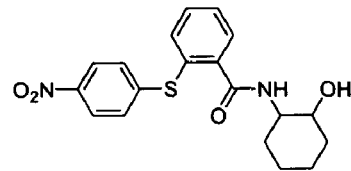
Figure 9E:
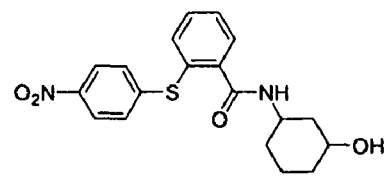
Figure 9E:
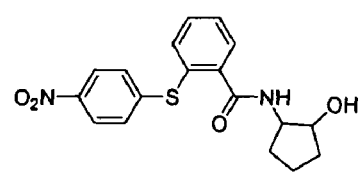
Figure 9E:
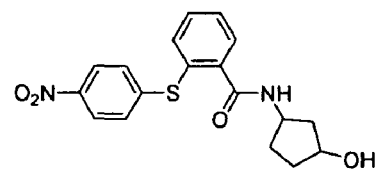
Figure 9E:
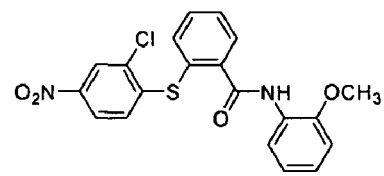
Figure 9E:
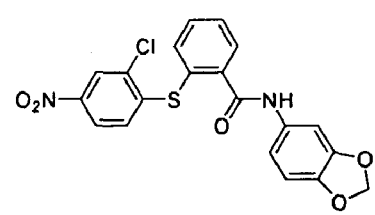
Figure 9E:
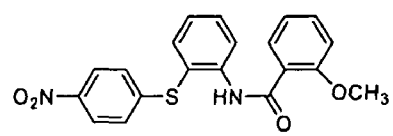
Figure 9E:
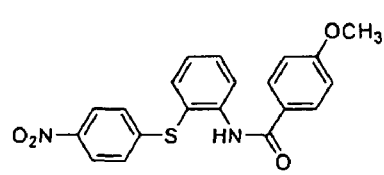
Figure 9F:
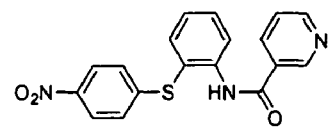
Figure 9F:
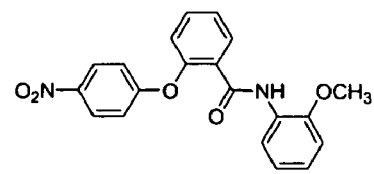
Figure 9F:
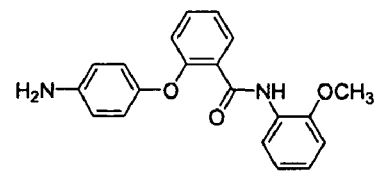
Figure 9F:
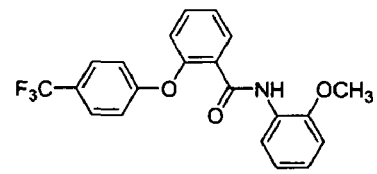
Figure 9F:
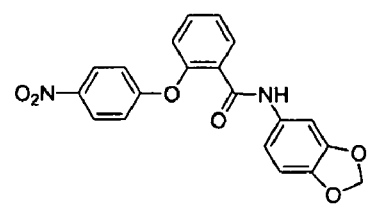
Figure 9F:
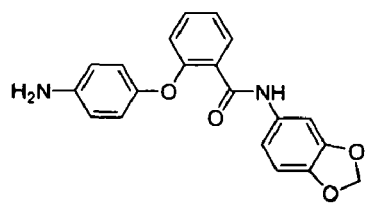
Figure 9F:
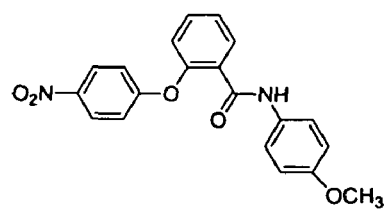
Figure 9F:
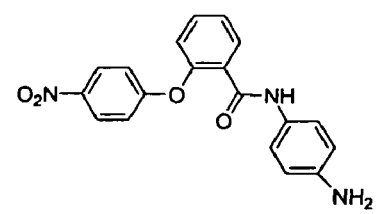
Figure 9G:
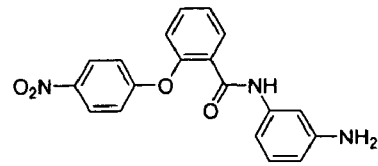
Figure 9G:
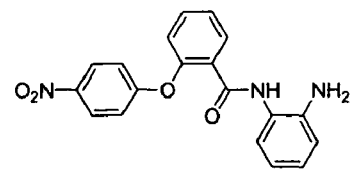
Figure 9G:
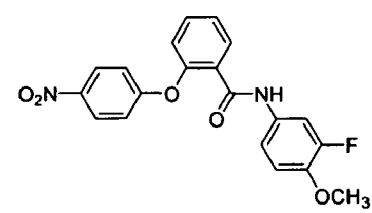
Figure 9G:
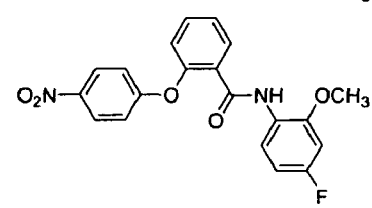
Figure 9G:
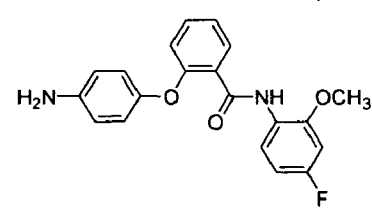
Figure 9G:
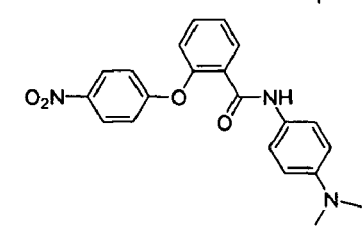
Figure 9G:
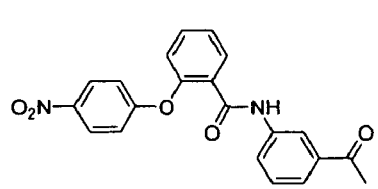
Figure 9G:
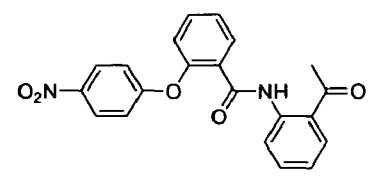
Figure 9H:
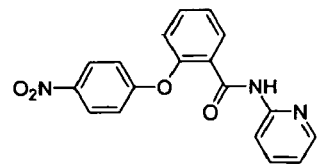
Figure 9H:
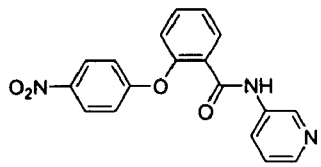
Figure 9H:
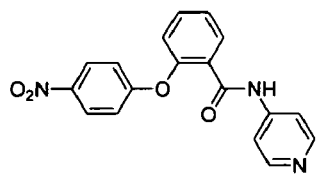
Figure 9H:
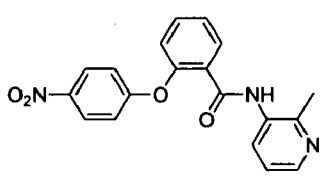
Figure 9H:
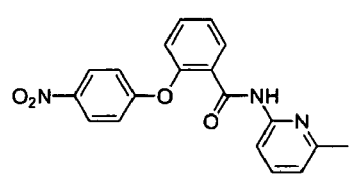
Figure 9H:
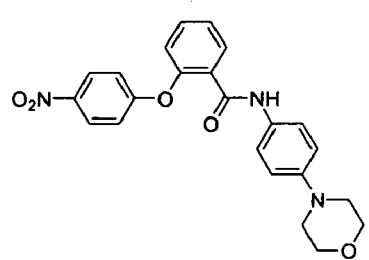
Figure 9H:
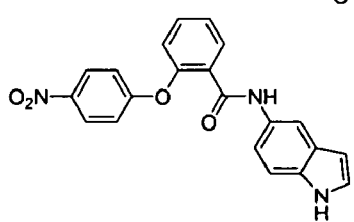
Figure 9H:
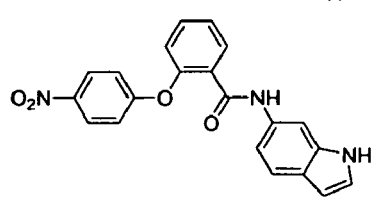
Figure 9I:
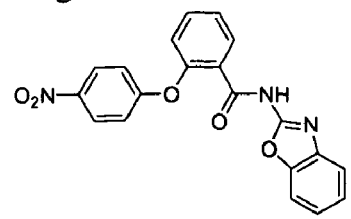
Figure 9I:
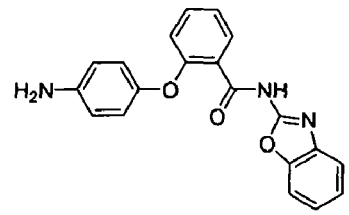
Figure 9I:
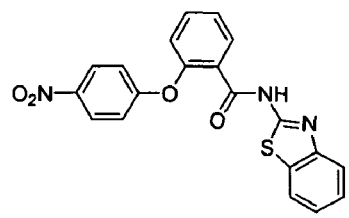
Figure 9I:
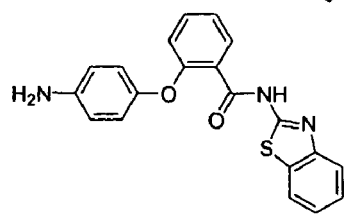
Figure 9I:
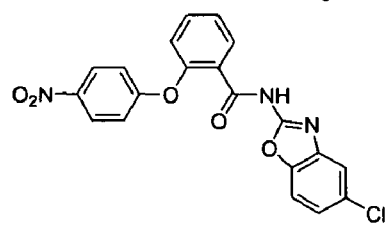
Figure 9I:
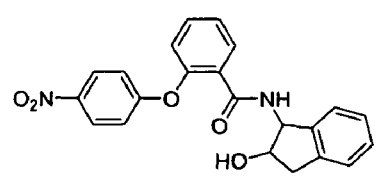
Figure 9I:
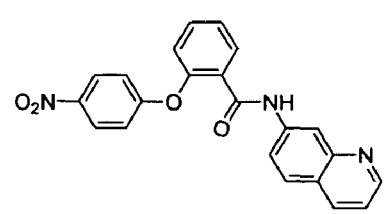
Figure 9I:
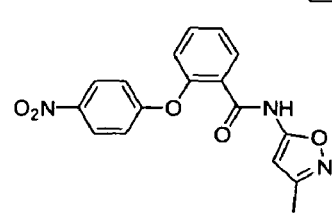
Figure 9J:
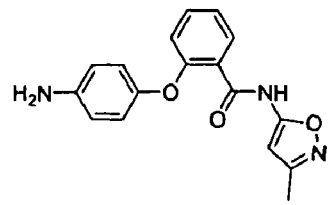
Figure 9J:
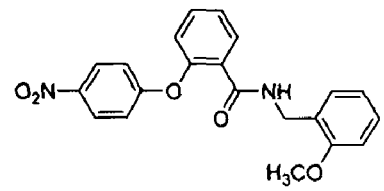
Figure 9J:
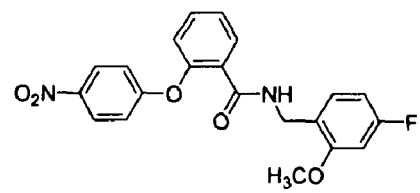
Figure 9J:
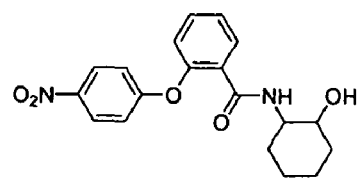
Figure 9J:
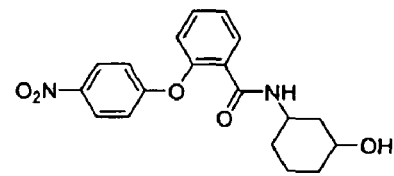
Figure 9J:
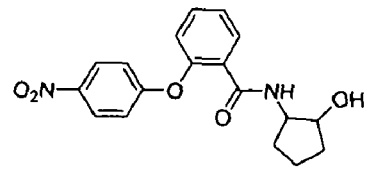
Figure 9J:
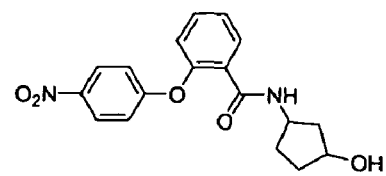
Figure 9J:
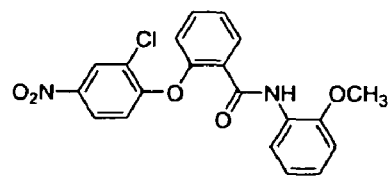
Figure 9K:
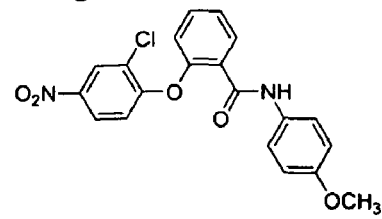
Figure 9K:
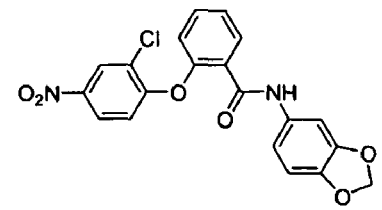
Figure 9K:
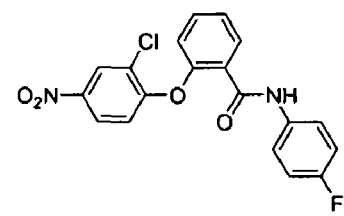
Figure 9K:
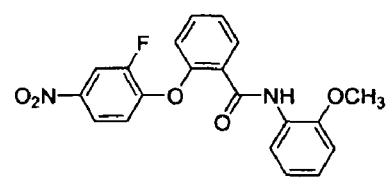
Figure 9K:
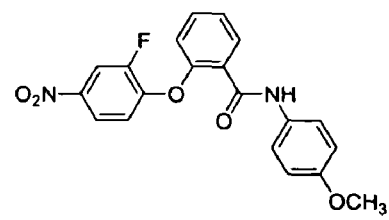
Figure 9K:
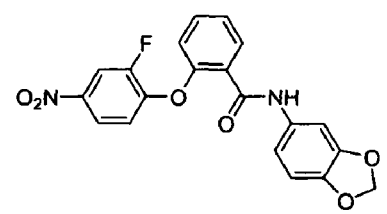
Figure 9K:
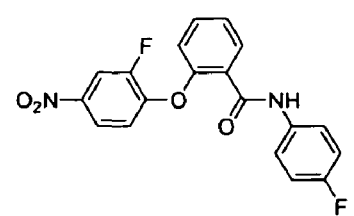
Figure 9K:
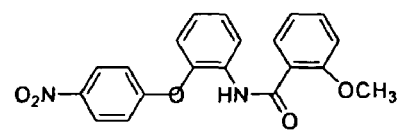
Figure 9L:
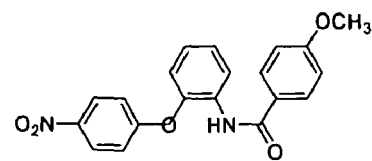
Figure 9L:
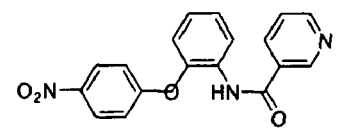
Figure 9L:
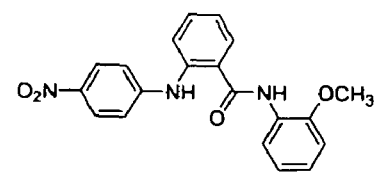
Figure 9L:
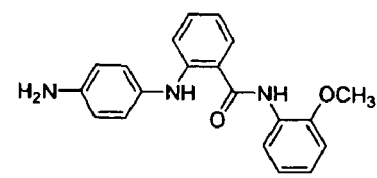
Figure 9L:
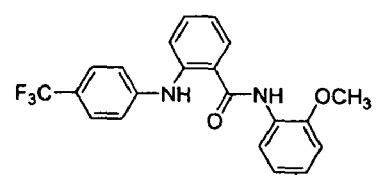
Figure 9L:
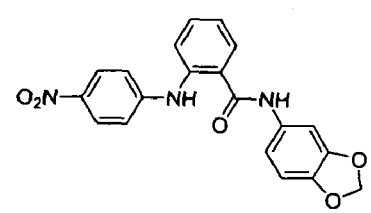
Figure 9L:
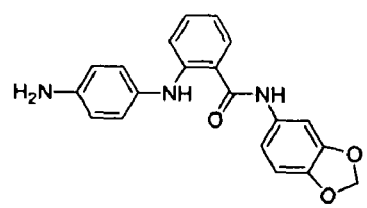
Figure 9L:
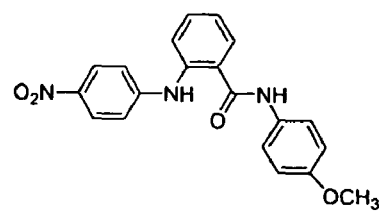
Figure 9M:
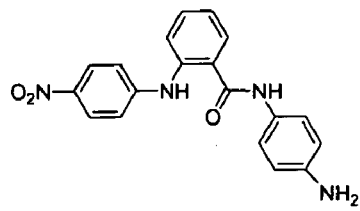
Figure 9M:
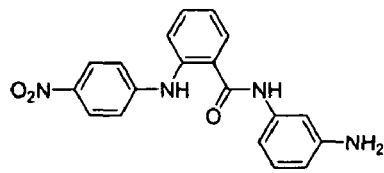
Figure 9M:
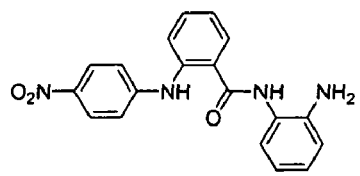
Figure 9M:
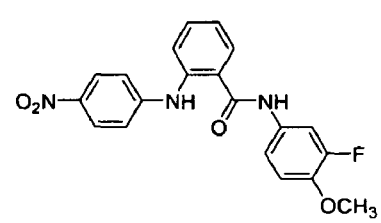
Figure 9M:
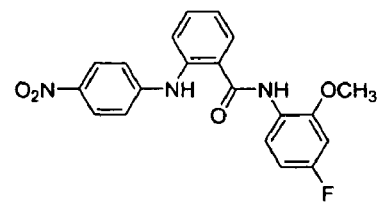
Figure 9M:
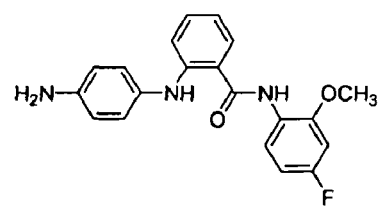
Figure 9M:
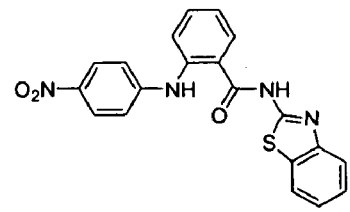
Figure 9M:
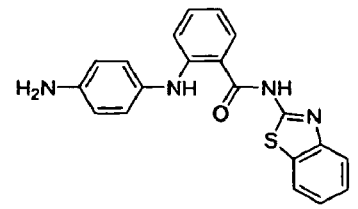
Figure 9N:
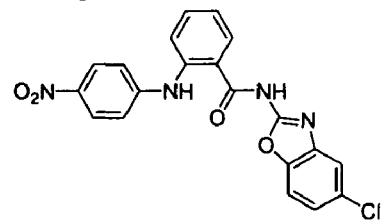
Figure 9N:
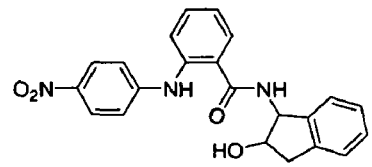
Figure 9N:
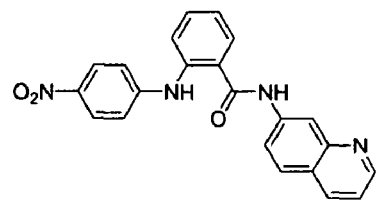
Figure 9N:
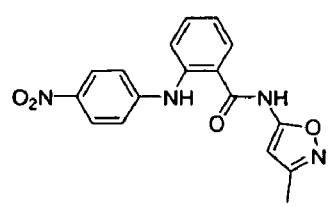
Figure 9N:
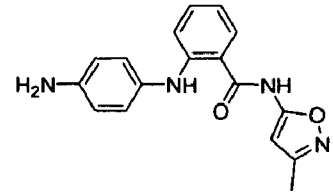
Figure 9N:
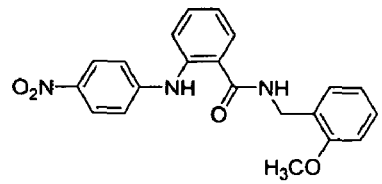
Figure 9N:
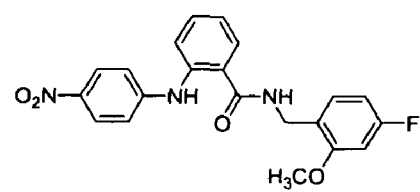
Figure 9N:
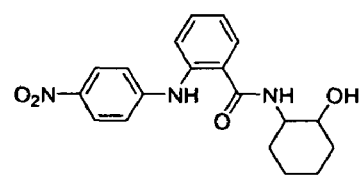
Figure 9O:
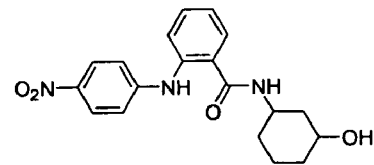
Figure 9O:
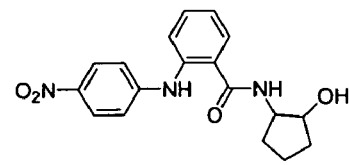
Figure 9O:
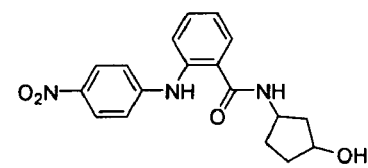
Figure 9O:
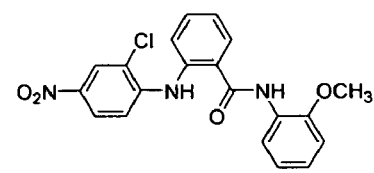
Figure 9O:
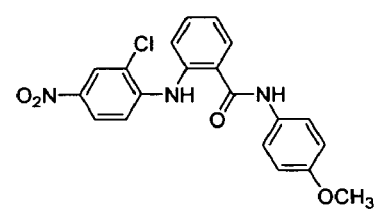
Figure 9O:
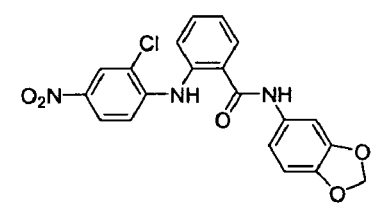
Figure 9O:
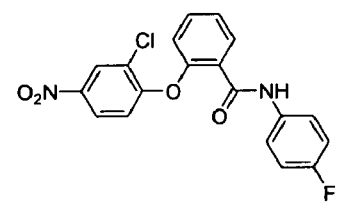
Figure 9O:
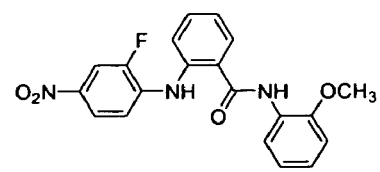
Figure 9P:
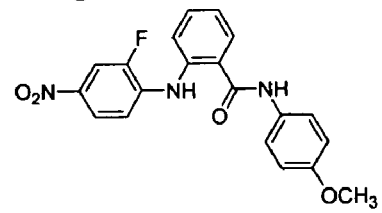
Figure 9P:
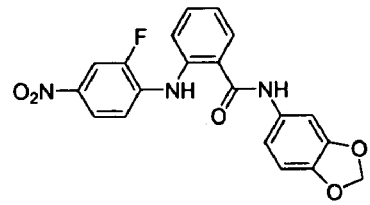
Figure 9P:
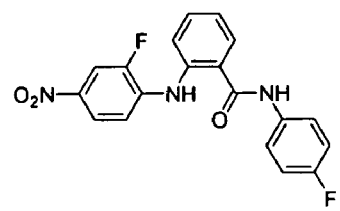
Figure 9P:
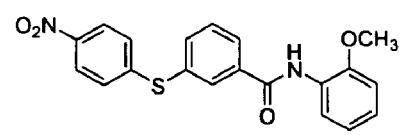
Figure 9P:
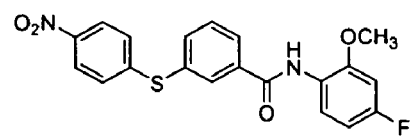
Figure 9P:
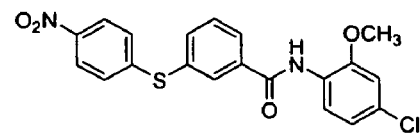
Figure 9P:
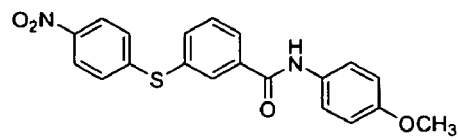
Figure 9P:
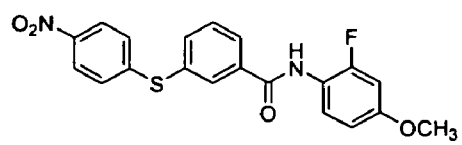
Figure 9Q:
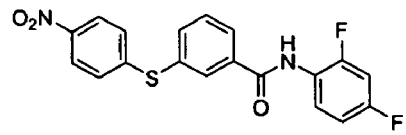
Figure 9Q:
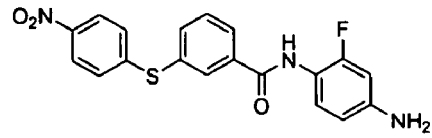
Figure 9Q:
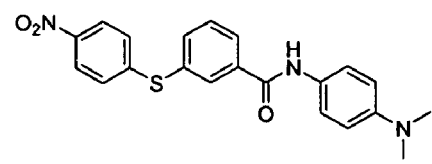
Figure 9Q:
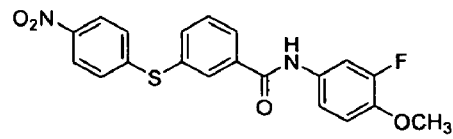
Figure 9Q:
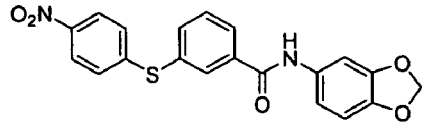
Figure 9Q:
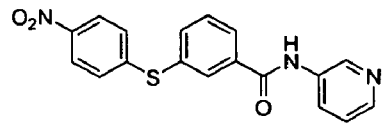
Figure 9Q:
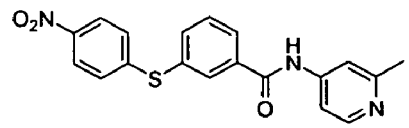
Figure 9Q:
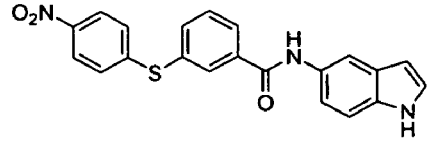
Figure 9R:
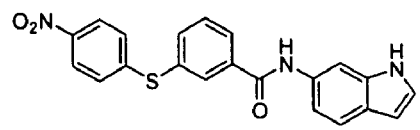
Figure 9R:
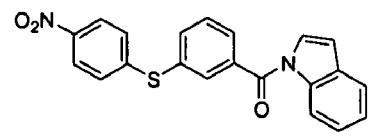
Figure 9R:
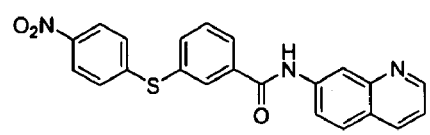
Figure 9R:
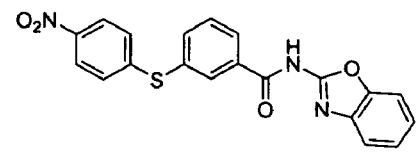
Figure 9R:
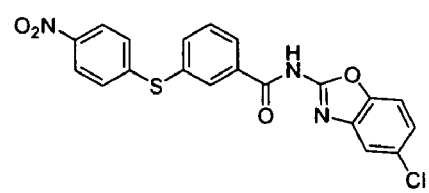
Figure 9R:
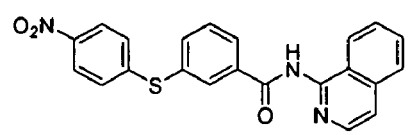
Figure 9R:
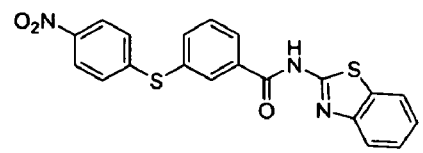
Figure 9R:
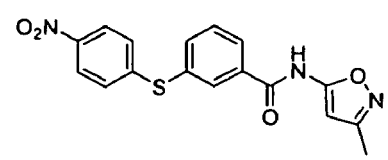
Figure 9S:
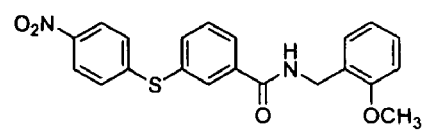
Figure 9S:
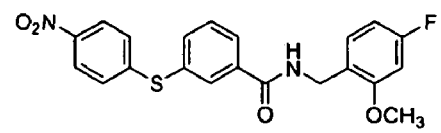
Figure 9S:
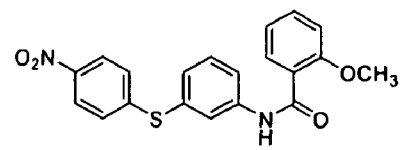
Figure 9S:
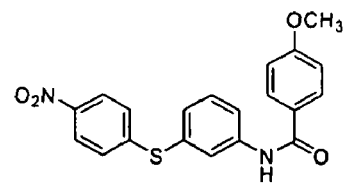
Figure 9S:
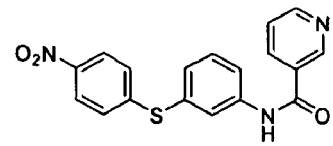
Figure 9S:
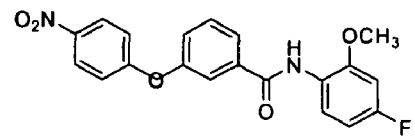
Figure 9S:
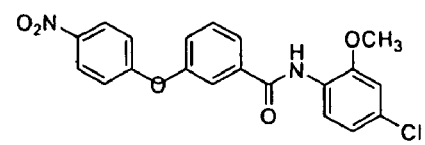
Figure 9S:
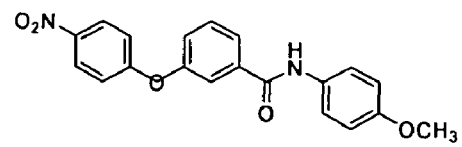
Figure 9T:
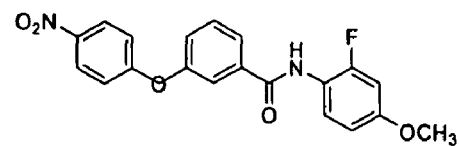
Figure 9T:
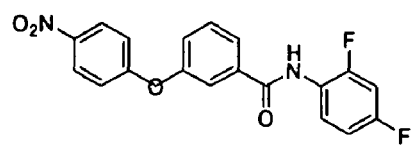
Figure 9T:
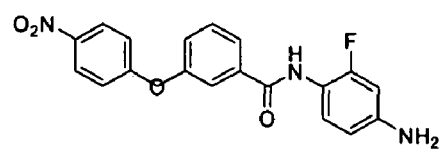
Figure 9T:
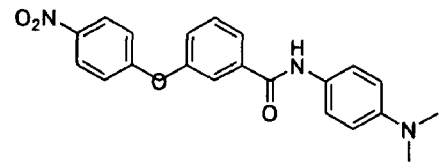
Figure 9T:
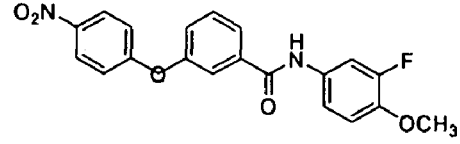
Figure 9T:
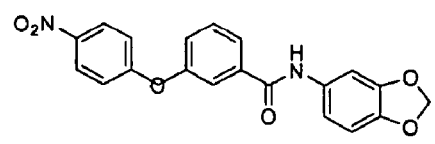
Figure 9T:
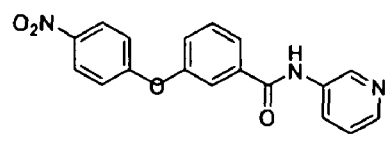
Figure 9T:
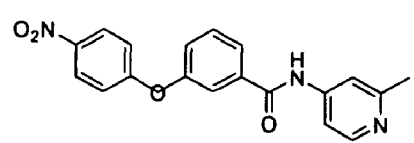
Figure 9U:
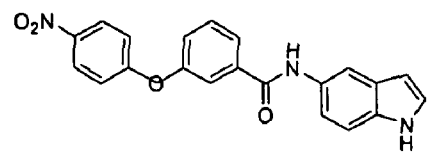
Figure 9U:
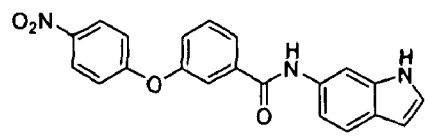
Figure 9U:
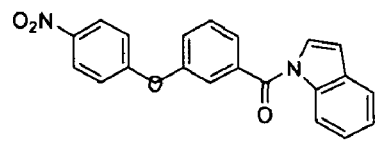
Figure 9U:
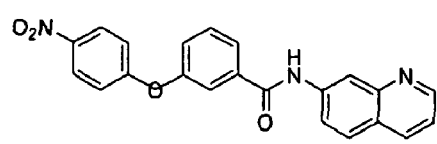
Figure 9U:
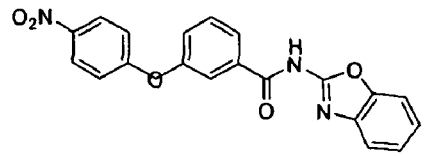
Figure 9U:
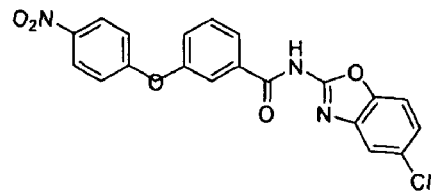
Figure 9U:
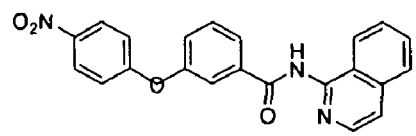
Figure 9U:
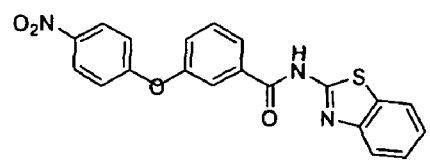
Figure 9V:
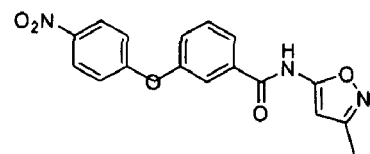
Figure 9V:
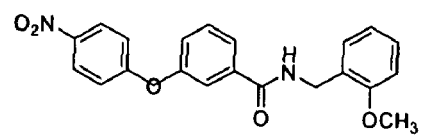
Figure 9V:
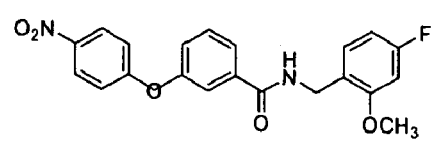
Figure 9V:
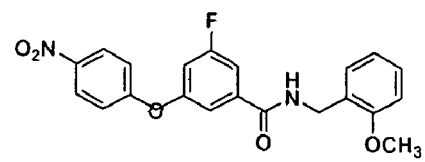
Figure 9V:
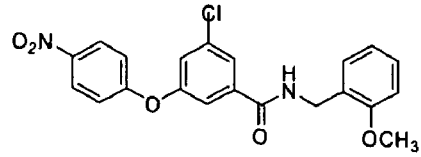
Figure 9V:
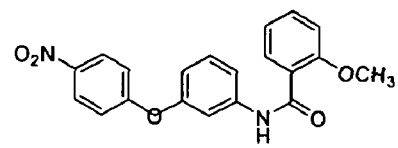
Figure 9V:
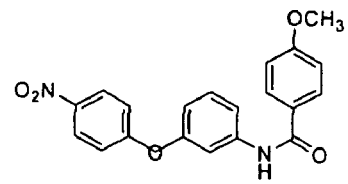
Figure 9V:
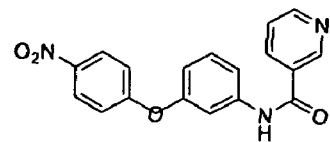
Figure 9W:
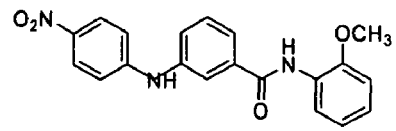
Figure 9W:
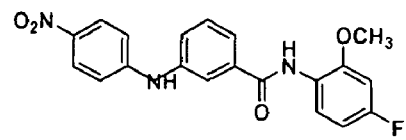
Figure 9W:
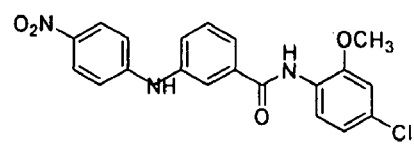
Figure 9W:
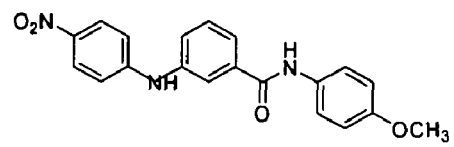
Figure 9W:
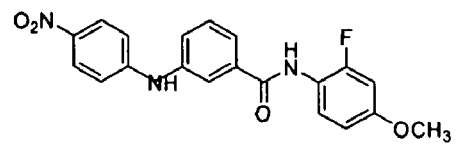
Figure 9W:
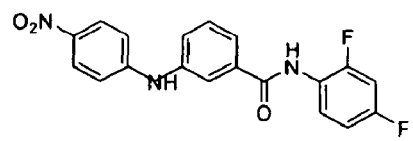
Figure 9W:
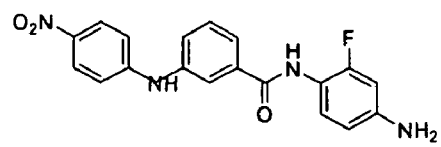
Figure 9W:
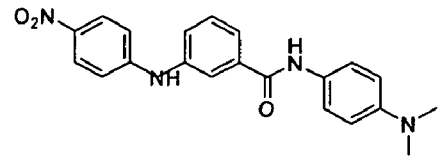
Figure 9X:
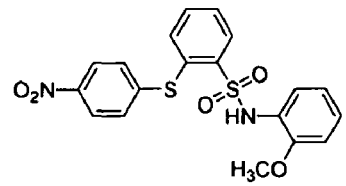
Figure 9X:
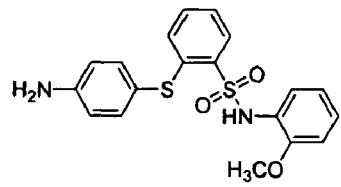
Figure 9X:
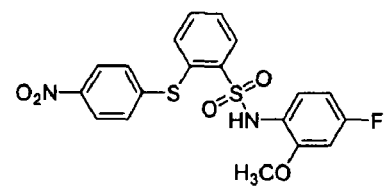
Figure 9X:
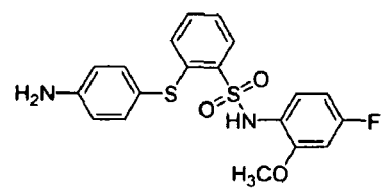
Figure 9X:
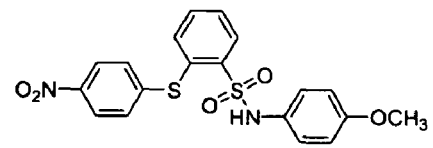
Figure 9X:
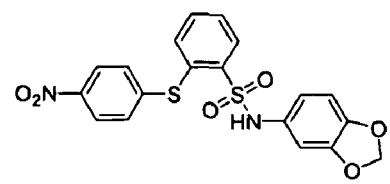
Figure 9X:
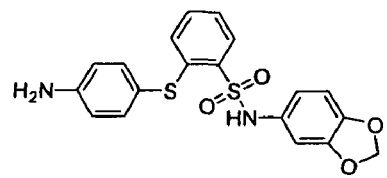
Figure 9X:
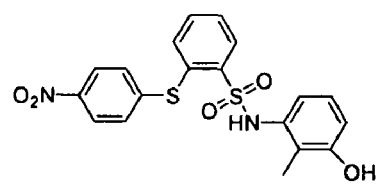
Figure 9Y:
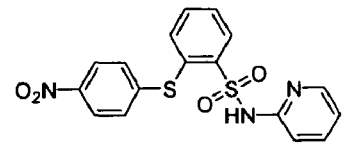
Figure 9Y:
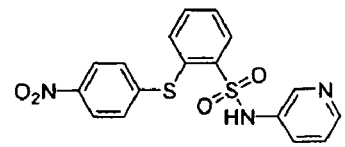
Figure 9Y:
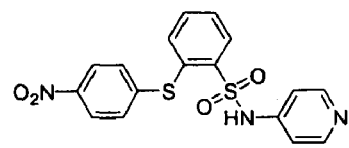
Figure 9Y:
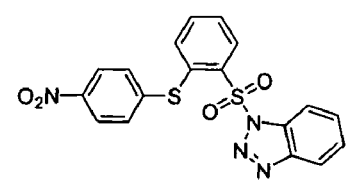
Figure 9Y:
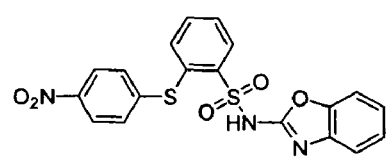
Figure 9Y:
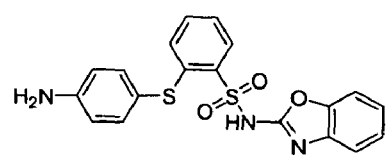
Figure 9Y:
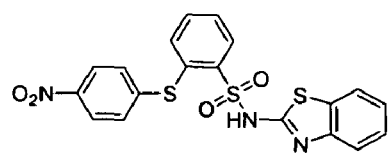
Figure 9Y:
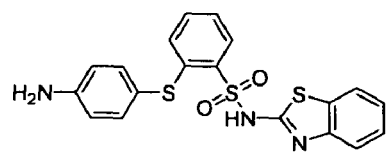
Figure 9Z:
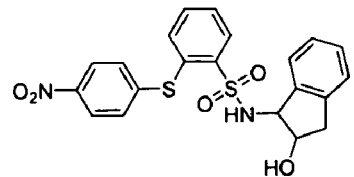
Figure 9Z:
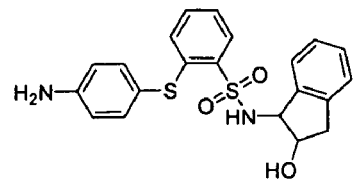
Figure 9Z:
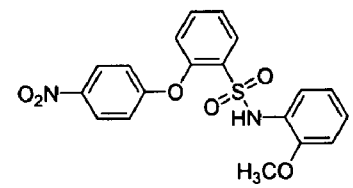
Figure 9Z:
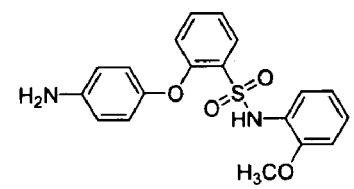
Figure 9Z:
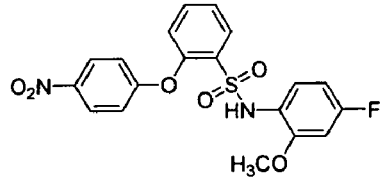
Figure 9Z:
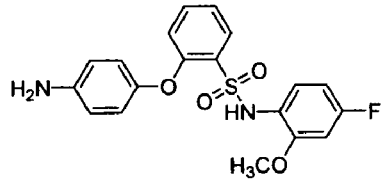
Figure 9Z:
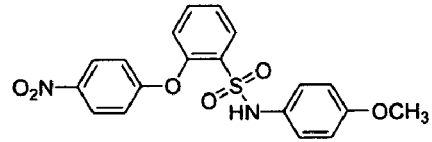
Figure 9Z:
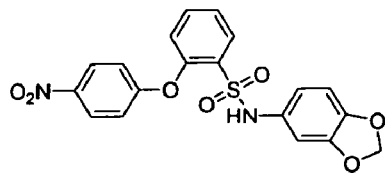
Figure 9A:
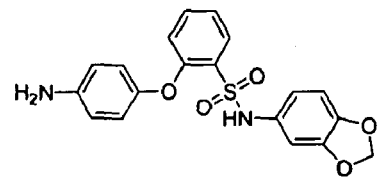
Figure 9A:
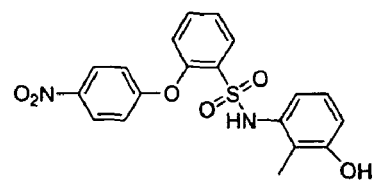
Figure 9A:
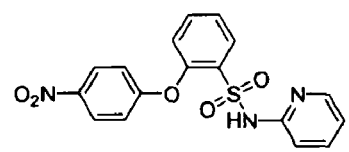
Figure 9A:
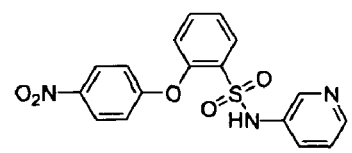
Figure 9A:
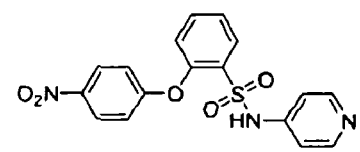
Figure 9A:
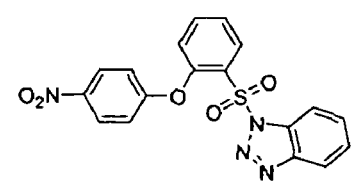
Figure 9A:
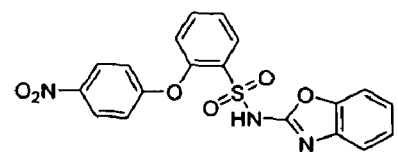
Figure 9A:
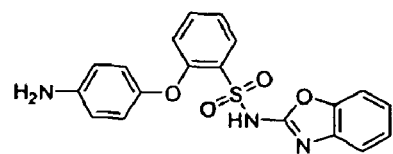
Figure 9B:
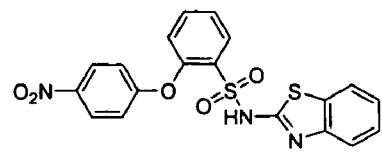
Figure 9B:
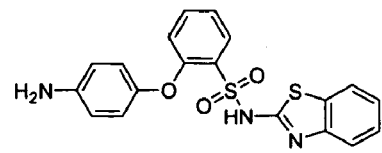
Figure 9B:
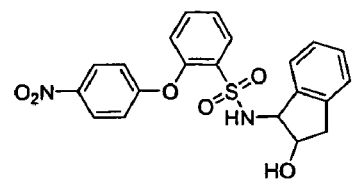
Figure 9B:
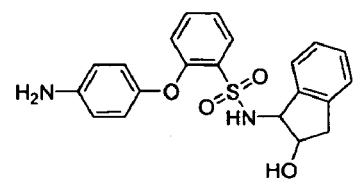
Figure 9B:
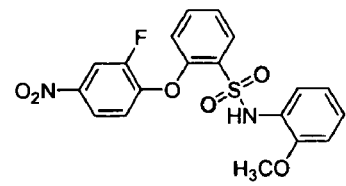
Figure 9B:
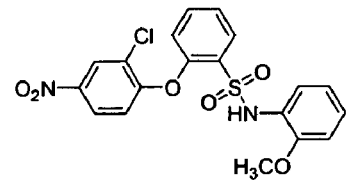
Figure 9B:
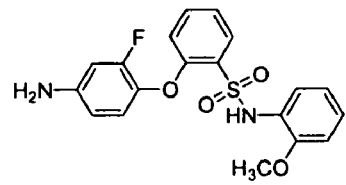
Figure 9B:
Figure 9C:
Figure 9C:
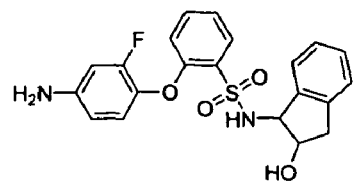
Figure 9C:
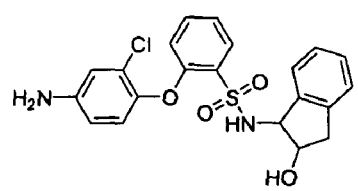
Figure 9C:
Figure 9C:
Figure 9C:
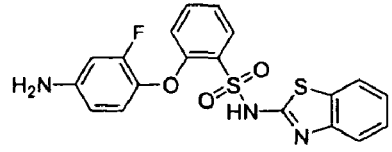
Figure 9C:
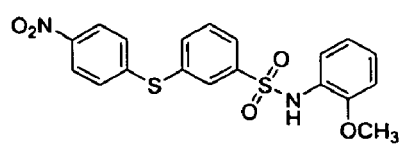
Figure 9C:
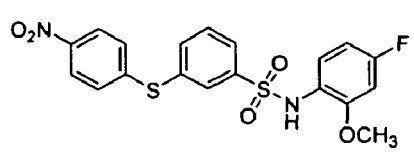
Figure 9D:
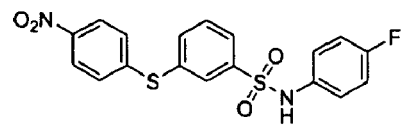
Figure 9D:
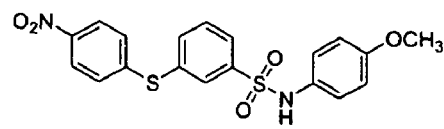
Figure 9D:
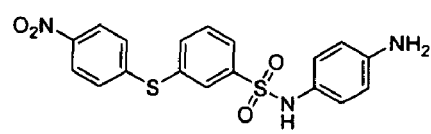
Figure 9D:
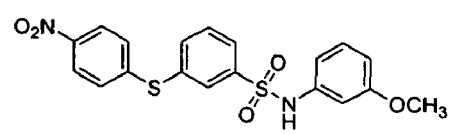
Figure 9D:
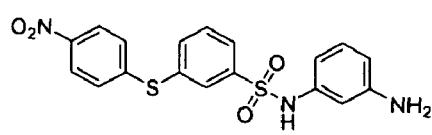
Figure 9D:
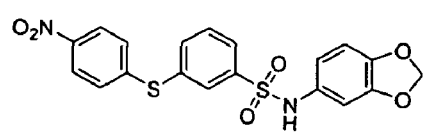
Figure 9D:
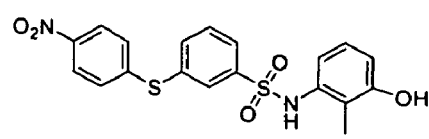
Figure 9D:
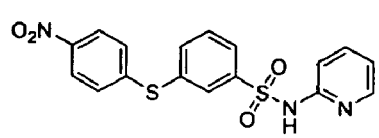
Figure 9E:
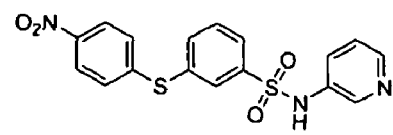
Figure 9E:
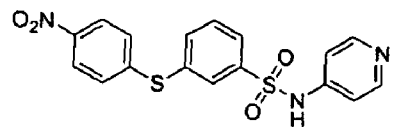
Figure 9E:
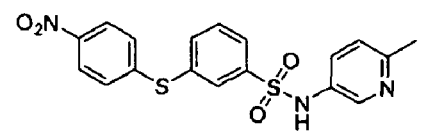
Figure 9E:
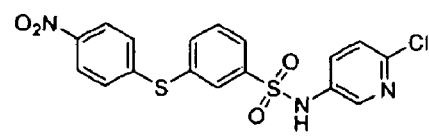
Figure 9E:
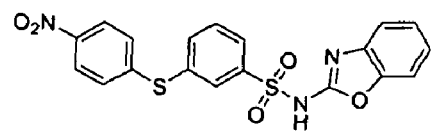
Figure 9E:
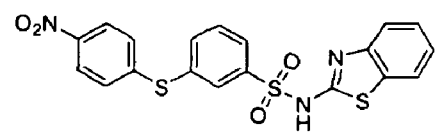
Figure 9E:
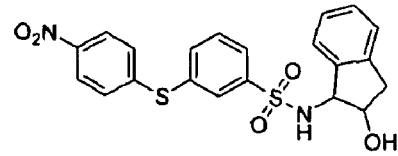
Figure 9E:
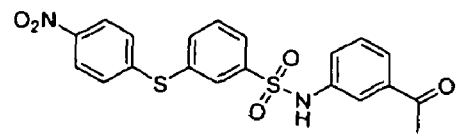
Figure 9F:
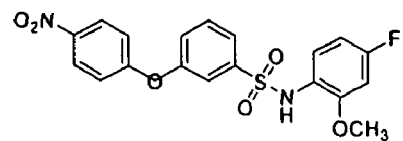
Figure 9F:
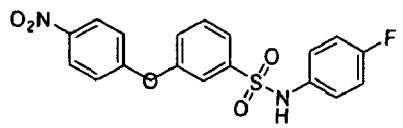
Figure 9F:
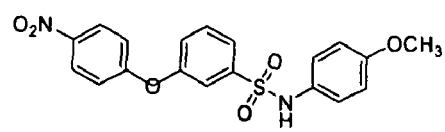
Figure 9F:
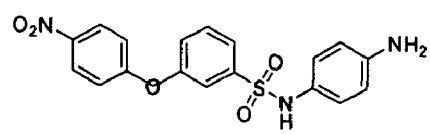
Figure 9F:
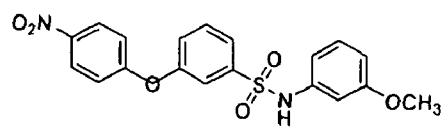
Figure 9F:
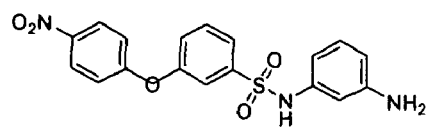
Figure 9F:
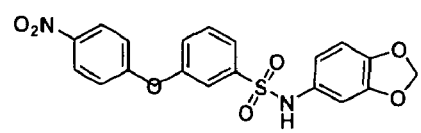
Figure 9F:
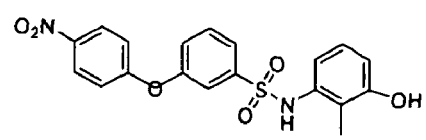
Figure 9G:
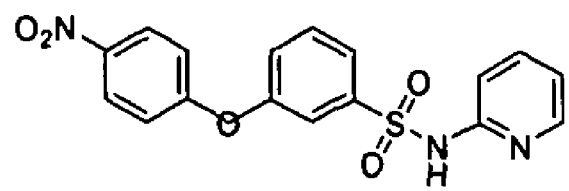
Figure 9G:
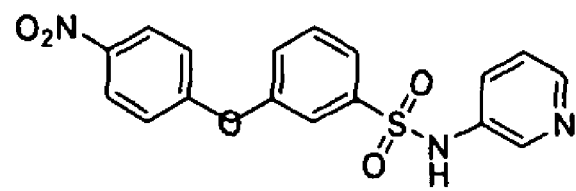
Figure 9G:
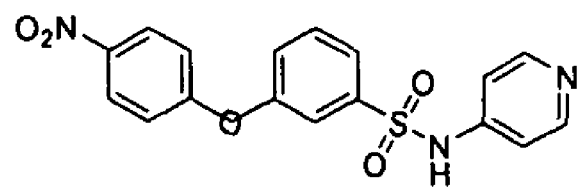
Figure 9G:
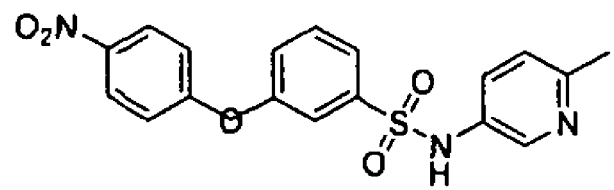

The compounds described herein can be used as inhibitors of Vif involved in viral, e.g., HIV, replication. These inhibitors of protein function generally also affect the cellular levels of a second protein. In some embodiments, the first protein is Vif and the second protein is APOBEC3G and/or APOBEC3F.

Methods of Identifying Virion Infectivity Factor (Vif) Inhibitors

As described herein, Vif counteracts the antiviral activity of APOBEC3G and/or APOBEC3F at least in part by reducing the amount of APOBEC3G and/or APOBEC3F protein normally present or synthesized in cells. With less APOBEC3G and/or APOBEC3F protein made or present, less APOBEC3G and/or APOBEC3F protein is packaged into new viruses, and fewer viruses are affected by APOBEC3G and/or APOBEC3F mutating activity during the next round of infection. Based on this information, the present invention relates to screening methods for isolating compounds such as small molecules that inhibit Vif. Using these methods, we have identified small molecules that block Vif function. Blocking Vif function with these molecules restores normal levels of protein synthesis in cells, including synthesis of APOBEC3G and/or APOBEC3F and other potential host defense proteins, thereby restoring or enhancing the host response to viral infection. Thus, in one aspect, the present invention provides methods of identifying inhibitors, e.g., small molecule inhibitors, of Vif function, and the inhibitors identified thereby.

In one embodiment of the screening methods, 293T cells expressing a Vif fusion protein comprised of Vif linked to a first reporter group, e.g., a fluorescent protein (e.g., an easily detectable protein; in some embodiments, this protein is the Yellow-Fluorescent Protein (YFP)) are observed, as are cells that synthesize a second fluorescent protein (e.g., another easily detectable protein, Cyan Fluorescent Protein (CFP)) linked to APOBEC3G and/or APOBEC3F. In addition, some cells that concomitantly synthesize both YFP-Vif and either or both of CFP-APOBEC3G and/or CFP-APOBEC3F are observed, e.g., in the presence or absence of a candidate inhibitor.

To assay whether the first and second fusion proteins are being synthesized in the screen, YFP-Vif and either or both of CFP-APOBEC3G and/or CFP-APOBEC3F fluorescence is measured using a fluorimeter. In cells lacking YFP-Vif, a high level of CFP fluorescence is easily detectable. However, in cells synthesizing YFP-Vif, CFP fluorescence is dramatically reduced, indicating that YFP-Vif negatively affects the synthesis of the CFP-linked APOBEC3G and/or APOBEC3F. In one embodiment comprising a high throughput screen (HTS), cells grown in a multiwell, e.g., 96 well, plate format are treated with an array of test compounds, e.g., synthetic small molecule libraries, and assayed for restoration of CFP fluorescence in the presence of sustained YFP fluorescence. Any test compounds that leads to the restoration of CFP fluorescence in the presence of YFP-Vif is expected to have blocked Vif function. These compounds are then considered "hits" (or "candidate compounds") and can then be further evaluated for their potential as anti-viral agents, e.g., anti-HIV-1 drugs.

As used herein, a "test compound" can be any chemical compound, for example, a macromolecule (e.g., a polypeptide, a protein complex, glycoprotein, or a nucleic acid) or a small molecule (e.g., an amino acid, a nucleotide, an organic or inorganic compound). A test compound can have a formula weight of less than about 100,000 grams per mole, less than about 50,000 grams per mole, less than about 10,000 grams per mole, less than 5,000 grams per mole, less than 1,000 grams per mole, or less than about 500 grams per mole. The test compound can be naturally occurring (e.g., an herb or a natural product), synthetic, or can include both natural and synthetic components. Examples of test compounds include proteins, peptides, peptidomimetics (e.g., peptoids), amino acids, amino acid analogs, polynucleotides, polynucleotide analogs, nucleotides, nucleotide analogs, and organic or inorganic compounds, e.g., heteroorganic or organometallic compounds.

Vif inhibitors can be identified, e.g., from a library of small molecules, using the screening methods described herein, in U.S. patent application Ser. No. 10/984,946, published as U.S. Pat. App. Pub. No. 2005/0123906, and in Wichroski et al., J. Biol. Chem. 2005, 280(9), 8387-8396, which are incorporated herein by reference in their entirety.

Vif Inhibitors

The invention includes Vif inhibitors identified by the screening methods described herein.

Figure 10B:
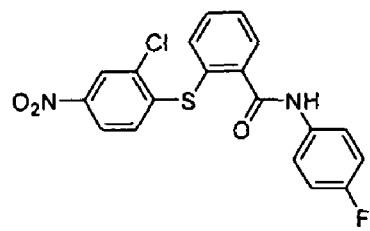
Figure 10B:
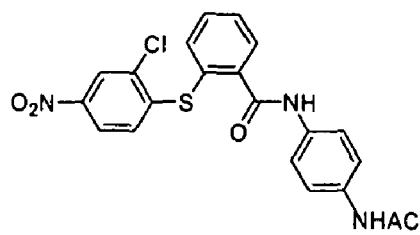
Figure 10B:
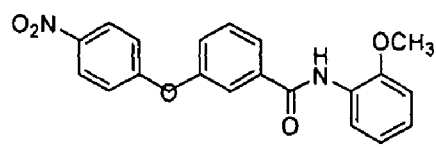
Figure 10B:
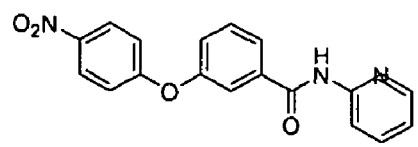
Figure 10B:
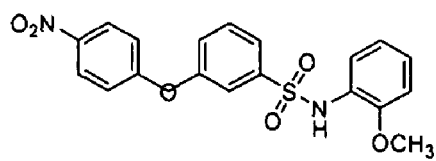

In some embodiments, a Vif inhibitor has Formula I:

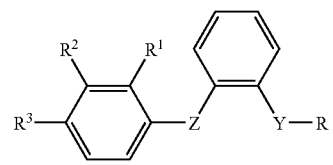

wherein:

R is H, $C_{1-6}$ alkyl, $C_{2-6}$ alkenyl, $C_{2-6}$ alkynyl, aryl, heteroaryl, cycloalkyl, or heterocycloalkyl, wherein said $C_{1-6}$ alkyl, $C_{2-6}$ alkenyl, $C_{2-6}$ alkynyl, aryl, heteroaryl, cycloalkyl, or heterocycloalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, aryl, heteroaryl, cycloalkyl, heterocycloalkyl, heteroarylalkyl, cycloalkyl, heterocycloalkyl, CN, $NO_2$, $OR^a$, —($C_{1-4}$ alkyl)-$OR^a$, $SR^a$, —($C_{1-4}$ alkyl)-$SR^a$, $C(O)R^b$, —($C_{1-4}$ alkyl)-$C(O)R^b$, $C(O)NR^cR^d$, —($C_{1-4}$ alkyl)-$C(O)NR^cR^d$, $C(O)OR^a$, —($C_{1-4}$ alkyl)-$C(O)OR^a$, $OC(O)R^b$, —($C_{1-4}$ alkyl)-$OC(O)R^b$, $OC(O)NR^cR^d$, —($C_{1-4}$ alkyl)-$OC(O)NR^cR^d$, $NR^cR^d$, $NR^cC(O)R^b$, —($C_{1-4}$ alkyl)-$NR^cCOR^b$, $NR^cC(O)NR^cR^d$, —($C_{1-4}$ alkyl)-$NR^cC(O)NR^cR^d$, $NR^cC(O)OR^a$, —($C_{1-4}$ alkyl)-$NR^cC(O)OR^a$, $C(=NR^i)NR^cR^d$, $NR^cC(=NR^i)NR^cR^d$, $P(R^f)_2$, $P(OR^e)_2$, $P(O)R^eR^f$, $P(O)OR^eOR^f$, $S(O)R^b$, —($C_{1-4}$ alkyl)-$S(O)R^b$, $S(O)NR^cR^d$, —($C_{1-4}$ alkyl)-$S(O)NR^cR^d$, $S(O)_2R^b$, —($C_{1-4}$ alkyl)-$S(O)_2R^b$, $NR^cS(O)_2R^b$, —($C_{1-4}$ alkyl)-$NR^cS(O)_2R^b$, $S(O)_2NR^cR^d$, and —($C_{1-4}$ alkyl)-$S(O)_2NR^cR^d$;

$R^a$, $R^b$, $R^c$, $R^d$, $R^e$, and $R^f$ are each independently H, $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, 3, 4, or 5 substituents independently selected from OH, amino, halo, $C_{1-6}$ alkyl, aryl, arylalkyl, heteroaryl, heteroarylalkyl, cycloalkyl, or heterocycloalkyl;

$R^g$ is H, $C_{1-10}$ alkyl, $C_{1-10}$ haloalkyl, $C_{2-10}$ alkenyl, or $C_{2-10}$ alkynyl;

$R^1$, $R^2$, and $R^3$ are independently selected from H, $NO_2$, $NH_2$, $CF_3$, Br, Cl, F, and I;

Y is $C(O)$, $NR^gCO$, $SO_2NR^g$, $NR^gSO_2$, $NHC(O)NH$, $N^gC(O)O$, $OC(O)N^g$, or $CONR^g$; and Z is absent, O, S, $NR^g$, $CH_2$, $SO_2$, $C_{1-6}$ alkyl-$OR^g$, CO, $C_{1-6}$ alkyl-$NR^g$;

or an enantiomers, diastereomers, or pharmaceutically acceptable salt thereof, excluding compounds 1, 2, 3, 4, 5, 6, 7, 8, 9 shown in FIGS. 10A-B.

In some embodiments, $R^g$ is H.

In some embodiments, R is H, $C_{1-6}$ alkyl, $C_{2-6}$ alkenyl, $C_{2-6}$ alkynyl, aryl, heteroaryl, cycloalkyl, or heterocycloalkyl, wherein said $C_{1-6}$ alkyl, $C_{2-6}$ alkenyl, $C_{2-6}$ alkynyl, aryl, heteroaryl, cycloalkyl, or heterocycloalkyl is optionally substituted by 1, 2, 3, 4, or 5 substituents independently selected from halo, $C_{-1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, aryl, heteroaryl, cycloalkyl, heterocycloalkyl, heteroarylalkyl, cycloalkyl, heterocycloalkyl, CN, $NO_2$, $OR^a$, —($C_{1-4}$ alkyl)-$OR^a$, $SR^a$, —($C_{1-4}$ alkyl)-$SR^a$, $C(O)R^b$, —($C_{1-4}$ alkyl)-$C(O)R^b$, $C(O)NR^cR^d$, —($C_{1-4}$ alkyl)-$C(O)NR^cR^d$, and $C(O)OR^a$.

In some embodiments, R is H, $C_{1-6}$ alkyl, $C_{2-6}$ alkenyl, $C_{2-6}$ alkynyl, aryl, heteroaryl, cycloalkyl, or heterocycloalkyl, wherein said $C_{1-6}$ alkyl, $C_{2-6}$ alkenyl, $C_{2-6}$ alkynyl, aryl, heteroaryl, cycloalkyl, or heterocycloalkyl is optionally substituted by 1, 2, 3, 4, or 5 substituents independently selected from halo, $C_{1-6}$ alkyl, $C_{2-6}$ alkenyl, $C_{2-6}$ alkynyl, aryl, heteroaryl, cycloalkyl, heterocycloalkyl, heteroarylalkyl, cycloalkyl, heterocycloalkyl, CN, $NO_2$, $OR^a$, —($C_{1-4}$ alkyl)-$OR^1$, $SR^a$, —($C_{1-4}$ alkyl)-$SR^a$, $C(O)R^b$, —($C_{1-4}$ alkyl)-$C(O)R^b$, $C(O)NR^cR^d$, —($C_{1-4}$ alkyl)-$C(O)NR^cR^d$, and $C(O)OR^a$.

In some embodiments, R is H, $C_{1-6}$ alkyl, $C_{2-6}$ alkenyl, $C_{2-6}$ alkynyl, aryl, heteroaryl, cycloalkyl, or heterocycloalkyl, wherein said $C_{1-6}$ alkyl, $C_{2-6}$ alkenyl, $C_{2-6}$ alkynyl, aryl, heteroaryl, cycloalkyl, or heterocycloalkyl is optionally substituted by 1, 2, 3, 4, or 5 substituents independently selected from halo, $C_{1-6}$ alkyl, $C_{2-6}$ alkenyl, $C_{2-6}$ alkynyl, aryl, heteroaryl, cycloalkyl, heterocycloalkyl, heteroarylalkyl, cycloalkyl, heterocycloalkyl, CN, $NO_2$, $OR^a$, $SR^a$, $C(O)R^b$, $C(O)NR^cR^d$, and $C(O)OR^a$.

In some embodiments, a Vif inhibitor has a Formula I, wherein:

R is alkyl, aryl, heterocyclyl, or heteroaryl, each optionally substituted with 1, 2, 3, 4, or 5 substituents independently selected from OH, amino, halo, $C_{1-6}$ alkyl, O—$C_{1-6}$ alkyl, aryl, arylalkyl, heteroaryl, heteroarylalkyl, cycloalkyl, and heterocycloalkyl;

$R^1$, $R^2$, and $R^3$ are independently selected from H, $NO_2$, $NH_2$, $CF_3$, Br, Cl, F, and I;

Y is NHCO or CONH; and

Z is O, S, or NH;

or an enantiomer, diastereomer, or pharmaceutically acceptable salt thereof, excluding compounds 1, 2, 3, 4, 5, 6, 7, 8, and 9 shown in FIGS. 10A-B.

In some embodiments, a Vif inhibitor has a Formula I wherein:

R is alkyl, aryl, heterocyclyl, or heteroaryl;

$R^1$, $R^2$, and $R^3$ are independently selected from H, $NO_2$, $NH_2$, $CF_3$, Br, Cl, F, and I;

Y is NHCO, or CONH;

Z is O, S, or NH; and enantiomers, diastereomers, and pharmaceutically acceptable salts thereof, excluding compounds 1, 2, 3, 4, 5, 6, 7, 8, and 9 shown in FIGS. 10A-B, which are examples of compounds in formula I that are known, but their use as Vif inhibitors was not known.

In some embodiments, a Vif inhibitor has Formula II:

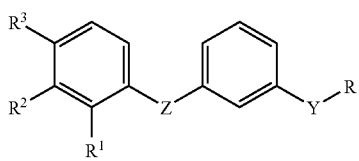

II wherein:

R is H, $C_{1-6}$ alkyl, $C_{2-6}$ alkenyl, $C_{2-6}$ alkynyl, aryl, heteroaryl, cycloalkyl, or heterocycloalkyl, wherein said $C_{1-6}$ alkyl, $C_{2-6}$ alkenyl, $C_{2-6}$ alkynyl, aryl, heteroaryl, cycloalkyl, or heterocycloalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, aryl, heteroaryl, cycloalkyl, heterocycloalkyl, heteroarylalkyl, cycloalkyl, heterocycloalkyl, CN, $NO_2$, $OR^a$, —($C_{1-4}$ alkyl)-$OR^a$, $SR^a$, —($C_{1-4}$ alkyl)-$SR^a$, $C(O)R^b$, —($C_{1-4}$ alkyl)-$C(O)R^b$, $C(O)NR^cR^d$, —($C_{1-4}$ alkyl)-$C(O)NR^cR^d$, $C(O)OR^a$, —($C_{1-4}$ alkyl)-$C(O)OR^a$, $OC(O)R^b$, —$C_{1-4}$ alkyl)-$OC(O)R^b$, $OC(O)NR^cR^d$, —($C_{1-4}$ alkyl)-$OC(O)NR^cR^d$, $NR^cR^d$, $NR^cC(O)R^b$, —($C_{1-4}$ alkyl)-$NR^cCOR^b$, $NR^cC(O)NR^cR^d$, —($C_{1-4}$ alkyl)-$NR^cC(O)NR^cR^d$, $NR^cC(O)OR^a$, —($C_{1-4}$ alkyl)-$NR^cC(O)OR^a$, $C(=NR^i)NR^cR^d$, $NR^cC(=NR^i)NR^cR^d$, $P(R^f)_2$, $P(OR^e)_2$, $P(O)R^eR^f$, $P(O)OR^eOR^f$, $S(O)R^b$, —($C_{1-4}$ alkyl)-$S(O)R^b$, $S(O)NR^cR^d$, —($C_{1-4}$ alkyl)-$S(O)NR^cR^d$, $S(O)_2R^b$, —($C_{1-4}$ alkyl)-$S(O)_2R^b$, $NR^cS(O)_2R^b$, —($C_{1-4}$ alkyl)-$NR^cS(O)_2R^b$, $S(O)_2NR^cR^d$, and —$C_{1-4}$ alkyl)-$S(O)_2NR^cR^d$;

$R^a$, $R^b$, $R^c$, $R^d$, $R^e$, and $R^f$ are each independently H, $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, 3, 4, or 5 substituents independently selected from OH, amino, halo, $C_{1-6}$ alkyl, aryl, arylalkyl, heteroaryl, heteroarylalkyl, cycloalkyl, or heterocycloalkyl;

$R^g$ is H, $C_{1-10}$ alkyl, $C_{1-10}$ haloalkyl, $C_{2-10}$ alkenyl, or $C_{2-10}$ alkynyl;

$R^1$, $R^2$, and $R^3$ are independently selected from H, $NO_2$, $NH_2$, $CF_3$, Br, Cl, F, and I;

Y is $C(O)$, $NR^gCO$, $SO_2NR^g$, $NR^gSO_2$, $NHC(O)NH$, $NHC(O)O$, $OC(O)NH$, or $CONR^g$; and Z is absent, O, S, $NR^g$, $CH_2$, $SO_2$, $C_{1-6}$ alkyl-$OR^g$, CO, $C_{1-6}$ alkyl-$NR^g$;

or an enantiomer, diastereomer or pharmaceutically acceptable salt thereof, excluding compounds 10, 11, 12 shown in FIGS. 10A-B.

In some embodiments, $R^g$ is H.

In some embodiments, R is H, $C_{1-6}$ alkyl, $C_{2-6}$ alkenyl, $C_{2-6}$ alkynyl, aryl, heteroaryl, cycloalkyl, or heterocycloalkyl, wherein said $C_{1-6}$ alkyl, $C_{2-6}$ alkenyl, $C_{2-6}$ alkynyl, aryl, heteroaryl, cycloalkyl, or heterocycloalkyl is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, aryl, heteroaryl, cycloalkyl, heterocycloalkyl, heteroarylalkyl, cycloalkyl, heterocycloalkyl, CN, $NO_2$, $OR^a$, —($C_{1-4}$ alkyl)-$OR^a$, $SR^a$, —($C_{1-4}$ alkyl)-$SR^a$, $C(O)R^b$, —($C_{1-4}$ alkyl)-$C(O)R^b$, $C(O)NR^cR^d$, —($C_{1-4}$ alkyl)-$C(O)NR^cR^d$, $C(O)OR^a$.

In some embodiments, R is H, $C_{1-6}$ alkyl, $C_{2-6}$ alkenyl, $C_{2-6}$ alkynyl, aryl, heteroaryl, cycloalkyl, or heterocycloalkyl, wherein said $C_{1-6}$ alkyl, $C_{2-6}$ alkenyl, $C_{2-6}$ alkynyl, aryl, heteroaryl, cycloalkyl, or heterocycloalkyl is optionally substituted by 1, 2, 3, 4, or 5 substituents independently selected from halo, $C_{1-6}$ alkyl, $C_{2-6}$ alkenyl, $C_{2-6}$ alkynyl, aryl, heteroaryl, cycloalkyl, heterocycloalkyl, heteroarylalkyl, cycloalkyl, heterocycloalkyl, CN, $NO_2$, $OR^a$, —($C_{1-4}$ alkyl)-$OR^a$, $SR^a$, —($C_{1-4}$ alkyl)-$SR^a$, $C(O)R^b$, —($C_{1-4}$ alkyl)-$C(O)R^b$, $C(O)NR^cR^d$, —($C_{1-4}$ alkyl)-$C(O)NR^cR^d$, $C(O)OR^a$.

In some embodiments, R is H, $C_{1-6}$ alkyl, $C_{2-6}$ alkenyl, $C_{2-6}$ alkynyl, aryl, heteroaryl, cycloalkyl, or heterocycloalkyl, wherein said $C_{1-6}$ alkyl, $C_{2-6}$ alkenyl, $C_{2-6}$ alkynyl, aryl, heteroaryl, cycloalkyl, or heterocycloalkyl is optionally substituted by 1, 2, 3, 4, or 5 substituents independently selected from halo, $C_{1-6}$ alkyl, $C_{2-6}$ alkenyl, $C_{2-6}$ alkynyl, aryl, heteroaryl, cycloalkyl, heterocycloalkyl, heteroarylalkyl, cycloalkyl, heterocycloalkyl, CN, $NO_2$, $OR^a$, $SR^a$, $C(O)R^b$, $C(O)NR^cR^d$, $C(O)OR^a$.

In some embodiments, a Vif inhibitor has a Formula II, wherein:

R is alkyl, aryl, heterocyclyl, or heteroaryl, each optionally substituted with 1, 2, 3, 4, or 5 substituents independently selected from OH, amino, halo, $C_{1-6}$ alkyl, O—$C_{1-6}$ alkyl, aryl, arylalkyl, heteroaryl, heteroarylalkyl, cycloalkyl, and heterocycloalkyl;

$R^1$, $R^2$, and $R^3$ are independently selected from H, $NO_2$, $NH_2$, $CF_3$, Br, Cl, F, and I;

Y is NHCO or CONH;

Z is O, S, or NH;

or an enantiomer, diastereomer or pharmaceutically acceptable salt thereof, excluding compounds 10, 11, 12 shown in FIGS. 10A-B.

In some embodiments, a Vif inhibitor has the Formula II, wherein:

R is alkyl, aryl, heterocyclyl, or heteroaryl;

$R^1$, $R^2$, and $R^3$ are independently selected from H, $NO_2$, $NH_2$, $CF_3$, Br, Cl, F, and I;

Y is NHCO or CONH;

Z is O, S, or NH; and enantiomers, diastereomers, and pharmaceutically acceptably salts thereof, excluding compounds 10 to 12 shown in FIGS. 10A-B, which are three examples of compounds in Formula II that are known, but their use as Vif inhibitors was not known.

The Vif inhibitors also include compounds in Formulas III-V (illustrated below) and enantiomers, diastereomers, and pharmaceutically acceptable salts of these compounds.

For example, in some embodiments, a Vif inhibitor has the Formula III:

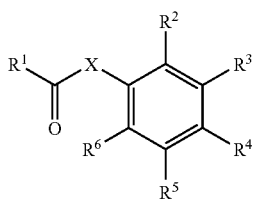

wherein:

X is O or NH;

$R^1$ is —$CH_3$,

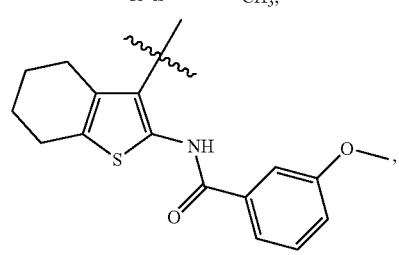

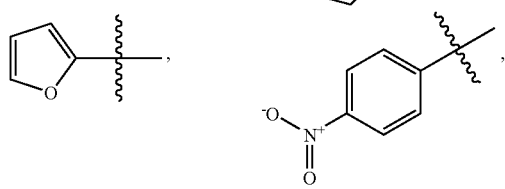

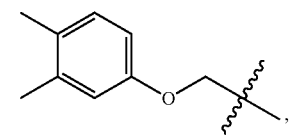

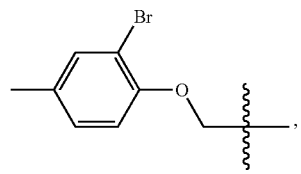

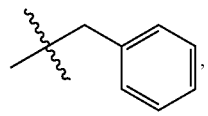

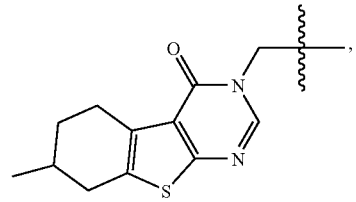

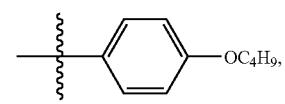

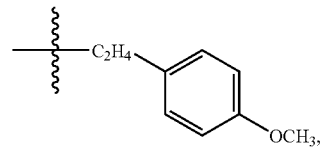

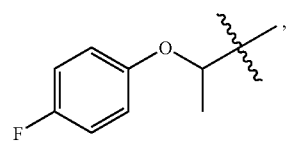

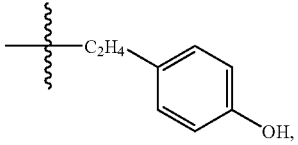

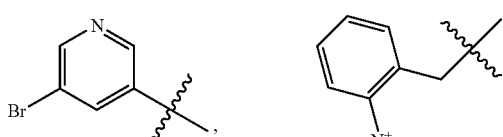

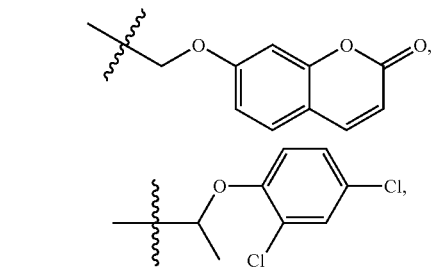

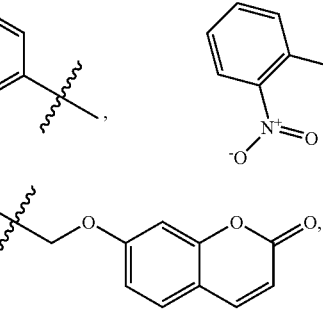

-continued
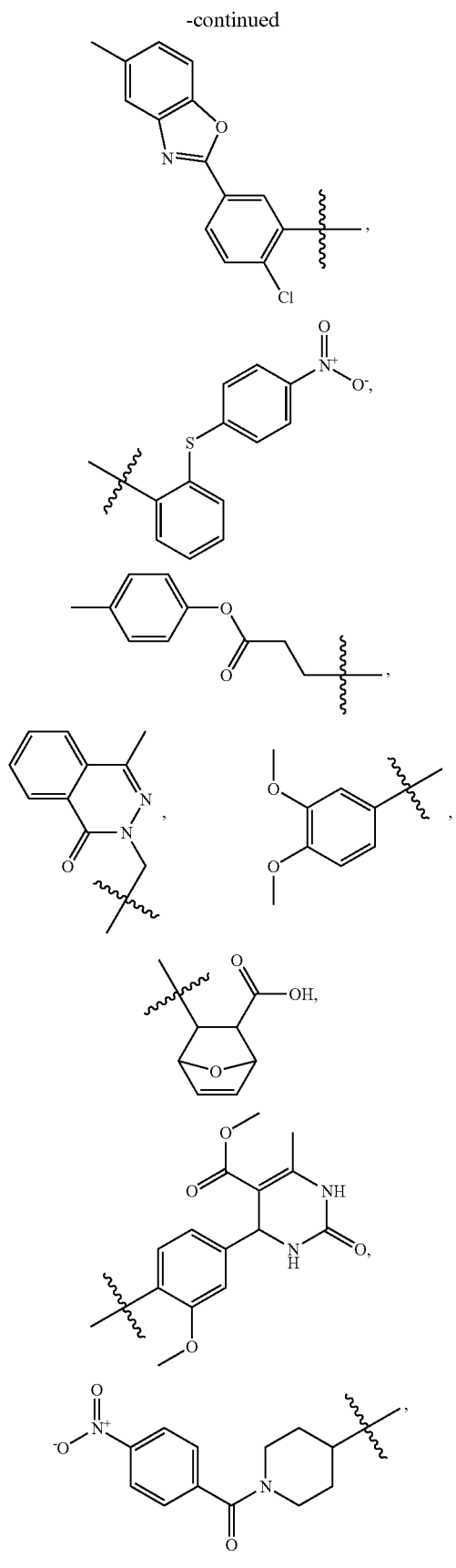
-continued
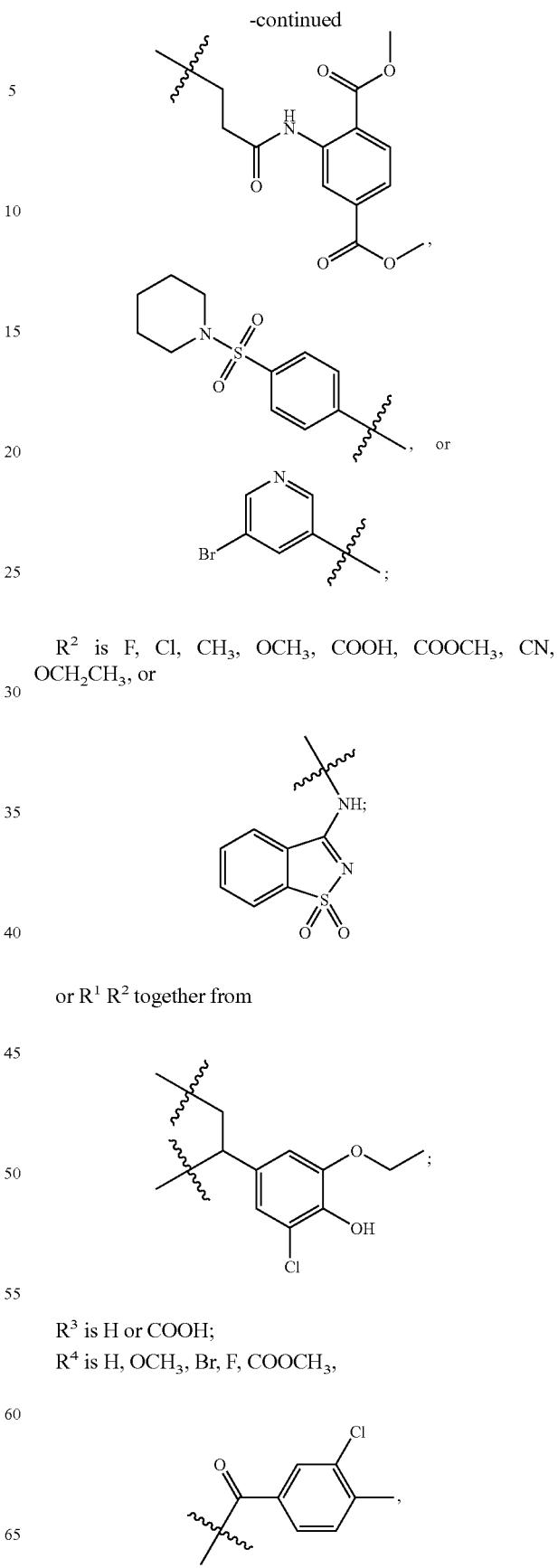
$R^2$ is F, Cl, $CH_3$, $OCH_3$, COOH, $COOCH_3$, CN, $OCH_2CH_3$, or
or $R^1$ $R^2$ together from
$R^3$ is H or COOH;
$R^4$ is H, $OCH_3$, Br, F, $COOCH_3$, -continued
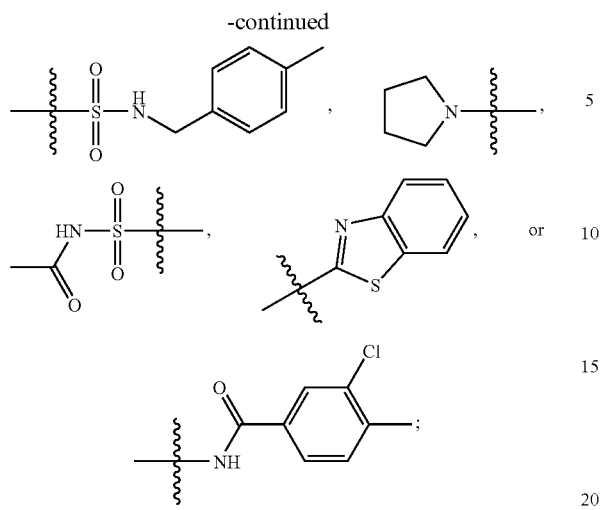
or R³ and R⁴ together form
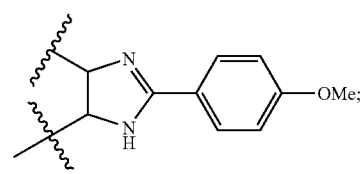
R⁵ is H, NO₂, COOCH₃, benzo[d]thiazol-2-yl, and SO₂N(C₂H₅)₂;
R⁶ is H;
or R⁵ and R⁶ together form
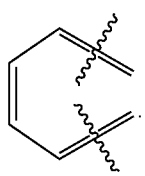
As another example, in some embodiments, a Vif inhibitor has the Formula IV:
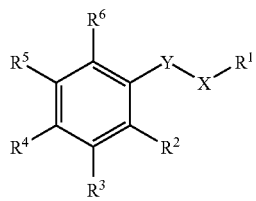
IV
wherein:
X is O or NR⁷;
Y is C=O, or SO₂;
R¹ is H, CH₃,
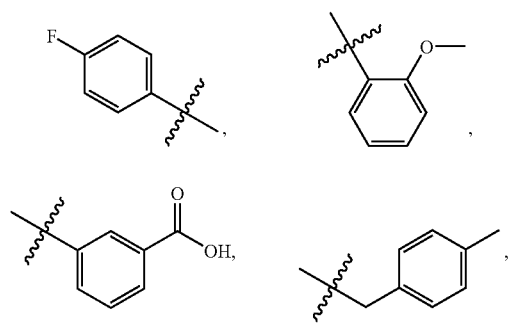
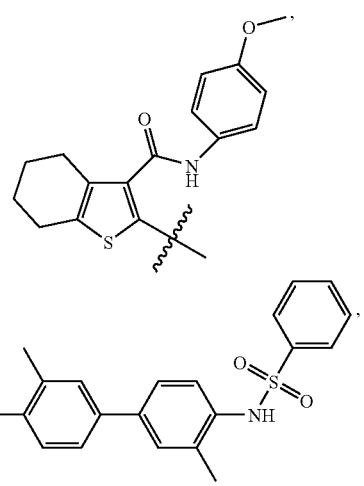

-continued
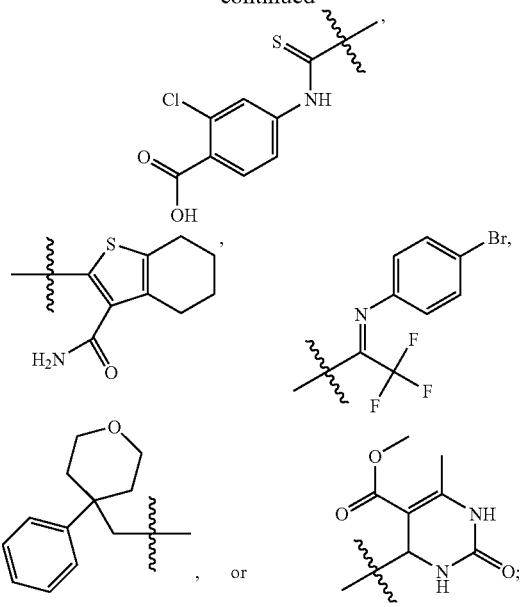
or R[1] and R[7] together form
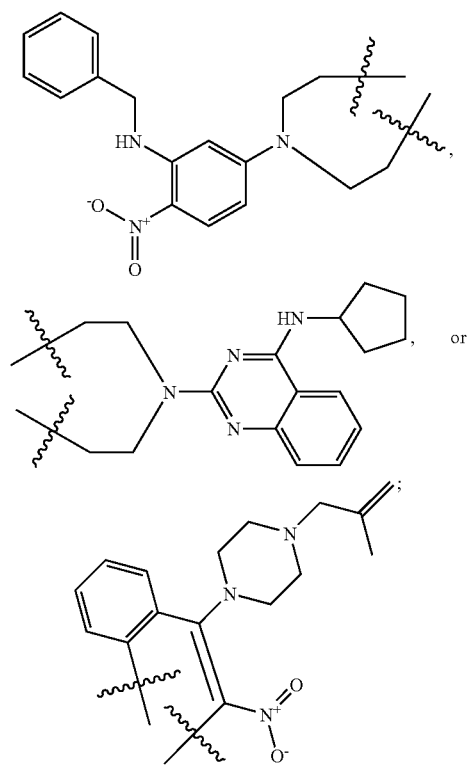
R[2] is H, Cl, I, or S-(4-nitrophenyl);
R[3] is H, F, Cl, Br, I, OCH₃, OCH₂CH₃;
R[4] is H, CH₃, OCH₂CH₃, NHC(O)CH3, or S(O)₂-piperidine;
or R[3] and R[4] together form OCH₂O;
R[5] is H or Cl;
R[6] is H; and
R[7] is H or CH₃.
For example, in some embodiments, a Vif inhibitor has the Formula V:
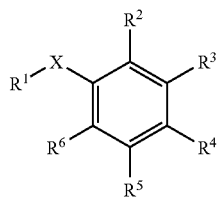
wherein:
X is S or O;
R[1] is H, CH₃, OCH₃, CH₂CH=CH₂, C₄H₉, CH₂C(O)NHCH₂CH₂OH, CH₂CH₂NHCH₂CH=CH₂, CH₂CH₂(N-morpholine),
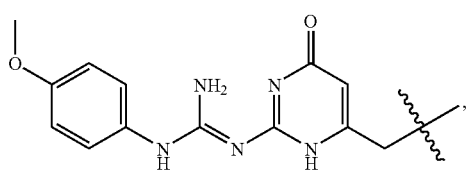
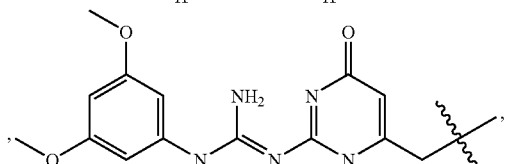
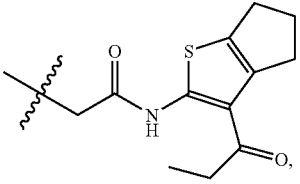
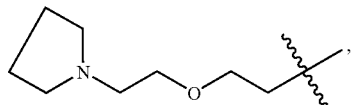
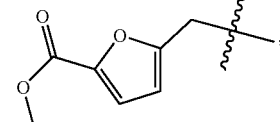
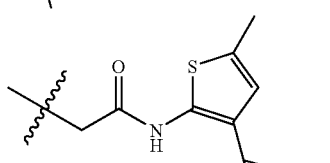
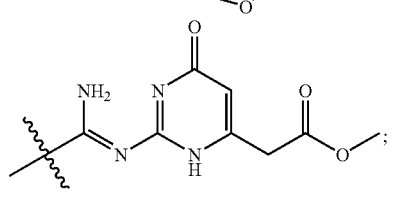

$R^2$ is H, $CH_3$, Cl, $OCH_3$, CH(phenyl)$CH_2$COOH, or CH($CH_3$)$CH_2CH_3$;

or $R_1$ and $R_2$ together form

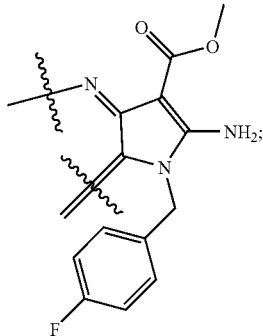

$R^3$ is H;
$R^4$ is H, Br, Cl, $CH_3$, CH(OH)$CH_2CH_3$,

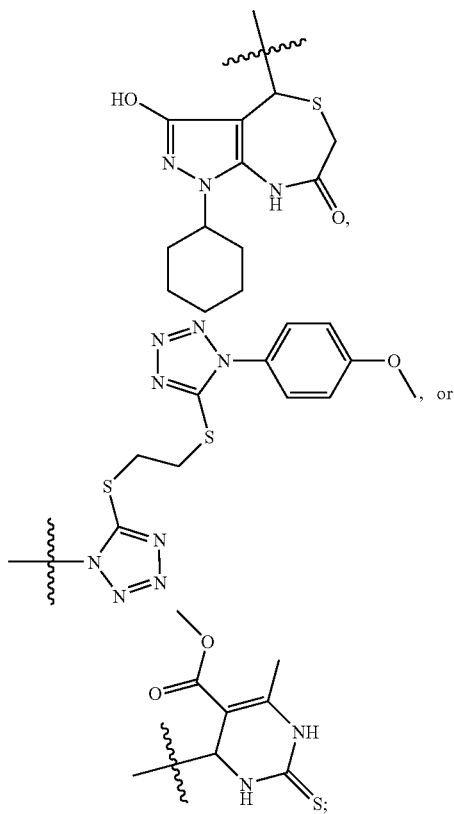, or

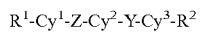

$R^5$ is H, and
$R^6$ is H or $CH_2CH=CH_2$.

In some embodiments, a Vif inhibitor has Formula VI:

$$R^1\text{-}Cy^1\text{-}Z\text{-}Cy^2\text{-}Y\text{-}Cy^3\text{-}R^2 \qquad \text{VI}$$

wherein:
$R^1$ is H, halo, $C_{1-6}$ alkyl, $C_{1-6}$ haloalkyl, $C_{2-6}$ alkenyl, $C_{2-6}$ alkynyl, $Cy^{a1}$, $SO_2NR^{c1}R^{d1}$, $NHSO_2$—$C_{1-6}$ alkyl, $C_{1-6}$ cyanoalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{i})NR^{c1}R^{d1}$, $NR^{c1}C(=NR^{i})NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, $S(O)NR^{c1}R^{d1}$, $S(O)_2R^{b1}$, $NR^{c1}S(O)_2R^{b1}$, $S(O)_2NR^{c1}R^{d1}$, $Cy^{a1}$, or $Cy^{a1}$-($C_{1-6}$ alkyl)-, wherein said $C_{1-6}$ alkyl, $C_{2-6}$ alkenyl, or $C_{2-6}$ alkynyl, is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}(O)R^{b1}$, $NR^{c1}C(O)NR^{c1}R^{d1}$, $NR^{c1}C(O)OR^{a1}$, $C(=NR^{i1})NR^{c1}R^{d1}$, $NR^{c1}C(=NR^{i1})NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

Z is absent, O, S, $NR^{g1}$, $CH_2$, $SO_2$, $CH(OR^{g1})$, CO, $CH(NR^{g1})$, $C_{1-6}$ alkyl-O, $C_{2-6}$ alkenyl-O, $C_{2-6}$ alkynyl-O, $C_{1-6}$ alkyl-S, $C_{2-6}$ alkenyl-S, $C_{2-6}$ alkynyl-S, $C_{1-6}$ alkyl-$NR^{g1}$, $C_{2-6}$ alkenyl-$NR^{g1}$, $C_{2-6}$ alkynyl-$NR^{g1}$, $C_{1-6}$ alkyl-$SO_2$, $C_{2-6}$ alkenyl-$SO_2$, $C_{2-6}$ alkynyl-$SO_2$, $SO_2NR^{g1}$, Y is C(O), $NR^{g2}$CO, $SO_2NR^{g2}$, $NR^{g2}SO_2$, NHC(O)NH, NHC(O)O, OC(O)NH, or $CONR^{g2}$;

$R^2$ is H, halo, $C_{1-6}$ alkyl, $C_{1-6}$ haloalkyl, $C_{2-6}$ alkenyl, $C_{2-6}$ alkynyl, $Cy^{a2}$, $SO_2NR^{c2}R^{d2}$, $NHSO_2$—$C_{1-6}$ alkyl, $C_{1-6}$ cyanoalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{i1})NR^{c2}R^{d2}$, $NR^{c2}C(=NR^{i1})NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$, $S(O)_2R^{b2}$, $NR^{c2}S(O)_2R^{b2}$, $S(O)_2NR^{c2}R^{d2}$, $Cy^{a1}$, or $Cy^{a1}$-($C_{1-6}$ alkyl)-, wherein said $C_{1-6}$ alkyl, $C_{2-6}$ alkenyl, or $C_{2-6}$ alkynyl, is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{i2})NR^{c2}R^{d2}$, $NR^{c2}C(=NR^{i2})NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$Cy^1$ is aryl, heteroaryl, cycloalkyl, or heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $C(=NR^{i3})NR^{c3}R^{d3}$, $NR^{c3}C(=NR^{i3})NR^{c3}R^{d3}$, $P(R^{f3})_2$, $P(OR^{e3})_2$, $P(O)R^{e3}R^{f3}$, $P(O)OR^{e3}OR^{f3}$, $S(O)R^{b3}$, $S(O)NR^{c3}R^{d3}$, $S(O)_2R^{b3}$, and $S(O)_2NR^{c3}R^{d3}$;

$Cy^2$ is aryl, heteroaryl, cycloalkyl, or heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $C(=NR^{i4})NR^{c4}R^{d4}$, $NR^{c4}C(=NR^{i4})NR^{c4}R^{d4}$, $P(R^{f4})_2$, $P(OR^{e4})_2$, $P(O)R^{e4}R^{f4}$, $P(O)OR^{e4}OR^{f4}$, $S(O)R^{b4}$, $S(O)NR^{c4}R^{d4}$, $S(O)_2R^{b4}$, and $S(O)_2NR^{c4}R^{d4}$;

$Cy^3$ is aryl, heteroaryl, cycloalkyl, or heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $C(=NR^{i5})NR^{c5}R^{d5}$, $NR^{c5}C(=NR^{i5})NR^{c5}R^{d5}$, $P(R^{f5})_2$, $P(OR^{e5})_2$, $P(O)R^{e5}R^{f5}$, $P(O)OR^{e5}OR^{f5}$, $S(O)R^{b5}$, $S(O)NR^{c5}R^{d5}$, $S(O)_2R^{b5}$, and $S(O)_2NR^{c5}R^{d5}$;

$Cy^{a1}$, $Cy^{a2}$ are independently selected from aryl, heteroaryl, cycloalkyl, and heterocycloalkyl, each optionally substituted by 1, 2, 3 or 4 substituents independently selected from halo, $C_{1-4}$ alkyl, $C_{2-4}$ alkenyl, $C_{2-4}$ alkynyl, $C_{1-4}$ haloalkyl, CN, NO$_2$, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)OR$^{a6}$, C(=NR$^{i6}$)NR$^{c6}$R$^{d6}$, NR$^{c6}$C(=NR$^{i6}$)NR$^{c6}$R$^{d6}$, P(R$^{f6}$)$_2$, P(OR$^{e6}$)$_2$, P(O)R$^{e6}$R$^{f6}$, P(O)OR$^{e6}$OR$^{f6}$, S(O)R$^{b6}$, S(O)NR$^{c6}$R$^{d6}$, S(O)$_2$R$^{b6}$, and S(O)$_2$NR$^{c6}$R$^{d6}$;

R$^{a1}$, R$^{a2}$, R$^{a3}$, R$^{a4}$, R$^{a5}$, R$^{a6}$, R$^{b1}$, R$^{b2}$, R$^{b3}$, R$^{b4}$, R$^{b5}$, R$^{b6}$, R$^{c1}$, R$^{c2}$, R$^{c3}$, R$^{c4}$, R$^{c5}$, R$^{c6}$, R$^{d1}$, R$^{d2}$, R$^{d3}$, R$^{d4}$, R$^{d5}$, R$^{d6}$R$^{e1}$, R$^{e2}$, R$^{e3}$, R$^{e4}$, R$^{e5}$, R$^{e6}$, R$^{f1}$, R$^{f2}$, R$^{f3}$, R$^{f4}$, R$^{f5}$, and R$^{f6}$ are independently selected from H, $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, 3, 4, or 5 substituents independently selected from OH, amino, halo, $C_{1-6}$ alkyl, aryl, arylalkyl, heteroaryl, heteroarylalkyl, cycloalkyl, and heterocycloalkyl;

R$^{g1}$ and R$^{g2}$ are independently selected from H, $C_{1-10}$ alkyl, $C_{1-10}$ haloalkyl, $C_{2-10}$ alkenyl, and $C_{2-10}$ alkynyl; and R$^i$ is H, $C_{1-10}$ alkyl, $C_{1-10}$ haloalkyl, $C_{2-10}$ alkenyl, or $C_{2-10}$ alkynyl;

or an enantiomer, diastereomer or pharmaceutically acceptable salt thereof, excluding compounds 1, 2, 3, 4, 5, 6, 7, 8, 9, 10, 11, 12 shown in FIGS. 10A-B.

In some embodiments, one or more of Cy$^1$, Cy$^2$, and Cy$^3$ is phenyl.

In some embodiments, Cy$^1$ and Cy$^2$, or Cy$^2$ and Cy$^3$, or Cy$^1$ and Cy$^3$ are phenyl.

In some embodiments, Cy$^1$ is aryl, heteroaryl, cycloalkyl, or heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, and NR$^{c3}$C(O)OR$^{a3}$.

In some embodiments, Cy$^1$ is aryl, heteroaryl, cycloalkyl, or heterocycloalkyl, each optionally substituted by 1, 2, 3, 4 or 5 substituents independently selected from halo, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, and NR$^{c3}$C(O)OR$^{a3}$.

In some embodiments, Cy$^1$ is aryl, heteroaryl, cycloalkyl, or heterocycloalkyl, each optionally substituted by 1, 2, 3, 4 or 5 substituents independently selected from halo, CN, NO$_2$, OR$^{a3}$, SR$^{a3}$, and NR$^{c3}$R$^{d3}$.

In some embodiments, Cy$^2$ is aryl, heteroaryl, cycloalkyl, or heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, and NR$^{c4}$C(O)OR$^{a4}$.

In some embodiments, Cy$^2$ is aryl, heteroaryl, cycloalkyl, or heterocycloalkyl, each optionally substituted by 1, 2, 3, 4 or 5 substituents independently selected from halo, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, and NR$^{c4}$C(O)OR$^{a4}$.

In some embodiments, Cy$^2$ is aryl, heteroaryl, cycloalkyl, or heterocycloalkyl, each optionally substituted by 1, 2, 3, 4 or 5 substituents independently selected from halo, CN, NO$_2$, OR$^{a4}$, SR$^{a4}$, and NR$^{c4}$R$^{d4}$.

In some embodiments, Cy$^3$ is aryl, heteroaryl, cycloalkyl, or heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, and NR$^{c5}$C(O)OR$^{a5}$.

In some embodiments, Cy$^3$ is aryl, heteroaryl, cycloalkyl, or heterocycloalkyl, each optionally substituted by 1, 2, 3, 4 or 5 substituents independently selected from halo, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$, NR$^{c5}$C(O)R$^{b1}$, and NR$^{c5}$C(O)OR$^{a5}$.

In some embodiments, Cy$^3$ is aryl, heteroaryl, cycloalkyl, or heterocycloalkyl, each optionally substituted by 1, 2, 3, 4 or 5 substituents independently selected from halo, CN, NO$_2$, OR$^{a5}$, SR$^{a5}$, and NR$^{c5}$R$^{d5}$.

In some embodiments, Cy$^1$ is aryl, heteroaryl, or cycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, C(=NR$^{i3}$)NR$^{c3}$R$^{d3}$, NR$^{c3}$C(=NR$^{i3}$)NR$^{c3}$R$^{d3}$, P(R$^{f3}$)$_2$, P(OR$^{e3}$)$_2$, P(O)R$^{e3}$R$^{f3}$, P(O)OR$^{e3}$OR$^{f3}$, S(O)R$^{b3}$, S(O)NR$^{c3}$R$^{d3}$, S(O)$_2$R$^{b3}$, and S(O)$_2$NR$^{c3}$R$^{d3}$.

In some embodiments, Cy$^1$ is aryl, or heteroaryl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, C(=NR$^{i3}$)NR$^{c3}$R$^{d3}$, NR$^{c3}$C(=NR$^{i3}$)NR$^{c3}$R$^{d3}$, P(R$^{f3}$)$_2$, P(OR$^{e3}$)$_2$, P(O)R$^{e3}$R$^{f3}$, P(O)OR$^{e3}$OR$^{f3}$, S(O)R$^{b3}$, S(O)NR$^{c3}$R$^{d3}$, S(O)$_2$R$^{b3}$, and S(O)$_2$NR$^{c3}$R$^{d3}$.

In some embodiments, Cy$^1$ is aryl, or cycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, C(=NR$^{i3}$)NR$^{c3}$R$^{d3}$, NR$^{c3}$C(=NR$^{i3}$)NR$^{c3}$R$^{d3}$, P(R$^{f3}$)$_2$, P(OR$^{e3}$)$_2$, P(O)R$^{e3}$R$^{f3}$, P(O)OR$^{e3}$OR$^{f3}$, S(O)R$^{b3}$, S(O)NR$^{c3}$R$^{d3}$, S(O)$_2$R$^{b3}$, and S(O)$_2$NR$^{c3}$R$^{d3}$.

In some embodiments, Cy$^1$ is aryl optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, C(=NR$^{i3}$)NR$^{c3}$R$^{d3}$, NR$^{c3}$C(=NR$^{i3}$)NR$^{c3}$R$^{d3}$, P(R$^{f3}$)$_2$, P(OR$^{e3}$)$_2$, P(O)R$^{e3}$R$^{f3}$, P(O)OR$^{e3}$OR$^{f3}$, S(O)R$^{b3}$, S(O)NR$^{c3}$R$^{d3}$, S(O)$_2$R$^{b3}$, and S(O)$_2$NR$^{c3}$R$^{d3}$.

In some embodiments, Cy$^2$ is aryl, heteroaryl, or cycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, C(=NR$^{i4}$)NR$^{c4}$R$^{d4}$, NR$^{c4}$C(=NR$^{i4}$)NR$^{c4}$R$^{d4}$, P(R$^{f4}$)$_2$, P(OR$^{e4}$)$_2$, P(O)R$^{e4}$R$^{f4}$, P(O)OR$^{e4}$OR$^{f4}$, S(O)R$^{b4}$, S(O)NR$^{c4}$R$^{d4}$, S(O)$_2$R$^{b4}$, and S(O)$_2$NR$^{c4}$R$^{d4}$.

In some embodiments, Cy$^2$ is aryl or cycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, C(=NR$^{i4}$)NR$^{c4}$R$^{d4}$, NR$^{c4}$C(=NR$^{i4}$)NR$^{c4}$R$^{d4}$, P(R$^{f4}$)$_2$, P(OR$^{e4}$)$_2$, P(O)R$^{e4}$R$^{f4}$, P(O)OR$^{e4}$OR$^{f4}$, S(O)R$^{b4}$, S(O)NR$^{c4}$R$^{d4}$, S(O)$_2$R$^{b4}$, and S(O)$_2$NR$^{c4}$R$^{d4}$.

In some embodiments, $Cy^2$ is aryl optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $C(=NR^{i4})NR^{c4}R^{d4}$, $NR^{c4}C(=NR^{i4})NR^{c4}R^{d4}$, $P(R^{f4})_2$, $P(OR^{e4})_2$, $P(O)R^{e4}R^{f4}$, $P(O)OR^{e4}OR^{f4}$, $S(O)R^{b4}$, $S(O)NR^{c4}R^{d4}$, $S(O)_2R^{b4}$, and $S(O)_2NR^{c4}R^{d4}$.

In some embodiments, $Cy^3$ is aryl, heteroaryl, or cycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $C(=NR^{i5})NR^{c5}R^{d5}$, $NR^{c3}C(=NR^{i5})NR^{c5}R^{d5}$, $P(R^{f5})_2$, $P(OR^{e5})_2$, $P(O)R^{e5}R^{f5}$, $P(O)OR^{e5}OR^{f5}$, $S(O)R^{b5}$, $S(O)NR^{c5}R^{d5}$, $S(O)_2R^{b5}$, and $S(O)_2NR^{c5}R^{d5}$.

In some embodiments, $Cy^3$ is aryl or cycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $C(=NR^{i5})NR^{c5}R^{d5}$, $NR^{c3}C(=NR^{i5})NR^{c5}R^{d5}$, $P(R^{f5})_2$, $P(OR^{e5})_2$, $P(O)R^{e5}R^{f5}$, $P(O)OR^{e5}OR^{f5}$, $S(O)R^{b5}$, $S(O)NR^{c5}R^{d5}$, $S(O)_2R^{b5}$, and $S(O)_2NR^{c5}R^{d5}$.

In some embodiments, $Cy^3$ is aryl optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $C(=NR^{i5})NR^{c5}R^{d5}$, $NR^{c3}C(=NR^{i5})NR^{c5}R^{d5}$, $P(R^{f5})_2$, $P(OR^{e5})_2$, $P(O)R^{e5}R^{f5}$, $P(O)OR^{e5}OR^{f5}$, $S(O)R^{b5}$, $S(O)NR^{c5}R^{d5}$, $S(O)_2R^{b5}$, and $S(O)_2NR^{c5}R^{d5}$.

$Cy^{a1}$, $Cy^{a2}$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $C(=NR^{i6})NR^{c6}R^{d6}$, $NR^{c6}C(=NR^{i6})NR^{c6}R^{d6}$, $P(R^{f6})_2$, $P(OR^{e6})_2$, $P(O)R^{e6}R^{f6}$, $P(O)OR^{e6}OR^{f6}$, $S(O)R^{b6}$, $S(O)NRC^{c6}R^{d6}$, $S(O)_2R^{b6}$, and $S(O)_2NR^{c6}R^{d6}$.

In some embodiments, Z is $CHNR^{g1}$.

In some embodiments, Z is $CHOR^{g1}$.

In some embodiments, Z is absent, O, S, $NR^{g1}$, $CH_2$, $SO_2$, $CH(OR^{g1})$, CO, $CH(NR^{g1})$, or $C_{1-6}$ alkyl-O.

In some embodiments, Z is S.

In some embodiments, Y is $C(O)$, $NR^{g2}CO$, $SO_2NR^{g2}$, $NR^{g2}SO_2$, NHC(O)NH, NHC(O)O, OC(O)NH, or $CONR^{g2}$.

In some embodiments, Y is C(O)NH.

In some embodiments, $R^1$ is H, halo, $C_{1-6}$ alkyl, $C_{1-6}$ haloalkyl, $C_{2-6}$ alkenyl, $C_{2-6}$ alkynyl, $Cy^{a1}$, $SO_2NR^{c1}R^{d1}$, $NHSO_2$—$C_{1-6}$ alkyl, $C_{1-6}$ cyanoalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $Cy^{a1}$, or $Cy^{a1}$-($C_{1-6}$ alkyl)-, wherein said $C_{1-6}$ alkyl, $C_{2-6}$ alkenyl, or $C_{2-6}$ alkynyl, is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, and $NR^{c1}C(O)OR^{a1}$.

In some embodiments, $R^1$ is H, halo, $C_{1-6}$ alkyl, $C_{1-6}$ haloalkyl, $C_{2-6}$ alkenyl, C2-6 alkynyl, $SO_2NR^{c1}R^{d1}$, $NHSO_2$—$C_{1-6}$ alkyl, $C_{1-6}$ cyanoalkyl, CN, $NO_2$, $OR^{a1}$, or $SR^{a1}$, wherein said $C_{1-6}$ alkyl, $C_{2-6}$ alkenyl, or $C_{2-6}$ alkynyl, is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, and $NR^{c1}C(O)OR^{a1}$.

In some embodiments, $R^1$ is H, halo, $C_{1-6}$ alkyl, $C_{1-6}$ haloalkyl, $C_{2-6}$ alkenyl, $C_{2-6}$ alkynyl, $SO_2NR^{c1}R^{d1}$, $NHSO_2$—$C_{1-6}$ alkyl, $C_{1-6}$ cyanoalkyl, CN, $NO_2$, $OR^{a1}$, or $SR^{a1}$, wherein said $C_{1-6}$ alkyl, $C_{2-6}$ alkenyl, or $C_{2-6}$ alkynyl, is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, CN, $NO_2$, $OR^{a1}$, and $SR^{a1}$.

In some embodiments, $R^1$ is H, halo, $C_{1-6}$ alkyl, $C_{1-6}$ haloalkyl, $C_{2-6}$ alkenyl, $C_{2-6}$ alkynyl, CN, $NO_2$, $OR^{a7}$, or $SR^{a7}$, wherein said $C_{1-6}$ alkyl, $C_{2-6}$ alkenyl, or $C_{2-6}$ alkynyl, optionally substituted with 1, 2, 3, 4, or 5 substituents independently selected from halo, $C_{1-6}$ alkyl, $C_{2-6}$ alkenyl, $C_{2-6}$ alkynyl, CN, $NO_2$, $OR^{a1}$, and $SR^{a1}$.

In some embodiments, $R^1$ is $NO_2$.

In some embodiments, $R^2$ is H, halo, $C_{1-6}$ alkyl, $C_{1-6}$ haloalkyl, $C_{2-6}$ alkenyl, $C_{2-6}$ alkynyl, $Cy^{a2}$, $SO_2NR^{c2}R^{d2}$, $NHSO_2$—$C_{1-6}$ alkyl, $C_{1-6}$, cyanoalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, or $NR^{c2}C(O)OR^{a2}$, wherein said $C_{1-6}$ alkyl, $C_{2-6}$ alkenyl, or $C_{2-6}$ alkynyl, is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}NR^{c2}R^{d2}$, $NR^{c2}C(O)R^{b2}$, $NR^{c2}C(O)NR^{c2}R^{d2}$, and $NR^{c2}C(O)OR^{a2}$.

In some embodiments, $R^2$ is H, halo, $C_{1-6}$ alkyl, $C_{1-6}$ haloalkyl, $C_{2-6}$ alkenyl, $C_{2-6}$ alkynyl, $CY^{a2}$, $SO_2NR^{c2}R^{d2}$, $NHSO_2$—$C_{1-6}$ alkyl, $C_{1-6}$ cyanoalkyl, CN, $NO_2$, $OR^{a2}$, or $SR^{a2}$, wherein said $C_{1-6}$ alkyl, $C_{2-6}$ alkenyl, or $C_{2-6}$ alkynyl, is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^2C(O)NR^{c2}R^{d2}$, and $NR^{c2}C(O)OR^{a2}$.

In some embodiments, $R^2$ is H, halo, $C_{1-6}$ alkyl, $C_{1-6}$ haloalkyl, $C_{2-6}$ alkenyl, $C_{2-6}$ alkynyl, $Cy^{a2}$, $SO_2NR^{c2}R^{d2}$, $NHSO_2$—$C_{1-6}$ alkyl, $C_{1-6}$ cyanoalkyl, CN, $NO_2$, OR $^{a7}$, or $SR^{a7}$, wherein said $C_{1-6}$ alkyl, $C_{2-6}$ alkenyl, or $C_{2-6}$ alkynyl, is optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{1-6}$ hydroxyalkyl, $C_{1-6}$ cyanoalkyl, CN, $NO_2$, $OR^{a2}$, and $SR^{a2}$.

In some embodiments, $R^2$ is H, halo, $C_{1-6}$ alkyl, $C_{1-6}$ haloalkyl, $C_{2-6}$ alkenyl, $C_{2-6}$ alkynyl, CN, $NO_2$, $OR^{a7}$, or $SR^{a7}$, wherein said $C_{1-6}$ alkyl, $C_{2-6}$ alkenyl, or $C_{2-6}$ alkynyl, is optionally substituted with 1, 2, 3, 4, or 5 substituents independently selected from halo, $C_{1-6}$ alkyl, $C_{2-6}$ alkenyl, $C_{2-6}$ alkynyl, CN, $NO_2$, $OR^{a2}$, and $SR^{a2}$.

In some embodiments, $R^2$ is $C(O)CH_3$.

In some embodiments, $R^2$ is $NH_2$.

In some embodiments, $R^2$ is $OCH_3$.

In some embodiments, $R^{g1}$ and $R^{g2}$ are H.

In some embodiments, $Cy^{a1}$ and $Cy^{a2}$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, and $NR^{c6}C(O)OR^{a6}$.

In some embodiments, $Cy^{a1}$ and $Cy^{a2}$ are independently selected from aryl, heteroaryl, cycloalkyl, and heterocycloalkyl, each optionally substituted by 1, 2, 3, 4 or 5 substituents independently selected from halo, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{c6}$, $NR^{c6}C(O)R^{b6}$, and $NR^{c6}C(O)OR^{a6}$.

In some embodiments, $Cy^{a1}$ and $Cy^{a2}$ are independently selected from aryl, heteroaryl, cycloalkyl, and heterocycloalkyl, each optionally substituted by 1, 2, 3, 4 or 5 substituents independently selected from halo, CN, $NO_2$, $OR^{a6}$, $SR^{a6}$, and $NR^{c6}R^{d6}$.

In some embodiments, $R^{c1}$, $R^{c2}$, $R^{c3}$, $R^{c4}$, $R^{c5}$, and $R^{c6}$ are independently selected from H, $C_{1-10}$ alkyl, $C_{1-10}$ haloalkyl, $C_{2-10}$ alkenyl, $C_{2-10}$ alkynyl, aryl, cycloalkyl, heteroaryl, and heterocycloalkyl, wherein said $C_{1-10}$ alkyl, $C_{1-10}$ haloalkyl, $C_{2-10}$ alkenyl, $C_{2-10}$ alkynyl, aryl, cycloalkyl, heteroaryl, or heterocycloalkyl is optionally substituted with 1, 2, 3, 4, or 5 substituents independently selected from OH, amino, halo, $C_{1-6}$ alkyl, aryl, arylalkyl, heteroaryl, heteroarylalkyl, cycloalkyl, and heterocycloalkyl.

In some embodiments, $R^{c1}$, $R^{c2}$, $R^{c3}$, $R^{c4}$, $R^{c5}$, and $R^{c6}$ are independently selected from H, $C_{1-10}$ alkyl, $C_{1-10}$ haloalkyl, $C_{2-10}$ alkenyl, or $C_{2-10}$ alkynyl, wherein said $C_{1-10}$ alkyl, $C_{1-10}$ haloalkyl, $C_{2-10}$ alkenyl, or $C_{2-10}$ alkynyl is optionally substituted with 1, 2, 3, 4, or 5 substituents independently selected from OH, amino, halo, $C_{1-6}$ alkyl, aryl, arylalkyl, heteroaryl, heteroarylalkyl, cycloalkyl, and heterocycloalkyl.

In some embodiments, $R^{c1}$, $R^{c2}$, $R^{c3}$, $R^{c4}$, $R^{c5}$, and $R^{c6}$ are independently selected from H, $C_{1-10}$ alkyl, $C_{1-10}$ haloalkyl, $C_{2-10}$ alkenyl, or $C_{2-10}$ alkynyl.

In some embodiments, $R^{c1}$, $R^{c2}$, $R^{c3}$, $R^{c4}$, $R^{c5}$, and $R^{c6}$ are H.

In some embodiments, $R^{d1}$, $R^{d2}$, $R^{d3}$, $R^{d4}$, $R^{d5}$, and $R^{d6}$ are independently selected from H, $C_{1-10}$ alkyl, $C_{1-10}$ haloalkyl, $C_{2-10}$ alkenyl, $C_{2-10}$ alkynyl, aryl, cycloalkyl, heteroaryl, and heterocycloalkyl, wherein said $C_{1-10}$ alkyl, $C_{1-10}$ haloalkyl, $C_{2-10}$ alkenyl, $C_{2-10}$ alkynyl, aryl, cycloalkyl, heteroaryl, or heterocycloalkyl is optionally substituted with 1, 2, 3, 4, or 5 substituents independently selected from OH, amino, halo, $C_{1-6}$ alkyl, aryl, arylalkyl, heteroaryl, heteroarylalkyl, cycloalkyl, and heterocycloalkyl.

In some embodiments, $R^{d1}$, $R^{d2}$, $R^{d3}$, $R^{d4}$, $R^{d5}$, and $R^{d6}$ are independently selected from H, $C_{1-10}$ alkyl, $C_{1-10}$ haloalkyl, $C_{2-10}$ alkenyl, or $C_{2-10}$ alkynyl, wherein said $C_{1-10}$ alkyl, $C_{1-10}$ haloalkyl, $C_{2-10}$ alkenyl, or $C_{2-10}$ alkynyl is optionally substituted with 1, 2, 3, 4, or 5 substituents independently selected from OH, amino, halo, $C_{1-6}$ alkyl, aryl, arylalkyl, heteroaryl, heteroarylalkyl, cycloalkyl, and heterocycloalkyl.

In some embodiments, $R^{d1}$, $R^{d2}$, $R^{d3}$, $R^{d4}$, $R^{d5}$, and $R^{d6}$ are independently selected from H, $C_{1-10}$ alkyl, $C_{1-10}$ haloalkyl, $C_{2-10}$ alkenyl, or $C_{2-10}$ alkynyl.

In some embodiments, $R^{d1}$, $R^{d2}$, $R^{d3}$, $R^{d4}$, $R^{d5}$, and $R^{d6}$ are H.

The Vif inhibitors described herein also include compounds listed in FIGS. 1-10, FIG. 18, or FIGS. 19A-D, and enantiomers, diastereomers, and pharmaceutically acceptable salts of these compounds. Of the compounds shown in FIGS. 1-8, which are examples of compounds in formulas III-V, that are known compounds, their use as Vif inhibitors was not known.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, and the like.

As used herein, "alkynyl" refers to an alkyl group having one or more triple carbon-carbon bonds. Example alkynyl groups include ethynyl, propynyl, and the like.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of pentane, pentene, hexane, and the like. A cycloalkyl group having one or more fused aromatic rings can be attached though either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like.

As used herein, a "heteroaryl" group refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to a non-aromatic heterocycle where one or more of the ring-forming atoms is a heteroatom such as an O, N, or S atom. Heterocycloalkyl groups can include mono- or polycyclic (e.g., having 2, 3 or 4 fused rings) ring systems as well as spirocycles. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the non-aromatic heterocyclic ring, for example phthalimidyl, naphthalimidyl, and benzo derivatives of heterocycles such as indolene and isoindolene groups. A heterocycloalkyl group having one or more fused aromatic rings can be attached though either the aromatic or non-aromatic portion. Also included in the definition of heterocycloalkyl are moieties in which any ring-forming C, N, or S atom bears one or two oxo substituents. In some embodiments, the heterocycloalkyl group has from 1 to about 20 carbon atoms, and in further embodiments from about 3 to about 20 carbon atoms. In some embodiments, the heterocycloalkyl group contains 3 to about 20, 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "hydroxyalkyl" refers to an alkyl group substituted with a hydroxyl group.

As used herein, "cyanoalkyl" refers to an alkyl group substituted with a cyano group.

As used herein, "alkoxy" refers to an —O-alkyl group. Example alkoxy groups include methoxy, ethoxy, propoxy (e.g., n-propoxy and isopropoxy), t-butoxy, and the like.

As used herein, "arylalkyl" refers to alkyl substituted by aryl and "cycloalkylalkyl" refers to alkyl substituted by cycloalkyl. An example arylalkyl group is benzyl.

As used herein, "heteroarylalkyl" refers to alkyl substituted by heteroaryl and "heterocycloalkylalkyl" refers to alkyl substituted by heterocycloalkyl.

As used herein, "amino" refers to $NH_2$.

As used herein, "alkylamino" refers to an amino group substituted by an alkyl group.

As used herein, "dialkylamino" refers to an amino group substituted by two alkyl groups.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Pharmaceutical Compositions Containing Vif Inhibitors

The invention includes pharmaceutical compositions for inhibiting Vif that contain a pharmaceutical carrier and a therapeutically effective amount of one or more compounds described herein, e.g., compounds of formulas I-V and/or compounds listed in FIGS. 1-10, FIG. 18, or FIGS. 19A-D.

Methods of formulating pharmaceutical compositions are known in the art; see, e.g., *Remington: The Science and Practice of Pharmacy,* 20th Ed. (Baltimore, Md.: Lippincott Williams & Wilkins, 2000). Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with their intended route of administration. Examples of routes of administration include parenteral, e.g., by intravenous, intradermal, or subcutaneous injection; or mucosal (e.g., by oral ingestion, inhalation, or rectal or vaginal administration) administration. Compositions intended for parenteral administration can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide, as appropriate. A parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The pharmaceutical compositions can also be prepared in the form of suppositories (e.g., with conventional suppository bases such as cocoa butter and other glycerides) or retention enemas for rectal delivery.

In certain embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

These compositions can be administered using routes of administration and dosages similar to those used for known inhibitors of HIV replication and known HIV protease inhibitors.

Once an inhibitor of interest has been identified, standard principles of medicinal chemistry can be used to produce derivatives of the compound. Derivatives can be screened for improved pharmacological properties, for example, efficacy, pharmaco-kinetics, stability, solubility, and clearance. The moieties responsible for a compound's activity in the assays described above can be delineated by examination of structure-activity relationships (SAR) as is commonly practiced in the art. A person of ordinary skill in pharmaceutical chemistry could modify moieties on a candidate compound or agent and measure the effects of the modification on the efficacy of the compound or agent to thereby produce derivatives with increased potency. For an example, see Nagarajan et al. (1988) *J. Antibiot.* 41: 1430-8. Furthermore, if the biochemical target of the compound (or agent) is known or determined, the structure of the target and the compound can inform the design and optimization of derivatives. Molecular modeling software is commercially available (e.g., Molecular Simulations, Inc.) for this purpose.

Preparation of the Vif Inhibitors

A diverse library of 30,000 small molecules was purchased from Chembridge Corporation (16981 Via Tazon, Suite G. San Diego, Calif. 92127). The Vif inhibitors listed in FIGS. 1-8 were identified from this library using the screening methods described herein, in application Ser. No. 10/984, 946, and in Wichroski, M. J.; Ichiyama, I.; and Rana, T. M. *J. Biol. Chem.* 2005, 280(9), 8387-8396. Certain Vif inhibitors of formulae III-V can be purchased commercially. Others can be synthesized using synthetic schemes described herein or by an extension of these schemes using synthetic organic chemistry techniques known to one skilled in the art.

Synthesis of Vif Inhibitors Shown in FIGS. 9 and 10

Vif inhibitors shown in FIGS. 9 and 10 can be synthesized from a common intermediate, 2-(4-nitrophenylthio)benzoic acid 4 as outlined in Scheme 1. Acid 4 can be obtained by the copper catalyzed coupling reaction of 4-iodo-nitrobenzene 1 and methyl 2-mercaptobenzoate 2. After activating the acid 4 with $SOCl_2$, the resulting acylchloride 5 can be reacted with aryl, heteroaryl and alkyl amines 6 to provide a large number of Vif inhibitors shown in FIGS. 9 and 10.

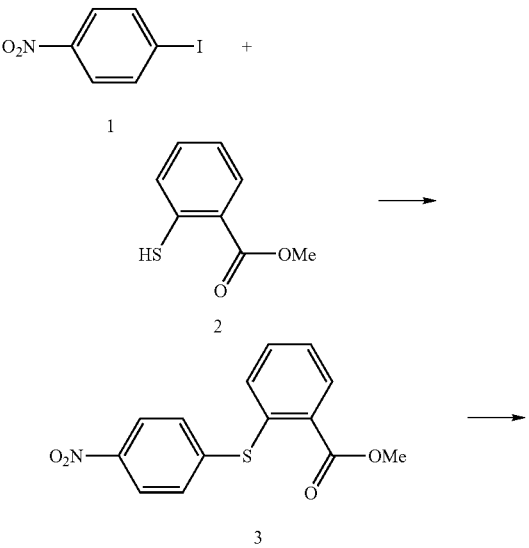

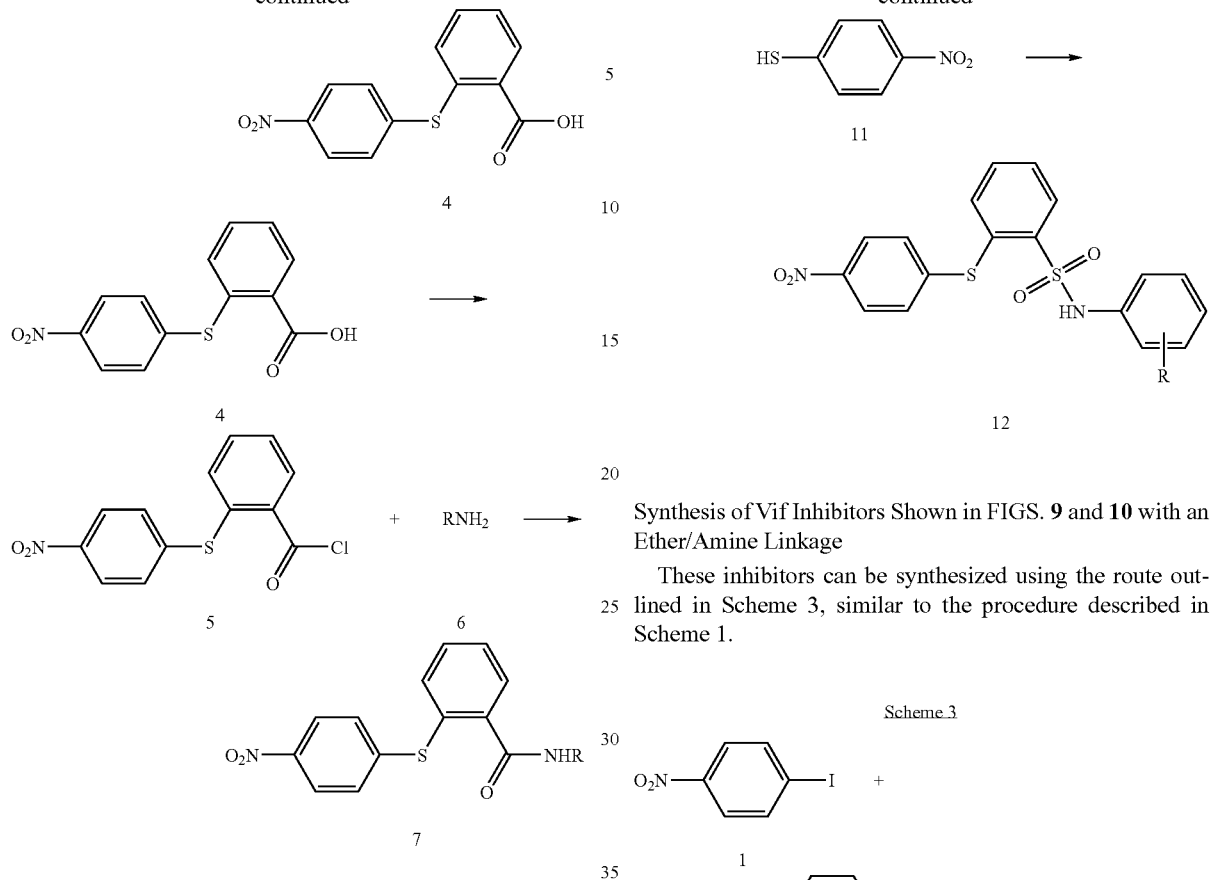

Synthesis of Vif Inhibitors Shown in FIGS. 9 and 10 with an Ether/Amine Linkage These inhibitors can be synthesized using the route outlined in Scheme 3, similar to the procedure described in Scheme 1.

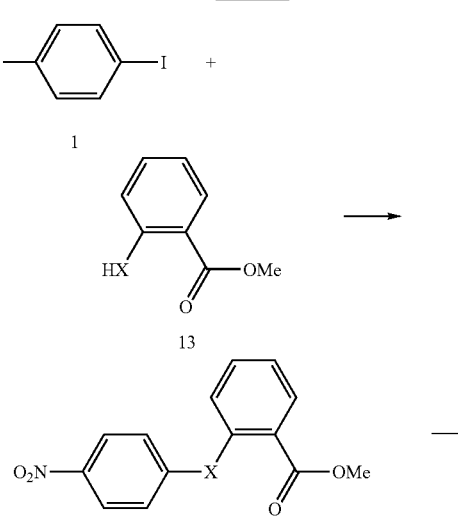

Synthesis of Vif Inhibitors Shown in FIGS. 9 and 10 with a Sulfonamide Linkage Vif inhibitors shown in FIGS. 9 and 10 with Sulfonamide Linkage can be synthesized by replacing the amide linkage between B and C rings with a sulfonamide linkage as outlined in Scheme 2. Reaction of aryl or heteroaryl amines 8 with 2-iodobenzenesulfonyl chloride 9 can provide intermediate sulfonamide 10 that can be coupled with 4-nitrothiophenol 11 to provide desired Vif inhibitors shown in FIGS. 9 and 10 with Sulfonamide Linkage (12).

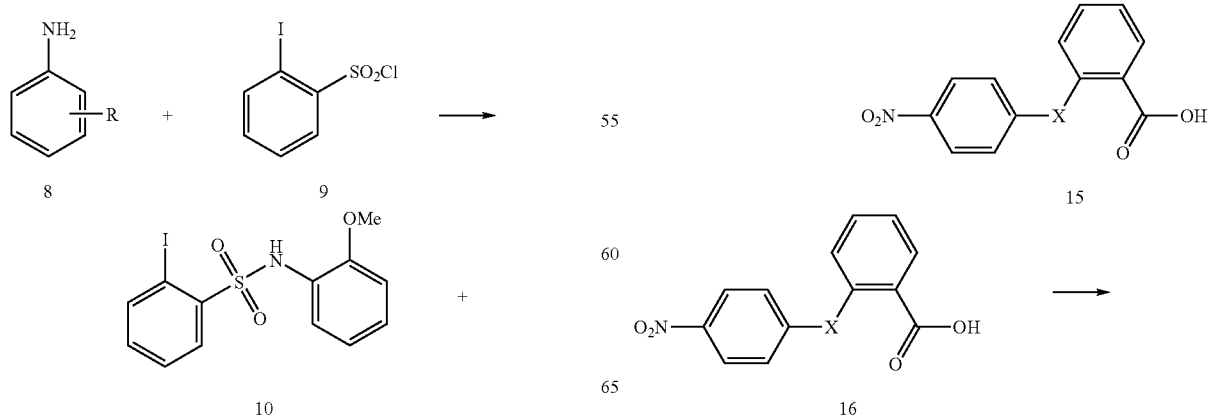

-continued

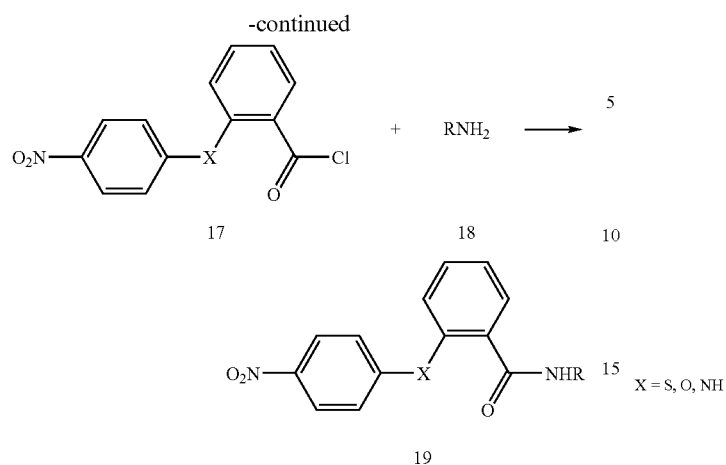

X = O, NH

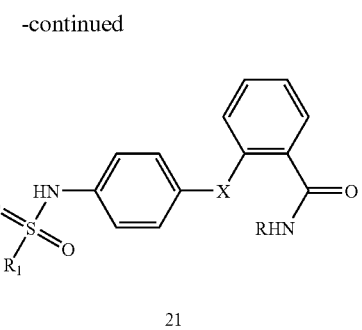

X = S, O, NH

Reduction of the Nitro Group

In order to improve the solubility and cellular uptake of Vif inhibitors shown in FIGS. 9 and 10, the nitro group on ring A can be reduced to an amino group.

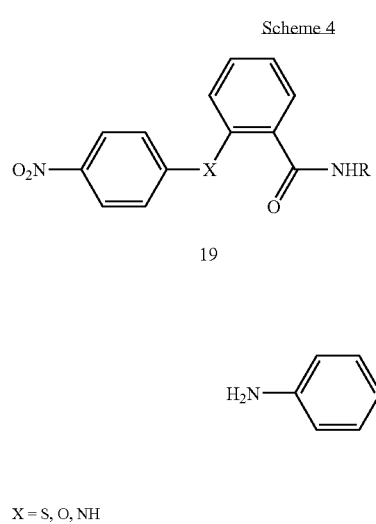

X = S, O, NH

Sulfonamide Synthesis

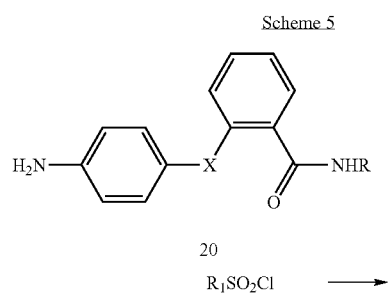

Synthesis of Vif Inhibitors Shown in FIGS. 9 and 10 with a Ring Analog

From commercially available 2-chloro-1-iodo-4-nitrobenzene 21, inhibitors of the type 23 can be synthesized utilizing Scheme 6, which is analogous to Scheme 1.

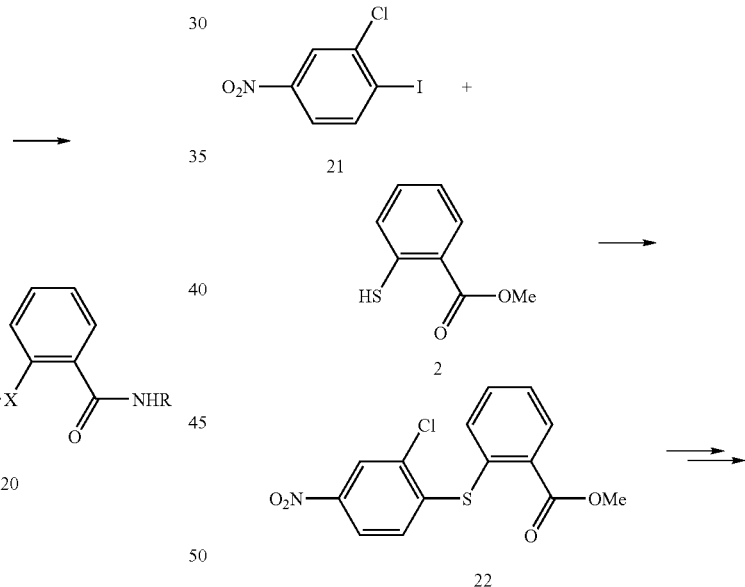

Synthesis of Vif Inhibitors Shown in FIGS. 9 and 10 with a 1,3-Position Linkage Inhibitors of the type 29 can be synthesized using 3-substituted benzoates 24 in the coupling step. The synthetic route for these analogs is described in Scheme 7.

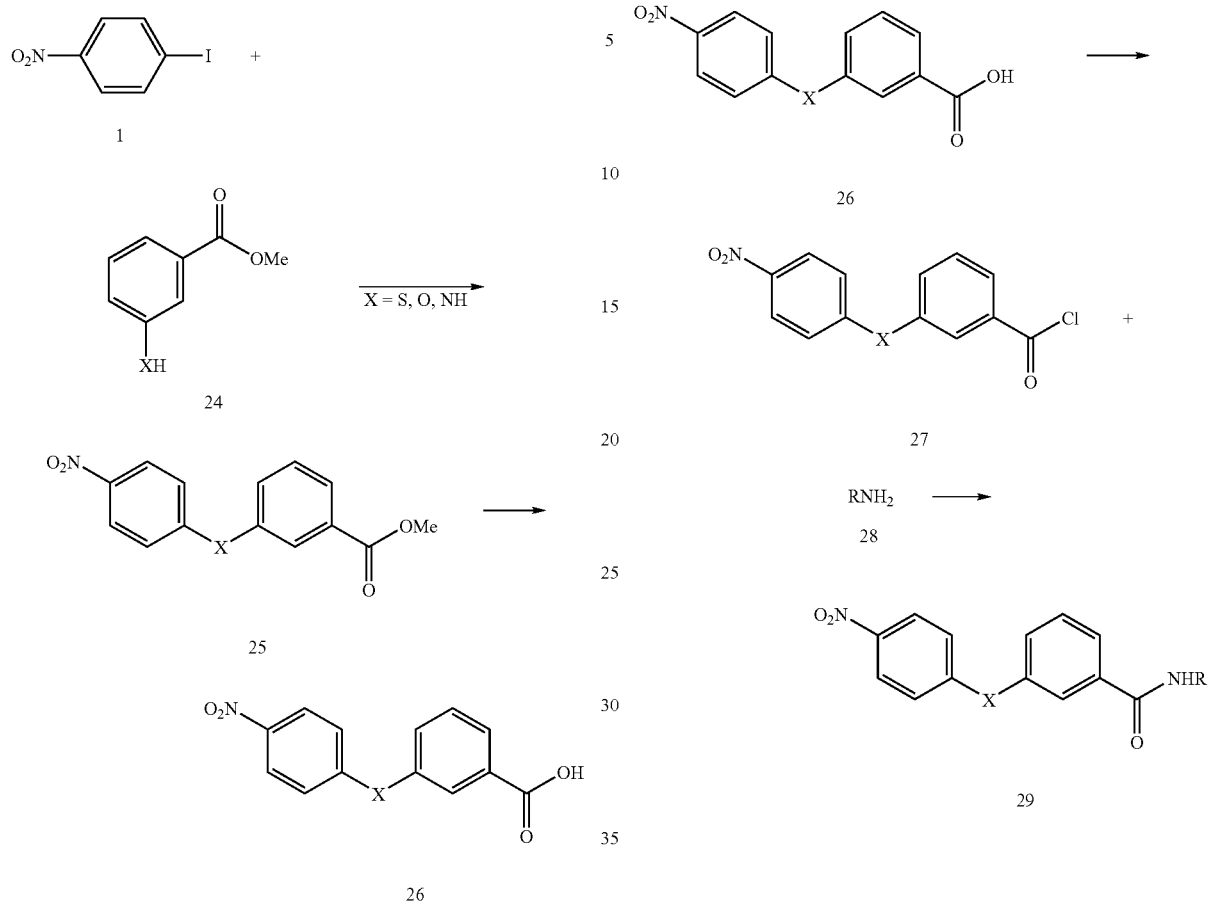
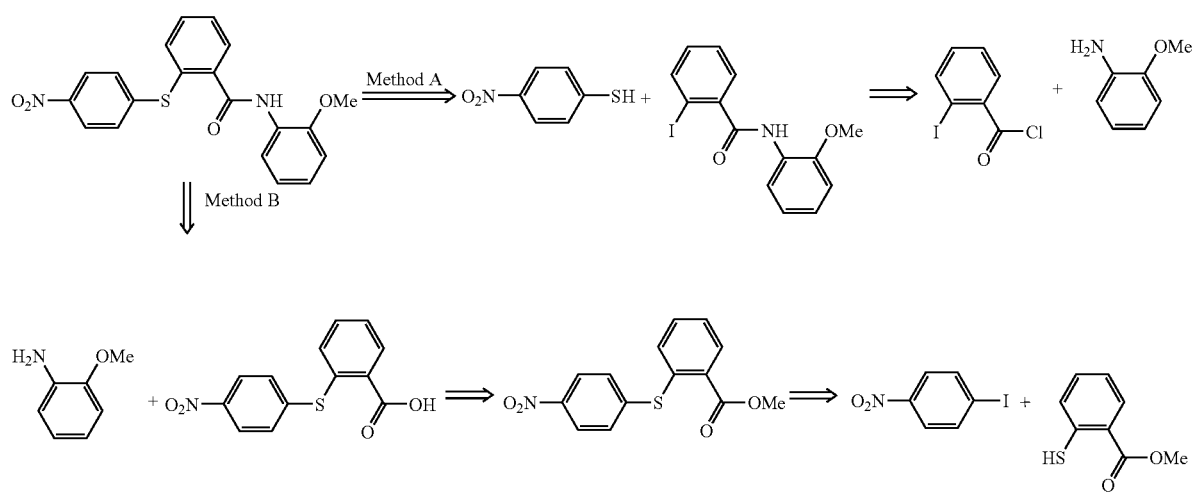
Retro-Synthesis of Vif Inhibitors Shown in FIGS. 9 and 10

Figure 18:
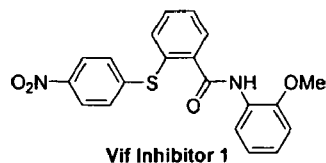
FIG. 18 is a list of compounds that are structural analogs of the Vif inhibitors shown in FIGS. 1-8 and 10A-10B.
Figure 18:
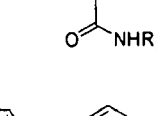
Figure 18:
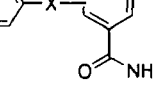
Figure 18:
Figure 18:
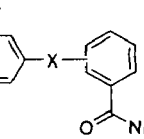
Figure 18:
Figure 18:
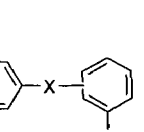
Figure 18:
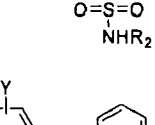
Figure 18:
Figure 19A:
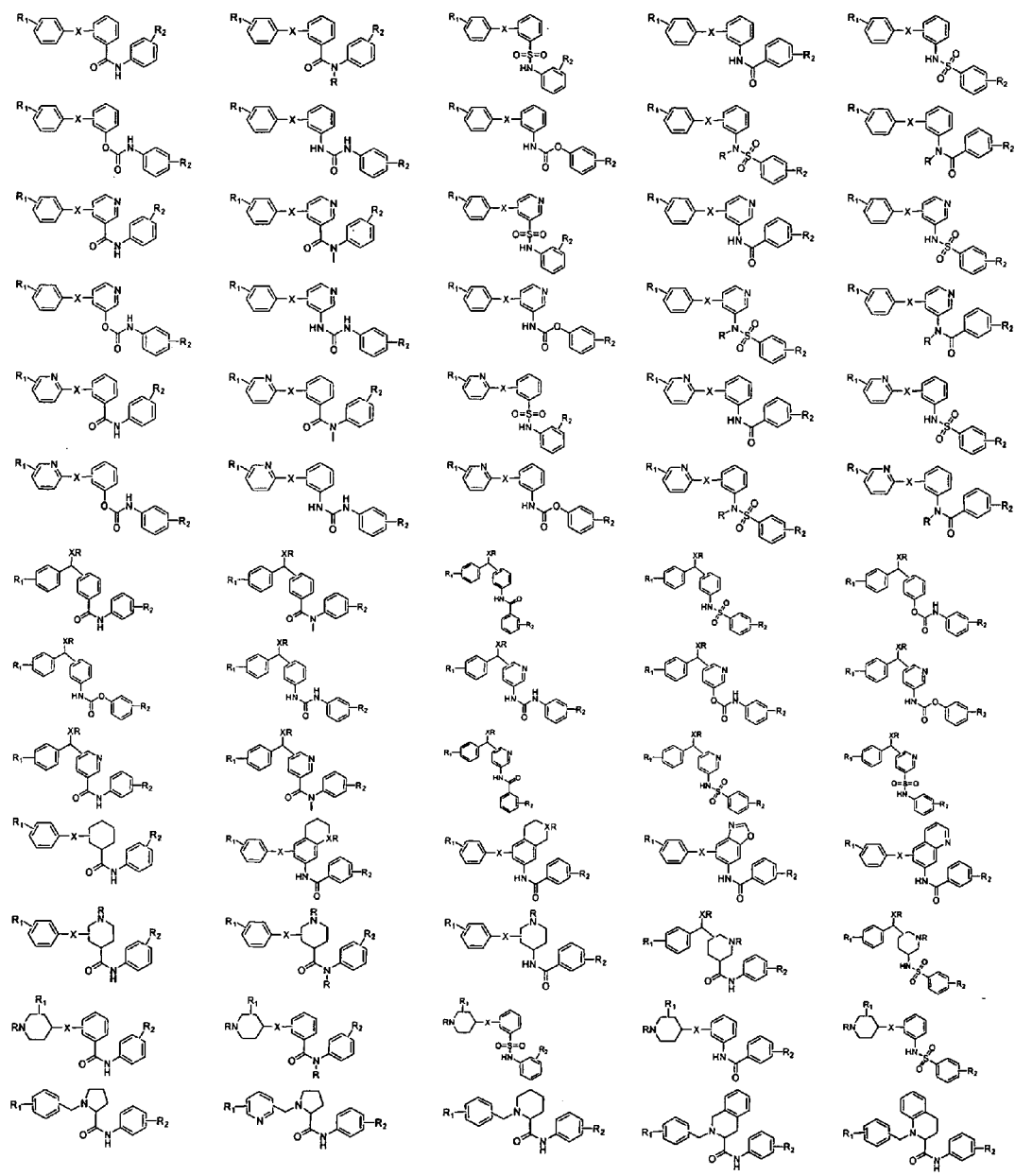
FIGS. 19A-D are lists of compounds that are structural analogs of the Vif inhibitors shown in FIGS. 1-8 and 10A-10B.
Figure 19B:
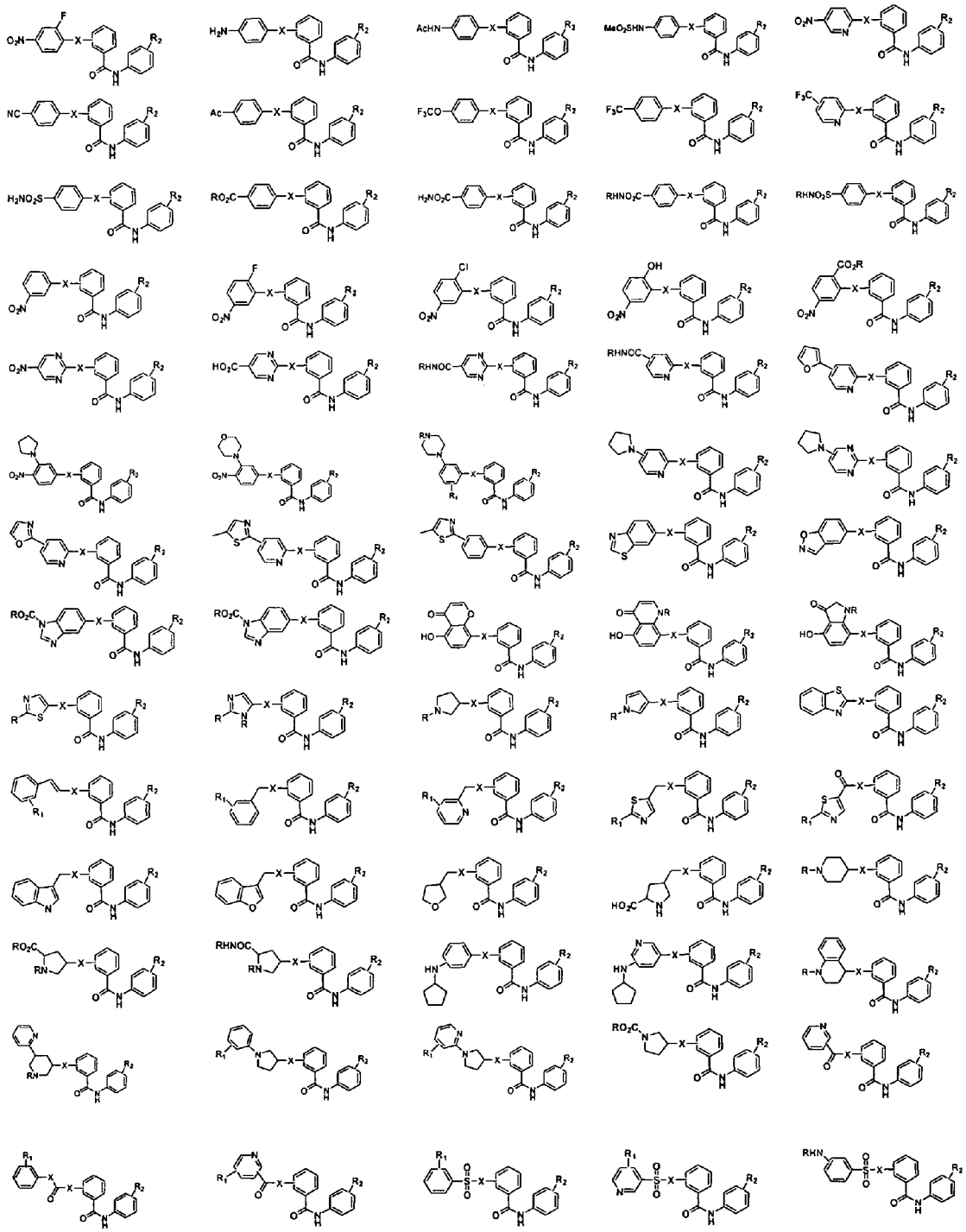
Figure 19C:
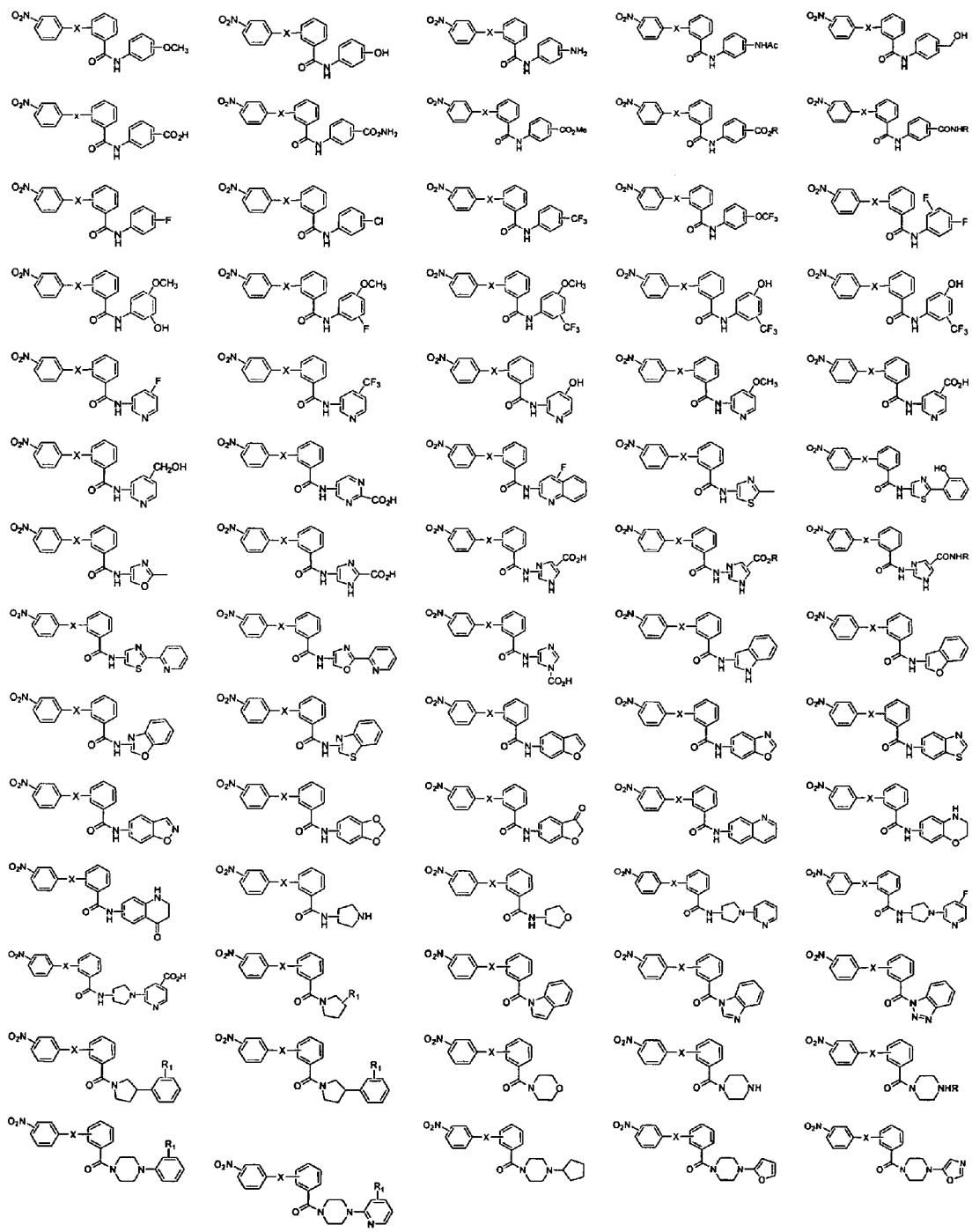
Figure 19D:
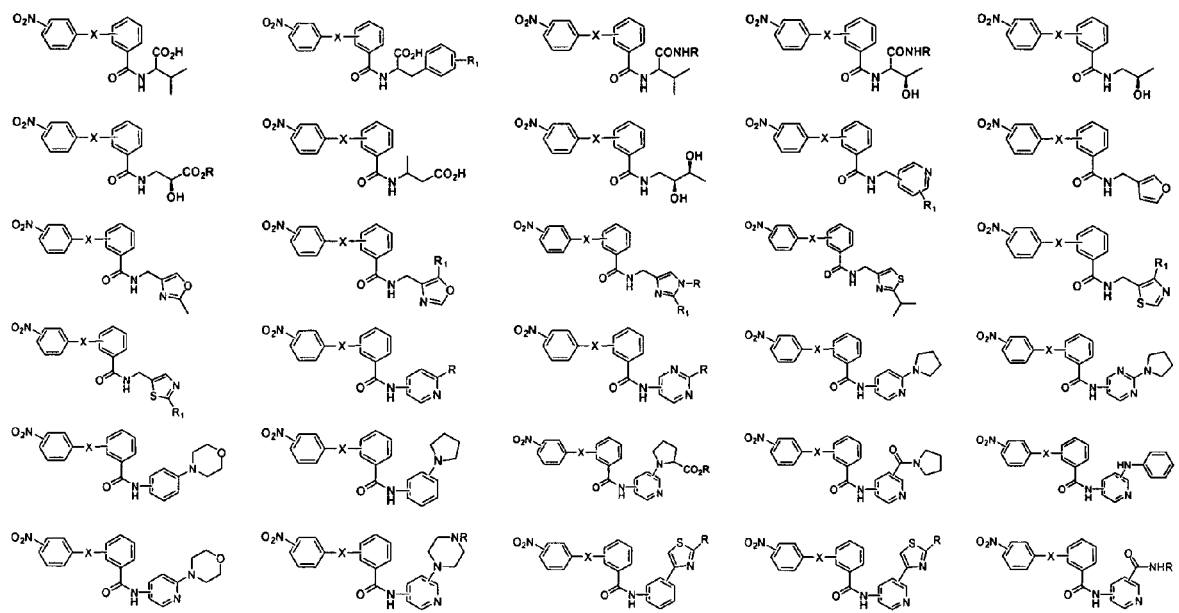

Synthesis of Vif Inhibitor 1 Analogs Shown in FIG. 18: General Reaction Schemes
Analogs of Vif Inhibitor 1 (compound 1, FIG. 10A) can be synthesized using general Schemes 11 to 14.
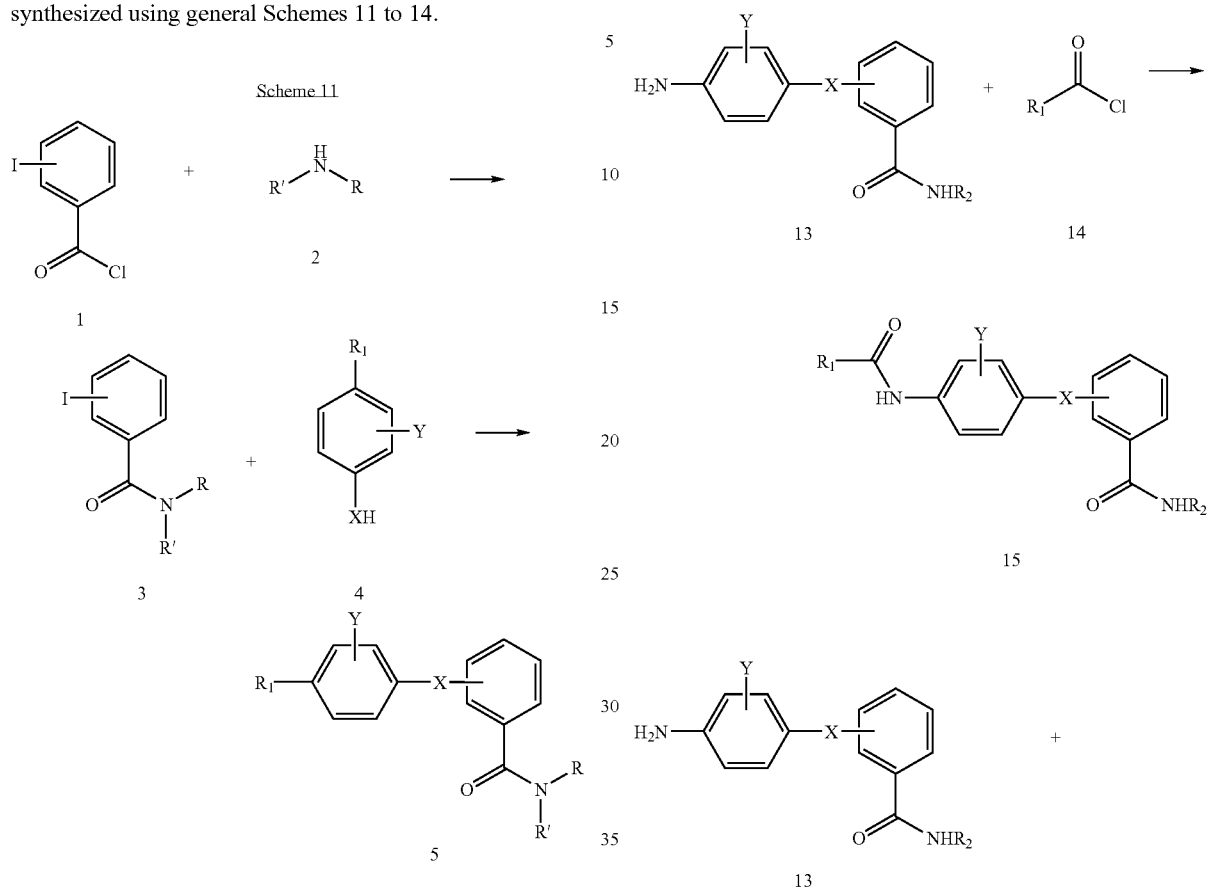
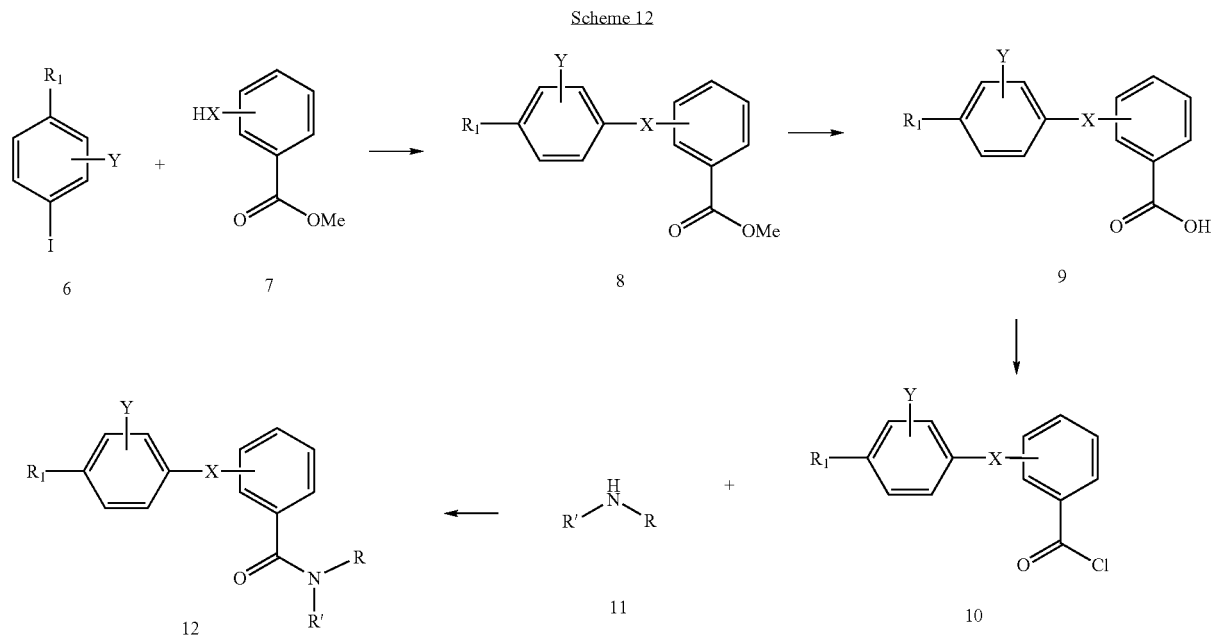

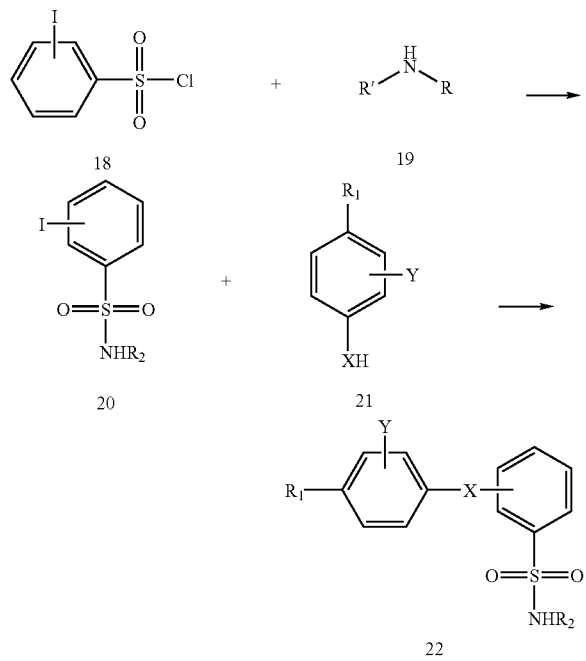

Methods of Treatment

Vif inhibitors described herein can be used therapeutically to restore the innate HIV-1 immunity given to cells by APOBEC3G and/or APOBEC3F and other human host defense proteins, thereby treating subjects having viral, e.g., HIV-1, infections.

Dosage, toxicity, and therapeutic efficacy of such Vif inhibitory compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies typically within a range of circulating concentrations that include the ED50 with little or no toxicity. The dosage can vary within this range depending upon the dosage form employed and the route of administration utilized. For any compound used in the methods described herein, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The pharmaceutical compositions can be included in a container, pack, or dispenser together with instructions for administration.

The pharmaceutical compositions that include a Vif inhibitor can be used in methods of treating a subject who is infected with a virus that comprises Vif, e.g., a lentivirus, e.g., HIV. The methods include administering a therapeutically effective amount of a Vif inhibitor composition described herein to the subject, such that the viral load of the subject is reduced. As defined herein, a therapeutically effective amount of a Vif inhibitor is an amount sufficient to decrease an HIV viral load in a subject infected with HIV. Methods for determining the viral load of a subject are known in the art.

The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the Vif inhibitors of the invention can include a single treatment or can include a series of treatments. The methods described herein can include evaluation of the clinical effectiveness of a Vif inhibitor as described herein, e.g., in a clinical trial or in a general clinical setting, e.g., by evaluating whether the Vif inhibitor has an effect on a subject's viral load. Methods known in the art can be used to determine viral load.

EXAMPLES

The invention is further described in the following examples, which do not limit the scope of the invention described in the claims.

Example 1

Co-Expression of Vif and APOBEC3G Results in the Loss of APOBEC3G

In experiments originally designed to show interaction of Vif and APOBEC3G, it was observed that the total cellular levels of APOBEC3G were reduced dramatically in the presence of Vif The HIV-1subgenomic proviral vector pNL-A1, which harbors HXB2 strain Vif, the corresponding pNL-A1 Δvif vector, and pNL-A1C$_1$, which harbors the Vif$^{C114S}$ mutant are described in Kao et al., (2003) J. Virol. 77:11398-11407. Single-cycle HIV-1 luciferase reporter virus pNL-Luc-E$^-$R$^-$ was used a source for NL4-3 strain Vif. A series of HIV-1 NL4-3 strain Vif deletion mutants, Δ2 (Δ12-23), Δ5 (Δ43-59), Δ6 (Δ58-74), Δ7 (Δ73-87), Δ9 (Δ97-112), Δ10 (Δ111-128), and Δ12 (Δ140-148) (were used and are described in Simon et al., (1999) J. Virol. 73:2675-2681). All chemicals were purchased from Sigma (St. Louis, Mo.) unless otherwise indicated.

To generate Yellow Fluorescent Protein (YFP)-epitope tagged versions of Vif or Vif mutants, the Vif coding region was PCR amplified and cloned into the EcoR1 and BamH1 sites of pEYFP-C1 (BD Biosciences, Palo Alto, Calif.). The APOBEC3G coding region was amplified from cDNA derived from frozen human peripheral blood mononuclear cells. To generate pCyan Fluorescent Protein (CFP)-APO, the APOBEC3G coding sequence was cloned into the HindIII and SacII sites of pECFP-C1 (BD Biosciences). For expression of APOBEC3G with a C-terminal epitope tag, a Kozak ribosome recognition sequence (ccacc) was placed directly upstream of the APOBEC3G start codon during PCR amplification. APOBEC3G with a C-terminal 3× hemagglutinin (HA) tag (pAPO-HA) and pAPO-CFP were engineered by cloning APOBEC3G into the EcoR1 and Xho1 sites of pIRES-hrGFP-2a (Stratagene, La Jolla, Calif.) and the HindIII and SacII sites of pECFP-N1 (BD Biosciences), respectively. Tat-Red Fluorescent Protein (RFP) was generated by cloning HIV-1 Tat into the HindIII and BamHI sites of pDsRED-N1 (BD Biosciences).

To induce random mutations within the Vif$^{C114S}$ coding sequence, pNL-A1 Vif$^{C114S}$ was used as a template for low fidelity PCR and the resulting products were cloned into pEYFP-C1, as described above. DNA from random colonies was prepared (Promega, Madison, Wis.) and used to transfect 293T cells.

The transfected 293T cells were maintained in a humidified incubator (5% CO$_2$) at 37° C. in Dulbecco's modified Eagle's medium (DMEM; Invitrogen) supplemented with 10% fetal bovine serum (FCS), 100 units/ml penicillin and 100 μg/ml streptomycin (P/S) (Invitrogen). Qiagen-purified plasmid DNA (Qiagen, Valencia, Calif.) was transfected into 293T cells using Lipofectamine™ 2000 lipofection agent (Invitrogen). For Western blot and immunoprecipitation experiments, 293T cells were transfected in either 6 or 12 well plates when the cells were ~60% confluent. The amount of vector used and the molar ratio of vector for co-transfection experiments are described in the Results and figure legends. When necessary, final DNA amounts were made equal by the addition of pGEM (Promega). For live imaging and immunolocalization, 293T cells were seeded into poly-d-lysine coated 35 mm glass bottom culture dishes and transfected when the cells were ~50% confluent. For proteasome inhibition studies, culture media containing 100 μM of N-Acetyl-Leu-Leu-Nle-CHO (ALLN, Calbiochem, La Jolla, Calif.) or the equivalent volume of DMSO was added to cells 12 hours prior to harvesting or imaging 36 hours post-transfection.

293T cells were transfected with YFP-Vif and either CFP-APOBEC3G, APOBEC3G-HA, or HIV NL4 proviral DNA (wild type, which includes Vif, or a Vif-deficient strain) at an equimolar ratio (130 fmoles of each vector) using standard lipofection methods. Zero to twenty-four hours later, proteins were isolated and subjected to Western blot analysis. The blots were then analyzed using standard fluorometric methods.

Figure 11A:
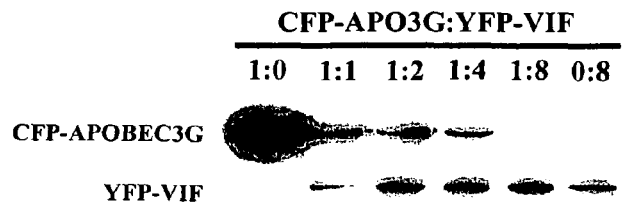
FIG. 11A is a reproduction of a Western blot of protein levels of Cyan Fluorescent Protein (CFP)-APOBEC3G and Yellow Fluorescent Protein (YFP)-Vif fusion proteins, 24 hours after co-transfection in increasing molar ratios of expression vectors into 293T cells at the specified ratios (value of 1=130 fmoles).
Figure 11B:
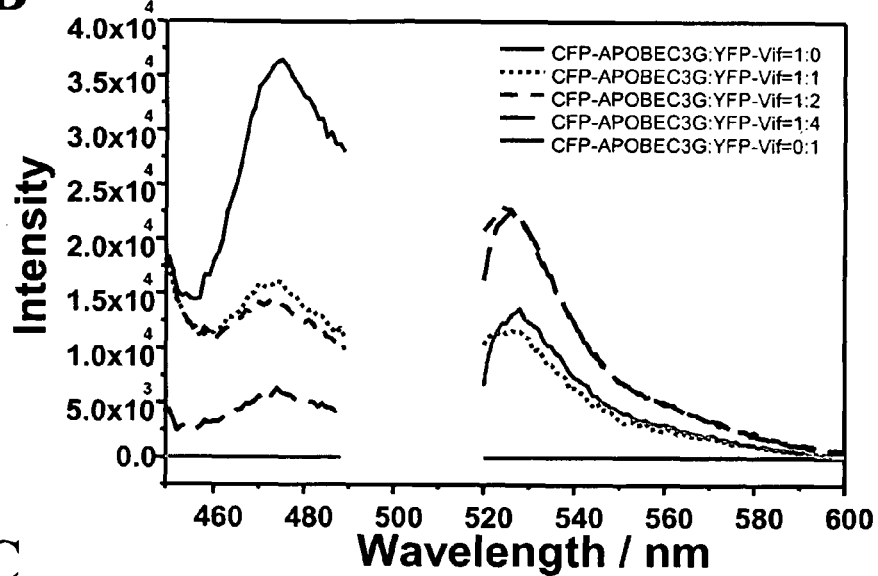
FIGS. 11B-11D are graphs that illustrate the results of fluorometric analysis 24 hours after co-transfection of expression vectors into 293T cells at the specified ratios (value of 1=130 fmoles).
Figure 11C:
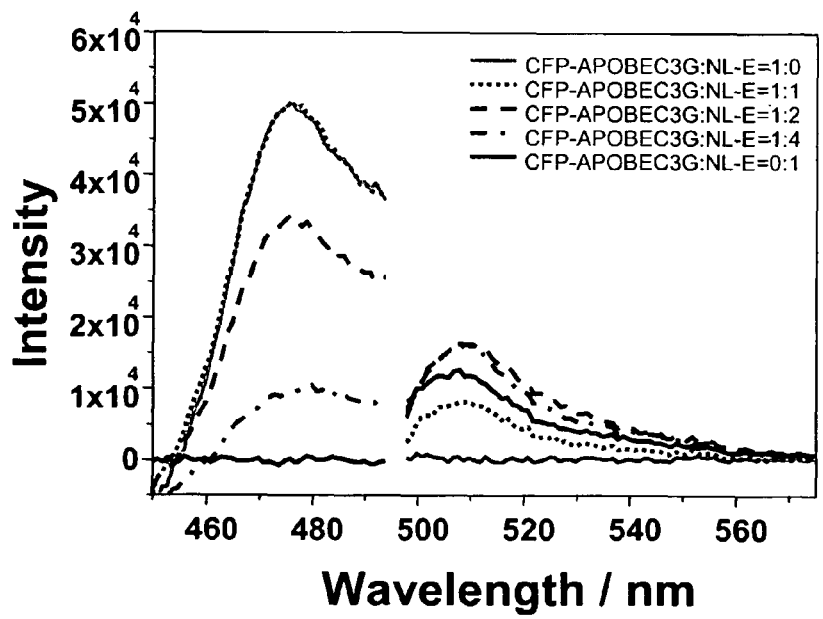

Co-expression of YFP-Vif with either CFP-APOBEC3G or APOBEC3G-HA at an equimolar ratio (130 fmoles of each vector) reduced the expression levels of both APOBEC3G fusion proteins. Furthermore, expression of APOBEC3G was reduced to below detectable levels (by both Western and fluorometric analysis) with increasing amounts of YFP-Vif vector indicating that this effect was dose-dependent (FIGS. 11A-B). This effect was specific to APOBEC3G, as the total cellular levels of endogenous CycT1 remained unaltered and CFP levels remained unaltered when co-expressed with YFP-Vif (FIG. 11A). The levels of CFP-APOBEC3G were also reduced when co-expressed with HIV NL4 wild-type proviral DNA, and not with a corresponding Vif-deficient strain, indicating the Vif was indeed responsible for this effect (FIG. 11C). Similar results were seen in HUT78 and HeLa cells.

Figure 11D:
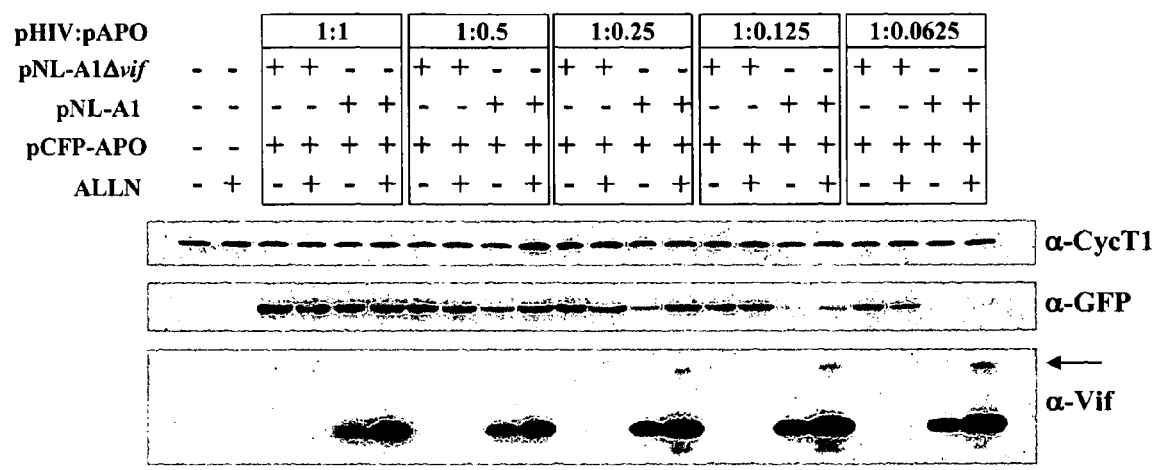

The level of Vif-mediated depletion of APOBEC3G was further determined over a broad range of Vif (pNL-A1):APOBEC3G (pCFP-APO) vector ratios ranging from 1:1 to 1:0.0625, where 1 refers to 130 fmoles of vector. The level of depletion was determined by comparing the steady-state levels of CFP-APO when co-expressed with Vif to the equivalent Δvif control (pNL-A1 Δvif). CFP-APO depletion by Vif was most significant between the 1:0.25 and 1:0.0625 ratios (FIG. 11D). Recovery of CFP-APO levels by proteasome inhibition (ALLN) was most dramatic at the 1:0.25 ratio (FIG. 11D). Despite significant depletion by Vif, only modest recovery of CFP-APO was observed at the 1:0.125 and 1:0.0625 ratios following proteasome inhibition (FIG. 11D). In the absence of Vif, CFP-APO levels were not significantly affected by proteasome inhibition except at the lowest level of pCFP-APO input (1:0.0625 ratio) for which a modest reduction in expression was observed (FIG. 11D). Identical expression profiles were also observed with pAPO-CFP or pAPO-HA in the presence and absence of Vif (data not shown). In the presence (FIG. 11D) or absence of CFP-APO, proteasome inhibition elevated the steady-state levels of Vif and resulted in the appearance of higher molecular weight species (FIG. 11D; arrow). The pNL-A1:pCFP-APO ratio of 1:0.25 was also visualized by confocal microscopy. In cells expressing Vif, CFP-APO was either not visible or was detected at a significantly reduced level relative to the Δvif control. Consistent with immuno-blot analysis, CFP-APO levels were elevated by proteasome inhibition and the number of cells visibly co-expressing the two proteins increased.

These results indicate that transient expression systems can be used to study the relationship between Vif and APOBEC3G effectively. Establishing the appropriate levels of expression is possible and may be crucial for studying the effects of Vif function on APOBEC3G.

Example 2

Subcellular Localization of Vif and APOBEC3G

The subcellular localization of Vif and APOBEC3G either expressed independently or together in live 293T cells was visualized by laser scanning confocal microscopy. YFP-Vif localized predominantly to the nucleus of live 293T cells. YFP-Vif was evenly distributed throughout the nucleus, but was excluded from nucleoli. Less intense cytoplasmic localization was also observed for YFP-Vif, suggesting that although predominantly nuclear, Vif is targeted to both compartments in 293T cells. Titrating the amount of transfected YFP-Vif vector showed that localization was observed first within the nucleus followed by more intense cytoplasmic staining concomitant with an increase in expression. This localization pattern was also observed with C-terminally labeled Vif. Furthermore, YFP-Vif expressed in the non-permissive HUT78 cell line exhibited both nuclear and cytoplasmic localization. CFP-APOBEC3G localized exclusively to the cytoplasm in live 293T cells. In the majority of cells observed, CFP-APOBEC3G appeared evenly distributed throughout the cytoplasm; however, a punctate and often perinuclear localization pattern was also observed.

This pattern was suggestive of co-localization with components of the secretory pathway and thus may have relevance to virion packaging. The localization patterns of either N-terminal or C-terminal labeled APOBEC3G were indistinguishable and the same localization pattern was observed in HUT78 cells. As observed in FIGS. 11A-C, the total cellular levels of CFP-APOBEC3G were reduced when co-expressed with YFP-Vif and this effect appeared to be dose-dependent with no CFP-APOBEC3G detectable when co-expressed with 8-fold more YFP-Vif vector. Interestingly, YFP-Vif exhibited predominantly cytoplasmic localization when co-expressed with CFP-APOBEC3G, indicating that the mechanism by which Vif alters the expression levels of APOBEC3G occurs in the cytoplasm. This result suggests a functional interaction between Vif and APOBEC3G at the protein level as significant co-localization of the proteins was observed in the cytoplasm.

Example 3

Vif Targets APOBEC3G for Proteasome Degradation

The results described in Example 2 suggest a functional interaction at the protein level and thus possible targeting of APOBEC3G for proteasome degradation. YFP-Vif and CFP-APOBEC3G were co-expressed at a 4:1 molar ratio of vectors (1=130 fmoles) in 293T cells and were treated with the proteasome inhibitors lactacystin (10 μM), ALLN (150 μM), or MG-132 (10 μM) 24 hours post-transfection.

To prepare total protein lysates, each well of a 6- or 12-well plate was washed once in phosphate buffered saline (PBS, Invitrogen) and then lysed in either 400 or 200 μl, respectively, of Mammalian Protein Extraction Reagent (M-PER, Pierce, Rockford, Ill.) supplemented with 0.5% (v/v) Triton-X 100 (Pierce), 150 mM NaCl, 5 mM EDTA, and a 1/100 (v/v) dilution of a protease inhibitor cocktail for mammalian tissue for 30 minutes at 4° C. with gentle rotation. Lysates were harvested from the well and insoluble material was removed by centrifugation for 5 minutes at full-speed in a microcentrifuge. Protein concentration was determined by $D_c$ protein assay (Bio-Rad, Hercules, Calif.).

For immunoprecipitation, 0.5 mg of lysate was diluted to 0.5 mg/ml in 1 ml of lysis buffer. APO-HA was precipitated by incubation with agarose-conjugated rabbit α-HA (20 μg IgG; Santa Cruz Biotechnology, Inc., Santa Cruz, Calif.). To immunoprecipitate CFP-APO, lysates were first pre-cleared with a 50 μl bed volume of Protein G Sepharose (Amersham Pharmacia Biotech, Piscataway, N.J.) for 1 hour at 4° C. CFP-APO was then precipitated from pre-cleared lysates by incubation with 5 μg of a α-GFP rabbit polyclonal (BD Biosciences) for 3 hours at 4° C. Antibody was captured by incubation with a 50 μl bed volume of Protein G Sepharose for 1 hour at 4° C. followed by 4 washes in 1 ml of lysis buffer for 10 minutes each time. Protein was eluted by boiling for 5 minutes at 100° C. in sample buffer [50 mM Tris-HCl, pH 6.8, 100 mM dithiothreitol, 2% (w/v) SDS, 0.1% (w/v) bromophenol blue, 10% (v/v) glycerol].

For SDS-PAGE of protein lysates, samples were denatured and reduced by adding 4×SDS-PAGE sample buffer followed by boiling at 100° C. for 5 min. Protein was resolved by 12% SDS-PAGE and transferred onto a polyvinylidene difluoride membrane (PVDF, Bio-Rad Laboratories, Inc., Hercules, Calif.) using a Semi-Dry Electroblotter (Bio-Rad). Following transfer, membrane was blocked overnight in 5% (w/v) non-fat dry milk in TBS-T [20 mM Tris, pH 7.4, 150 mM NaCl, 0.1% (v/v) Tween 20] and washed 3× for 10 minutes each in TBS-T before and after the addition of antibody. All antibodies were diluted in 2.5% (w/v) nonfat dry milk in TBS-T. CFP, YFP, and GFP were detected using a mouse monoclonal antibody (MAb) against GFP diluted to 1 μg/ml (BD Bioscience). RFP was detected with a rabbit polyclonal (BD Biosciences) diluted to 0.1 μg/ml. Human CycT1 was detected with a goat anti-CycT1 polyclonal antibody (Santa Cruz Biotechnology) diluted to 0.1 μg/ml. HA was detected with a rabbit polyclonal antibody (Santa Cruz Biotechnology, Inc.) diluted to 0.02 μg/ml. Vif and Vif mutants were detected using a Vif MAb diluted 1/5000 (this reagent was obtained through the AIDS Research and Reference Reagent Program, Division of AIDS, NIAID, NIH: HIV-1 Vif Monoclonal Antibody (#319) from Dr. Michael H. Malim (see Simon et al., (1995) J. Virol. 69:4166-4172; Simon et al., (1997) J. Virol. 71:5259-5267; and Fouchier et al., (1996) J. Virol. 70:8263-8269)). All horseradish peroxidase-conjugated secondary antibodies were used at a dilution of 0.05 μg/ml (Santa Cruz Biotechnology, Inc.). Blots were developed with the BM Chemiluminescence Blotting Kit (Roche Molecular Biochemicals, Indianapolis, Ind.) and exposed to Kodak BioMax MR X-ray film (Eastman Kodak Company, Rochester, N.Y.).

Figure 12A:
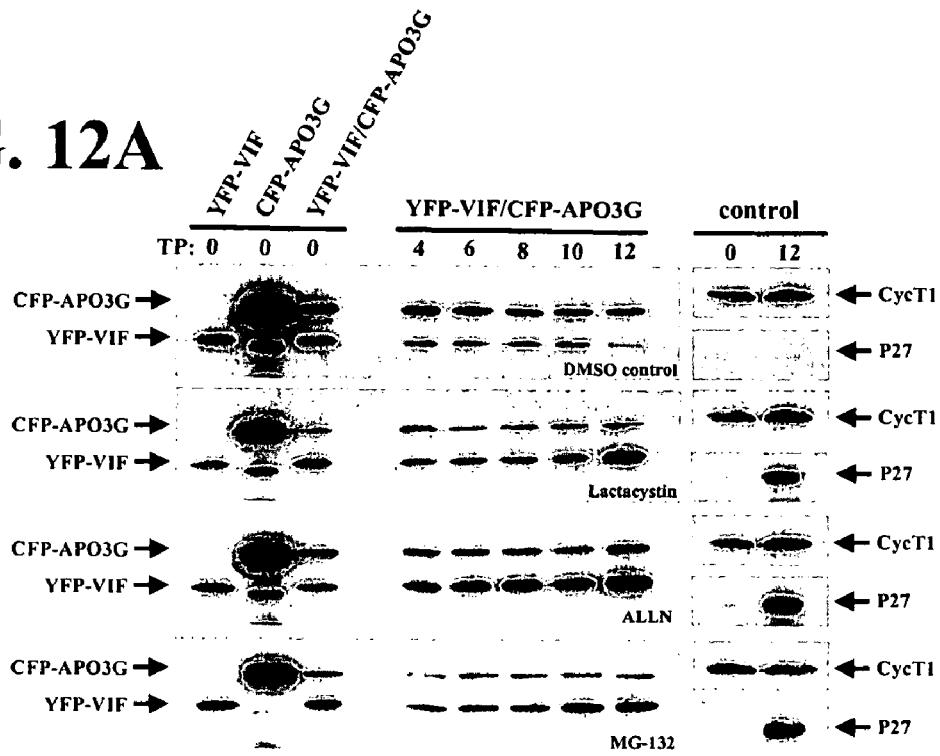
FIG. 12A is a composite of Western blots of CFP-APOBEC3G and YFP-Vif co-transfected into 293T cells at a 1:4 molar ratio (1=130 pmoles). CFP-APO3G=CFP-APOBEC3G

Addition of inhibitor represents time-point 0 and total cell lysates were made at two hour intervals beginning at 4 hours and ending at 12 hours post-addition of proteasome inhibitor. As a positive control for proteasome inhibition, the endogenous levels of the cyclin-dependent kinase inhibitor, p27, a protein known to be targeted for proteasome degradation was observed before (TP 0) and after (TP 12) the 12 hour time course with inhibitors. At the total cell protein level loaded per lane, p27 was barely detectable; however, the levels of the protein rose dramatically after a 12 hour incubation with all three proteasome inhibitors. As a control for protein loading, the endogenous levels of CycT1 were observed on the same blot. Results are shown in FIG. 12A. As expected, the levels of CFP-APOBEC3G (CFP-APO3G) were reduced in the presence of Vif; however, proteasome inhibition by all three inhibitors resulted in no obvious effect on CFP-APOBEC3G expression. Conversely, the levels of YFP-Vif appeared to increase with proteasome inhibition suggesting that a subset of YFP-Vif may be degraded through the proteasome. This may not be altogether surprising as FIG. 11A showed that the levels of Vif appear to plateau. These results do not exclude the possibility that Vif mediates degradation of APOBEC3G through a proteasome-independent pathway.

Example 4

Effect of Vif on APOBEC3G mRNA Degradation

Figure 12B:
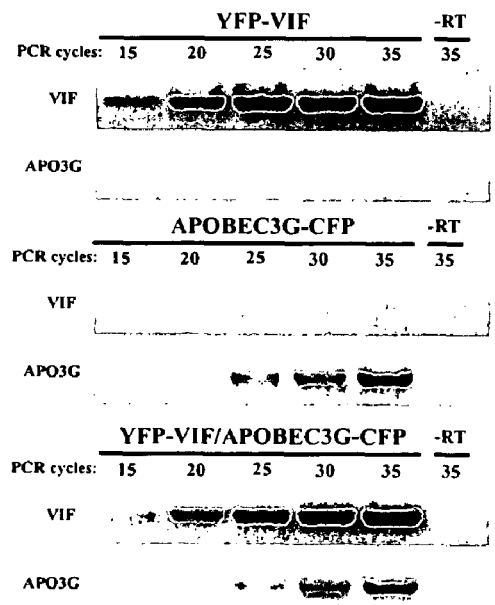
FIG. 12B is a composite of a gel showing the results of real-time PCR performed on oligo d(T) primed cDNA using primers that amplified the entire coding region of either APOBEC3G (APO3G) or Vif.

To determine if Vif mediates degradation of APOBEC3G mRNA the total cellular levels of message were observed by real-time PCR. Total cellular RNA was isolated using standard methodology from cells expressing YFP-Vif alone, CFP-APOBEC3G alone, or both at an 8:1 molar ratio (1=130 fmoles) of transfected vector, respectively, and reverse transcribed using oligo d(T) primer to specifically detect mRNA. No obvious difference was observed in the total cellular levels of either YFP-Vif or CFP-APOBEC3G (APO3G) mRNA when co-expressed (FIG. 12B). This experiment rules out Vif functioning on the levels of transcription or mRNA processing and suggests that Vif does not function at the level of mRNA degradation or turnover. Furthermore, this confirmed that both expression vectors were successfully co-transfected, demonstrating that the decrease in CFP-APOBEC3G expression was not due to a phenomena associated with co-transfection.

Example 5

Vif Inhibits APOBEC3G mRNA Translation

Figure 13A:
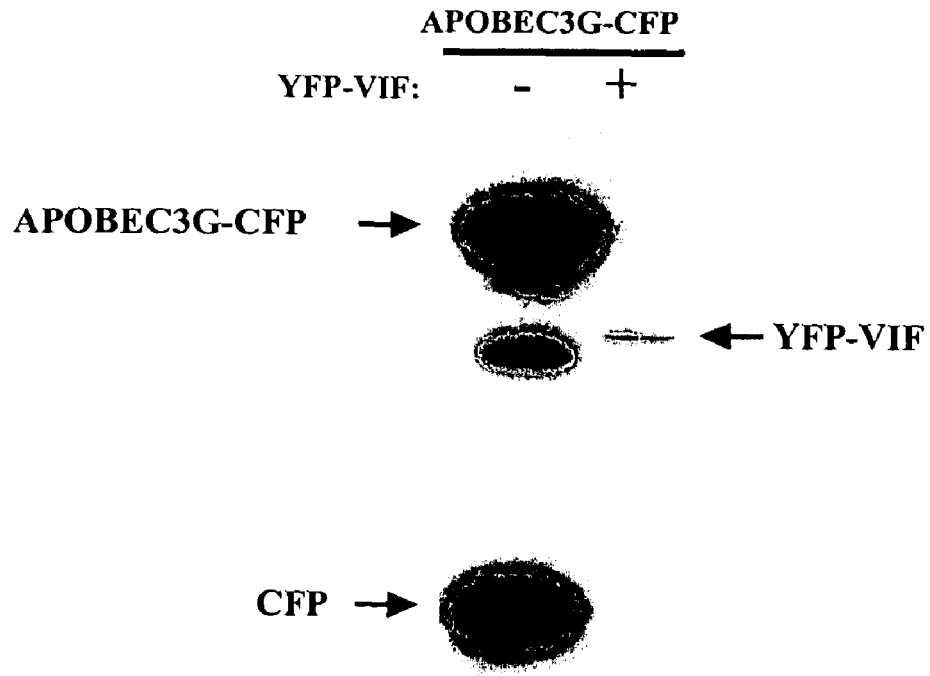
FIG. 13A is a Western blot of protein isolated from cells co-transfected with YFP-Vif and vectors that express CFP, CFP-APOBEC3G or APOBEC3G-CFP, all at a 1:8 molar ratio (1=130 pmoles), probed with an anti-GFP antibody.

Considering that CFP-APOBEC3G was not degraded via the proteasome pathway and that total mRNA levels of APOBEC3G appeared unaltered in the presence of YFP-Vif, we postulated that Vif may function at the levels of either mRNA export or inhibition of translation. Since expression of CFP-APOBEC3G results in an increase in YFP-Vif localization to the cytoplasm, the latter mechanism of inhibition seems most likely. To test this, an expression vector was engineered to express independent proteins from the same transcript through the use of multiple start codons with Kozak sequences to facilitate translation initiation. APOBEC3G was cloned directly upstream of CFP which already harbored its own start codon and Kozak sequence (CCACC) to facilitate translation initiation. An additional Kozak sequence was placed directly upstream of the APOBEC3G start codon (FIG. 13B), and it was shown by Western blot analysis of total cell lysates that expression from this vector after 24 hours in 293T cells resulted in the translation of both APOBEC3G-CFP and CFP alone (FIG. 13A). When co-expressed with YFP-Vif, the expression of both APOBEC3G-CFP and CFP was reduced.

Figure 13B:
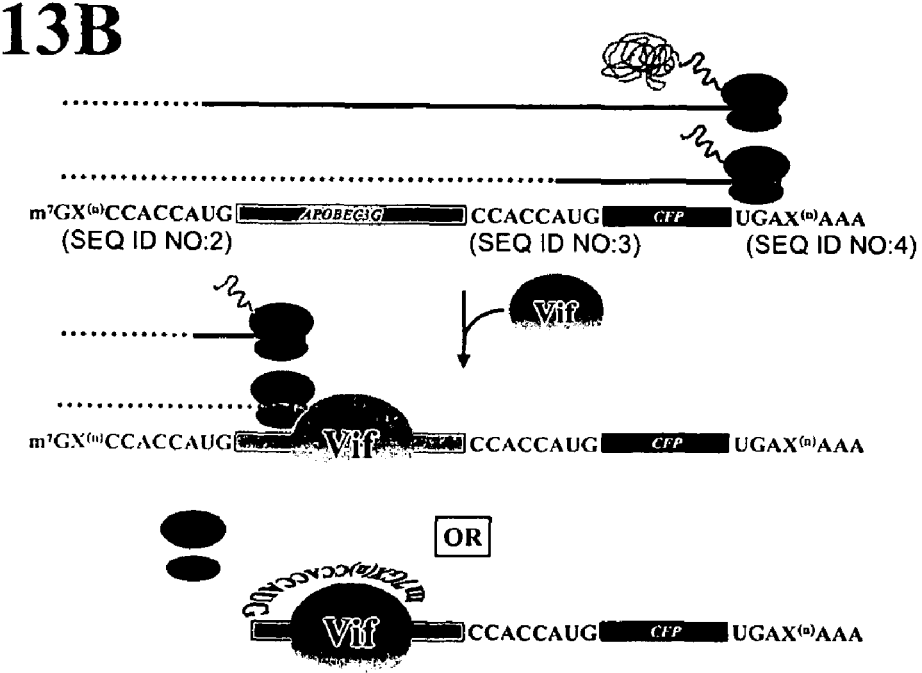
FIG. 13B is a schematic illustration of an APOBEC3G-CFP vector designed to promote translation of both full length APOBEC3G-CFP and CFP alone from the same mRNA transcript, through the addition of a Kozak sequence (CCACC (SEQ ID NO:1)) and start codon (SEQ ID NO:3) upstream of the CFP coding region.

These results showed that YFP-Vif was affecting the translation of both APOBEC3G-CFP and CFP from the same APOBEC3G-CFP transcript, and that YFP-Vif was specifically inhibiting translation of APOBEC3G-CFP mRNA regardless of the translation start site. Thus, collectively, this analysis strongly suggested that Vif specifically functions to alter APOBEC3G expression by inhibiting translation and that the elements required for this inhibition resided within the mRNA sequence encoding APOBEC3G. When co-expressed with YFP-Vif, the expression of both APOBEC3G-CFP and CFP was reduced indicating that Vif functions by preventing translation. Based on these results, we propose a model in which Vif binds to region(s) within the APOBEC3G mRNA coding sequence, thus either preventing translation elongation or ribosome binding (FIG. 13B). It is not clear whether this event initiates within the nucleus and then Vif is transported out of the nucleus with APOBEC3G mRNA or cytosolic synthesized Vif binds to cytosolic mRNA preventing normal Vif localization to the nucleus.

Example 6

High Throughput Screening of a Small Molecule Library

Figure 14:
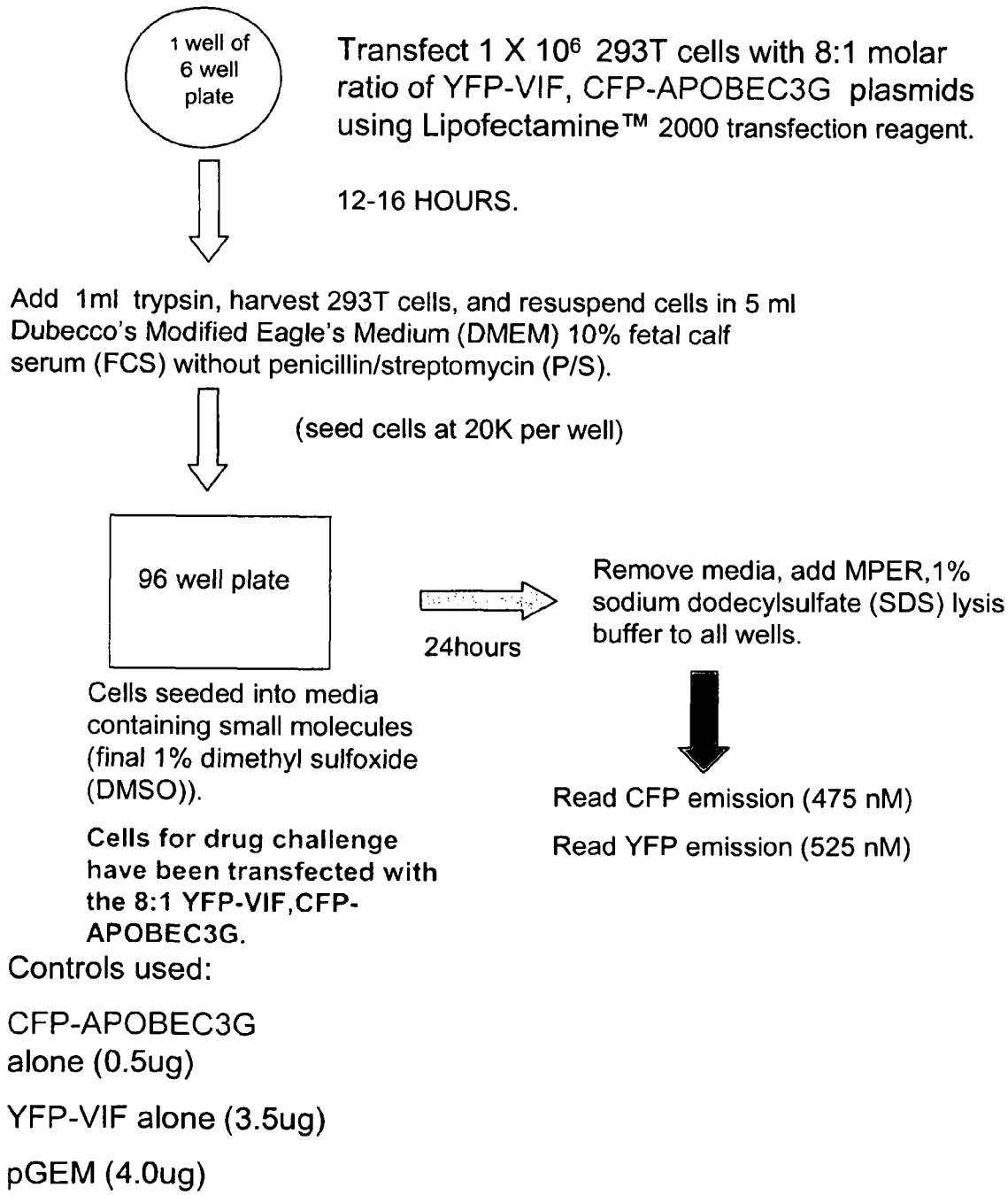
FIG. 14 is a schematic illustration of one embodiment of a high-throughput screening method described herein.
Figure 15A:
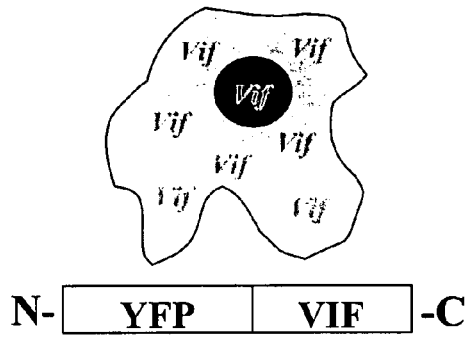
FIGS. 15A-15C are schematic illustrations of one embodiment of a high-throughput screening method described herein.
Figure 15B:
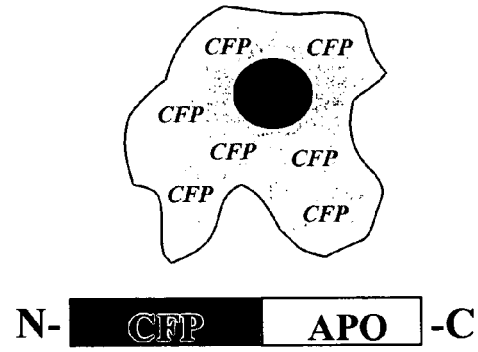
Figure 15C:
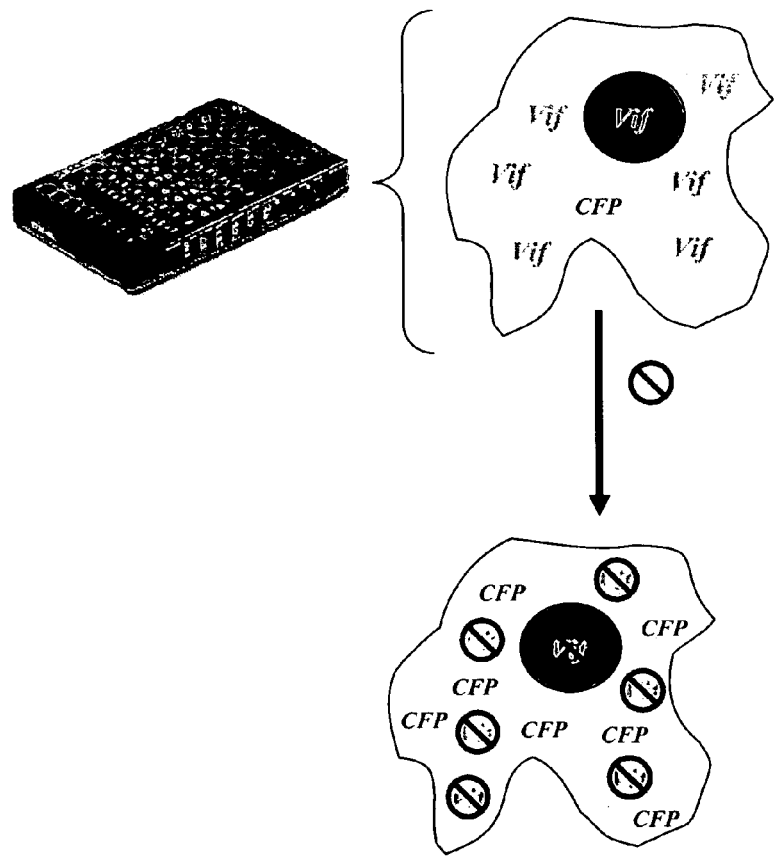
Figure 16A:
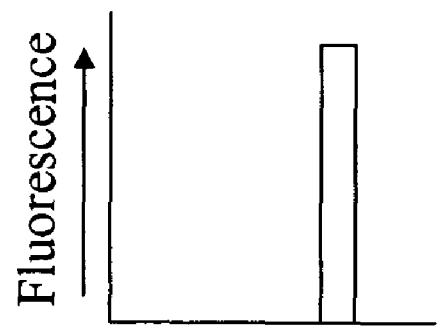
FIGS. 16A-16C are exemplary bar graphs showing that cells containing both YFP-Vif and CFP-APO are expected to show reduced CFP fluorescence, but that the addition of a small molecule (16C) will cause a recovery of CFP fluorescence.
Figure 16B:
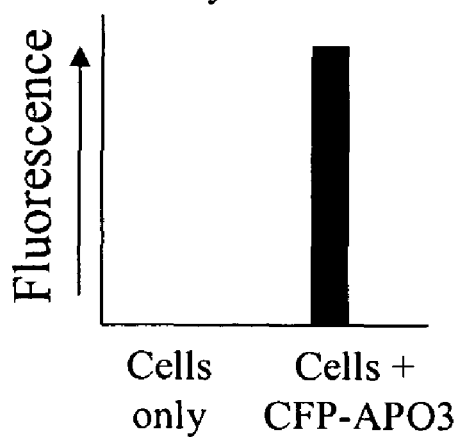
Figure 16C:
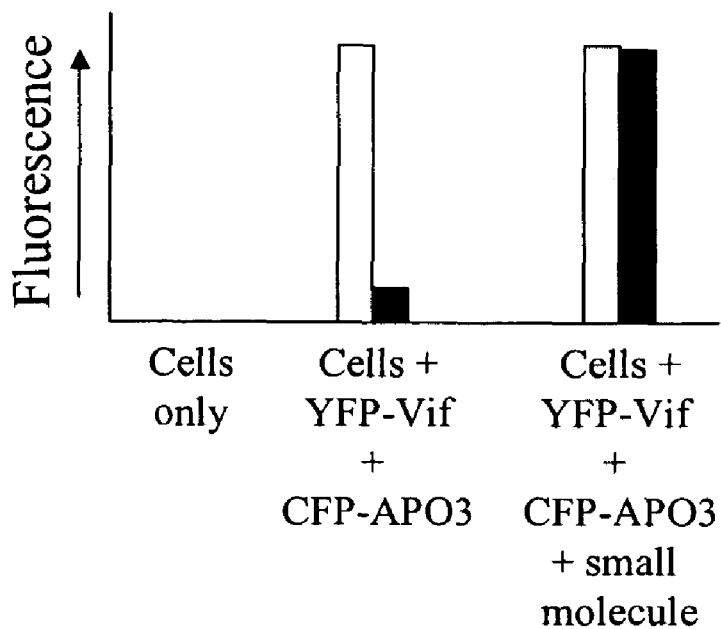

The compounds in a small molecule library were screened for the ability to affect Vif-mediated reduction in APOBEC3G protein levels. The protocol is illustrated in FIG. 14. Briefly, $1 \times 10^6$ 293T cells in each well of a 6 well plate were transfected with an 8:1 molar ratio of YFP-Vif and CFP-APOBEC3G encoding plasmids using Lipofectamine 2000™ transfection reagent. The cells were cultured for 12-16 hours, then 1 ml of trypsin was added to the cells to harvest them. The cells were resuspended in 5 ml DMEM 10% FCS without penicillin/streptomycin. The cells were then seeded into media containing the small molecules of the library in the wells of a 96 well plate, with a final concentration of 1% DMSO. After culture for 24 hours, the media is removed and M-PER/with 1% SDS lysis buffer is added to all of the wells. Fluorescence emission was read using a plate reader (Tecan, Maennedorf, Switzerland) as follows: CFP emission (475 nM); YFP emission (525 nM). Cells transfected with CFP-APOBEC3G alone (0.5 µg); YFP-Vif alone (3.5 µg); or empty pGEM (4.0 µg) were used as controls. FIGS. 15A-C are illustrations of a high-throughput screening method. FIG. 15A illustrates 293T Cells expressing only YFP-Vif. FIG. 15B illustrates 293T Cells expressing the target protein, APOBEC3G. FIG. 15C illustrates 293T cells expressing YFP-Vif, CFP-ABOBEC3G or both are cultured in a 96 well plate. After treating each well of cells with different small molecules ⊙, a fluorimeter can be used to screen the 96-well plate for cells emitting increased CFP fluorescence. Exemplary bar graphs showing fluorescence signals are shown in FIGS. 16A-C. For example, referring to FIG. 16C, cells containing both YFP-Vif and CFP-APO are expected to show reduced CFP fluorescence, but the addition of a small molecule can lead to the recovery of CFP fluorescence.

Figure 17:
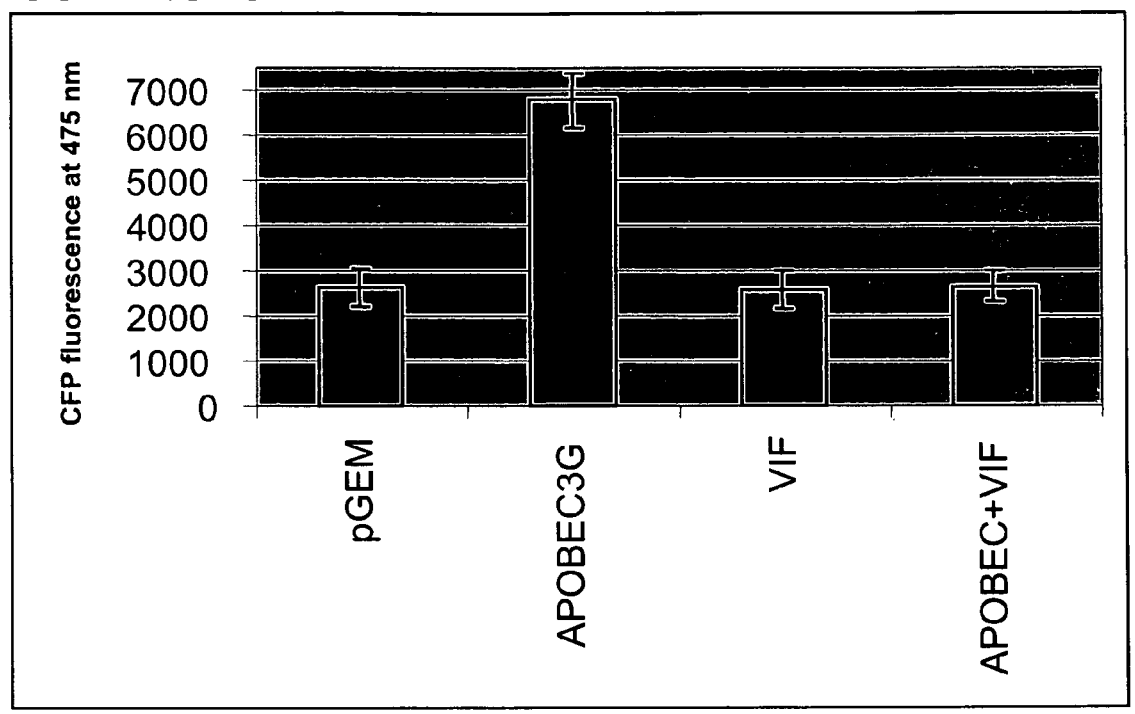
FIG. 17 is a bar graph showing CFP fluorescence in a CFP-APOBEC3G/YFP-Vif bioassay in a 96 well plate. Again, cells containing both YFP-Vif and CFP-APO show reduced CFP fluorescence.

The results are shown in FIG. 17, which represents the CFP fluorescence measured in well containing cells transfected with pGEM, CFP-APOBEC3G, YFP-Vif, or CFP-APOBEC3G and YFP-Vif. As expected, expression of pGEM or Vif-YFP resulted in negligible fluorescent emission at 475 nm. Expression of CFP-APOBEC3G resulted in significant fluorescence at 475 nm, and this fluorescence was substantially reduced by the co-expression of YFP-Vif.

Using this system, a combinatorial library a diverse library of 30,000 small molecules was purchased form Chembridge was screened for Vif-inhibitory activity. Numerous compounds were identified that demonstrated the ability to rescue APOBEC3G expression in the presence of Vif; these compounds are illustrated in FIGS. 1-8.

Example 7

Synthesis of Vif Inhibitor (1) shown in FIG. 10A

Method A:

Synthesis of 2-(4-Nitrophenylthio)-N-(2-methoxyphenyl)benzamide (1)

Vif inhibitor 1 was synthesized using the procedure outlined in Scheme 9. The key step in this reaction scheme is the copper catalyzed coupling reaction of 2-iodo-N-(2-methoxyphenyl)benzamide 3 with 4-nitrothiophenol 4 by microwave irradiation. The intermediate compound 3 was obtained in excellent yield by the reaction of 2-methoxyaniline 5 with 2-iodobezoyl chloride 2.

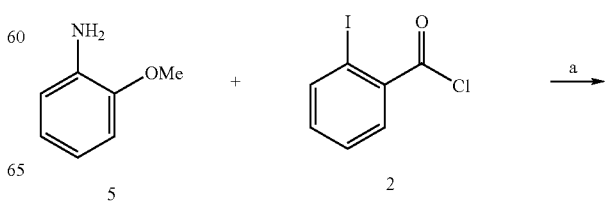

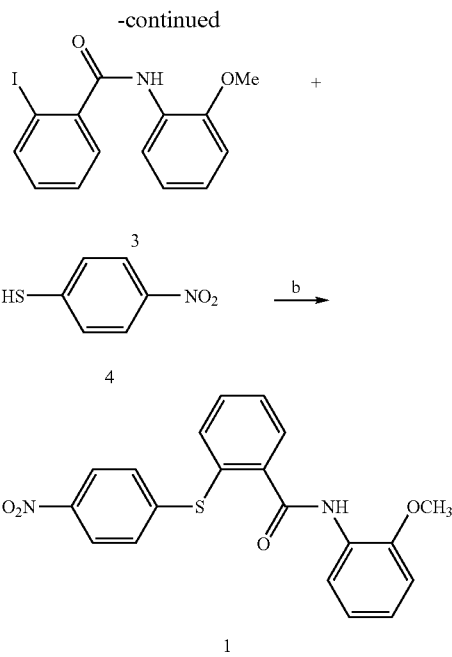

Scheme 9: (a) Et₃N, CH₂Cl₂, 0° C. to r. t. overnight, 98%; (b) K₂CO₃, Cu(I)I (cat.), HOCH₂CH₂OH, 2-propanol, microwave-150 W, 80° C., 30 min (2×), 63%.

2-Iodo-N-(2-methoxyphenyl)benzamide 3

To a solution of 2-methoxyaniline 5 (2.46 g, 20 mmol) in dry CH₂Cl₂ (50 mL) was added Et₃N (6.14 mL, 44 mmols) at 0° C. and under dry N₂ atmosphere. A solution 2-iodobenzoyl chloride 2 (5.33 g, 20 mmol) in dry CH₂Cl₂ (25 mL) was slowly added to the reaction mixture keeping the temperature at 0° C. After 15 min the reaction mixture was allowed to warm to room temperature and stirred overnight. Reaction mixture was diluted with CH₂Cl₂ (100 mL), washed with H₂O (40 mL) and saturated aqueous NaCl solution (40 mL), dried (Na₂SO₄) and evaporated to yield a light pink solid. Recrystallization from ethyl acetate-hexanes (1:3) provided 3 as white needles (5.7 g). The filtrate was concentrated and the residue was purified by flash chromatography on silica, eluting with 15% ethyl acetate (EtOAc) in hexanes, to provide additional pure product (1.25 g). Total yield: 6.95 g, 98%; ¹H NMR (400 MHz, CDCl₃) δ 8.54 (dd, J=8.0, 2.0 Hz, 1H), 8.10 (br s, 1H), 7.92 (dd, J=8.0, 1.2 Hz, 1H), 7.52 (dd, J=7.6, 1.2 Hz, 1H), 7.43 (ddd, J=8.8, 7.6, 1.2 Hz, 1H), 7.17-7.09 (m, 2H), 7.03 (t, J=8.0 Hz, 1H), 6.92 (d, J=8.0 Hz, 1H), 3.87 (s, 3H); ¹³C NMR (100 MHz, CDCl₃) δ 167.10, 148.29, 142.58, 140.30, 131.49, 128.52, 128.43, 127.58, 124.45, 121.33, 120.12, 110.25, 92.70, 55.92; MS (ESI): m/z 376.20 (M+Na)⁺.

2-(4-Nitrophenylthio)-N-(2-methoxyphenyl)benzamide (1)

2-Iodo-N-(2-methoxyphenyl)benzamide 3 (0.355 g, 1.0 mmol), Cu(I) iodide (20 mg, 0.1 mmol), K₂CO₃ (0.276 g, 2.0 mmol), and 4-nitrothiophenol (0.155 g, 1 mmol) were added to a 10 mL reaction vessel with Teflon-lined septum. The tube was evacuated and backfilled with dry N₂ (3 cycles). Ethylene glycol (0.1 mL, 2.0 mmol) and 2-propanol (1 mL) were added by syringe at room temperature. The reaction vessel was heated in a microwave reactor (CEM, Explorer) at 80° C. and 150 W power for 30 min (2×). The reaction mixture was then allowed to reach room temperature. Ethyl acetate (approx. 10 mL) was added; the reaction mixture was filtered and concentrated. The crude product was purified by flash column chromatography on silica, eluting with 20% EtOAc in hexanes. This procedure provided 2-(4-nitrophenylthio)-N-(2-methoxyphenyl)benzamide 1 as pale yellow crystalline solid (0.24 g, 63%); ¹H NMR (400 MHz, CDCl₃) δ 8.40 (d, J=8.0 Hz, 1H), 8.39 (s, 1H, overlapping signal), 8.05 (ddd, J=9.2, 2.4, 1.6 Hz, 2H), 7.77 (dd, J=6.4, 2.4 Hz, 1H), 7.56-7.49 (m, 3H), 7.29-7.25 (m, 2H), 7.06 (ddd, J=9.2, 7.6, 1.6 Hz, 1H), 6.95 (dt, J=8.8, 0.8, 1.2 Hz, 1H), 6.85 (dd, J=8.0, 0.8 Hz, 1H), 3.78 (s, 3H); ¹³C NMR (100 MHz, CDCl₃) δ 165.44, 148.22, 146.87, 146.15, 140.63, 135.76, 131.66, 130.09, 129.87, 129.49, 128.79 (2C), 127.54, 124.54, 124.35 (2C), 121.37, 120.05, 110.19, 55.88; MS (ESI): m/z 402.99 (M+Na)⁺.

Method B:

Synthesis of 2-(4-Nitrophenylthio)-N-(2-methoxyphenyl)benzamide (1)

Vif inhibitor 1 and a Vif inhibitor 1-analog was synthesized according procedure outlined in Scheme 10. The key step in the reaction scheme is the copper catalyzed coupling reaction of substituted iodobenzenes 6 with methyl thiosalicylate 7 under microwave irradiations. The resulting esters 8 were hydrolyzed to obtain the acids 9 in excellent yields. Treatment of the acids 9 with oxalyl chloride and the reaction of the resulting acid chlorides with o-anisidine 11 provided 2-(4-nitrophenylthio)-N-(2-methoxyphenyl)benzamide 1 and 2-(2-chloro-4-nitrophenylthio)-N-(2-methoxyphenyl)benzamide 12b. Reaction of the acid chlorides 9 with various other amines could provide analogs of Vif inhibitor 1.

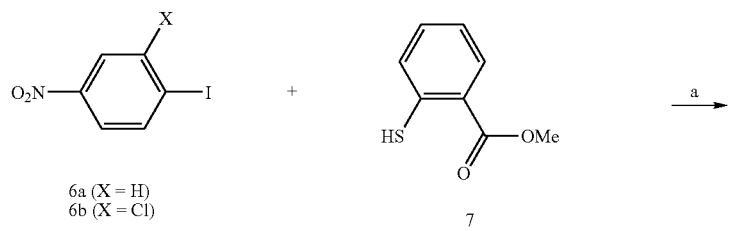

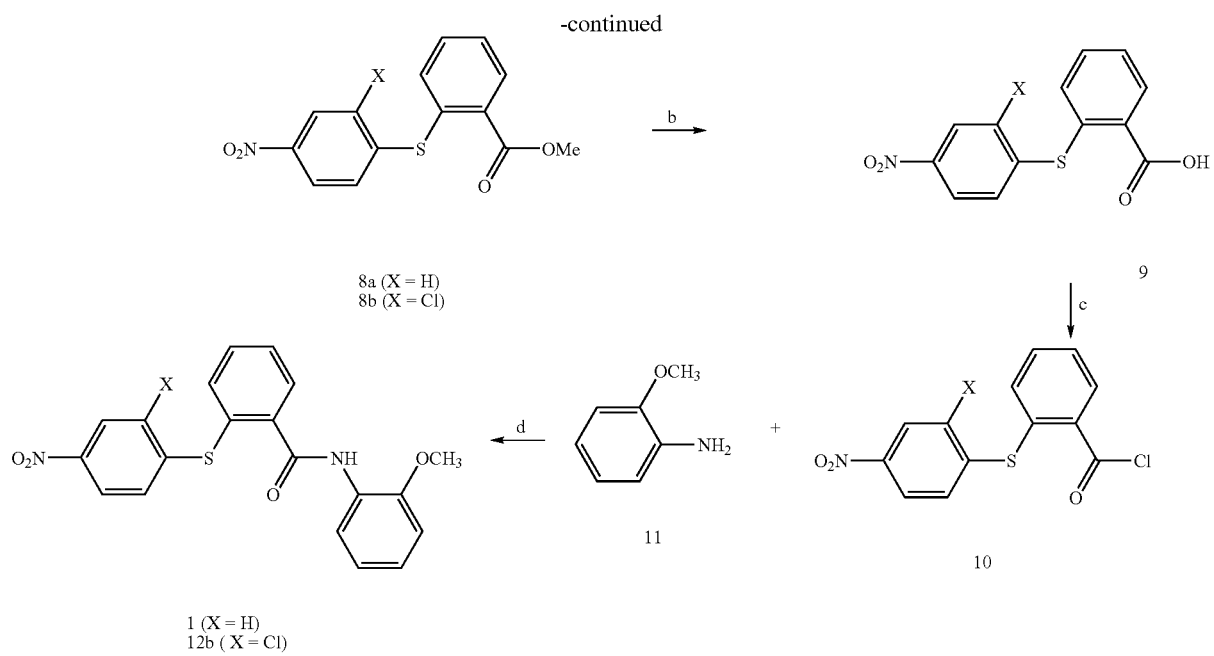

Scheme 10: (a) K$_2$CO$_3$, Cu(I)I (cat.), 1,2-DME, microwave (150 Wt power), 80° C., 30 min (2×); (b) Ba(OH)$_2$.8H$_2$O, MeOH, 80° C., 2 h; (c) (OCOCl)$_2$, CH$_2$Cl$_2$, r. t, 4 h; (d) Et$_3$N, CH$_2$Cl$_2$, 0° C. to r. t. overnight.

General Procedure for the Coupling Reaction

Substituted iodobenzene 6 (1.0 mmol), Cu(I) iodide (20 mg, 0.1 mmol), and K$_2$CO$_3$ (0.276 g, 2.0 mmol) were added to a 10 mL reaction vessel with Teflon-lined septum. The tube was evacuated and backfilled with dry N$_2$ (3 cycles). 1,2-Dimethoxyetane (1 mL) was added by syringe at room temperature followed by methyl thiosalicylate 7 (1 mmol). The reaction vessel was heated in a microwave reactor (CEM, Explorer) at 80° C. and 150 Wt power for 30 min (2×). The reaction mixture was then allowed to reach room temperature. Ethyl acetate (approx. 10 mL) was added; the reaction mixture was filtered and concentrated. The crude product was purified by flash column chromatography on silica, eluting with 15% EtOAc in hexanes.

Methyl 2-(4-nitrophenylthio)benzoate 8a

Above general procedure provided methyl 2-(4-nitrophenylthio)benzoate 8a as pale yellow crystalline solid in 75% yield; $^1$H NMR (400 MHz, CDCl$_3$) δ 8.15 (m, 2H), 7.95 (dd, J=7.6, 1.6 Hz, 1H), 7.47 (m, 2H), 7.39 (ddd, J=8.8, 7.6, 1.6 Hz, 1H), 7.32 (ddd, J=8.8, 7.6, 1.6 Hz, 1H), 7.17 (dd, J=8.0, 1.6 Hz, 1H), 3.89 (s, 3H); $^{13}$C NMR (100 MHz, CDCl$_3$) δ 166.82, 146.93, 144.95, 136.71, 132.71, 131.88 (2 C), 131.72, 131.25, 131.07, 127.30, 124.42 (2 C), 52.56; MS (ESI): m/z 312.50 (M+Na)$^+$.

Methyl 2-(2-chloro-4-nitrophenylthio)benzoate 8b

Above general procedure provided methyl 2-(2-chloro-4-nitrophenylthio)benzoate 8b as yellow crystalline solid in 70% yield; $^1$H NMR (400 MHz, CDCl$_3$) δ 8.26 (d, J=2.4 Hz, 1H), 7.99-7.95 (m, 2H), 7.50-7.43 (m, 2H), 7.27 (dd, J=7.6, 1.6 Hz, 1H), 7.16 (d, J=8.4 Hz, 1H), 3.87 (s, 3H); $^{13}$C NMR (100 MHz, CDCl$_3$) δ 166.81, 146.72, 145.46, 134.60, 133.83, 133.36, 133.17, 133.02, 131.59, 131.40, 128.80, 125.04, 121.22, 52.76; MS (ESI): m/z 346.50 (M+Na)$^+$.

General Procedure for the Hydrolysis of Ester 8

A solution of Ester 8 (1 mmol) in MeOH (10 ml) was treated with Ba(OH)$_2$.8H$_2$O (1.5 mmol) and heated to 80° C. for 2 hours. Reaction mixture was allowed to cool to room temperature and the solvent was removed under reduced pressure. The residue was treated with 1M HCl solution in Et$_2$O (15 mL), diluted with Et$_2$O (20 mL), dried (Na$_2$SO$_4$) and filtered. The filtrate was concentrated to provide the acid 9 as yellow solid. This acid was used in the next step without further purification.

General Procedure for the Amide Coupling

To a solution of benzoic acid 9 (1 mmol) in dry CH$_2$Cl$_2$ (10 mL) was added oxalyl chloride (5 mmol) followed by a drop of dimethylformamide. The mixture was stirred at room temperature for 4 hours. Solvents were removed under reduced pressure and the residue was dried under high vacuum to give acid chloride 10 as yellow solid. A solution of amine (1 mmol) in dry CH$_2$Cl$_2$ (5 mL) under nitrogen atmosphere was cooled to 0° C. and Et$_3$N (2.2 mmol) was added followed by the addition of the above acid chloride solution in CH$_2$Cl$_2$ (5 mL). The resulting mixture was allowed to warm to room temperature and stirred overnight. It was diluted with CH$_2$Cl$_2$ (20 mL), washed with H$_2$O and saturated aqueous NaCl solution, dried (Na$_2$SO$_4$) and evaporated to yield a yellow solid. The product was purified by flash chromatography on silica.

2-(4-Nitrophenylthio)-N-(2-methoxyphenyl)benzamide 1b

Above general procedure provided 2-(4-nitrophenylthio)-N-(2-methoxyphenyl)benzamide 12 as pale yellow crystalline solid in 90% yield. Analytical data is identical to that of 1 made according to Method A.

2-(2-Chloro-4-nitrophenylthio)-N-(2-methoxyphenyl)benzamide 12b

Above general procedure provided 2-(2-chloro-4-nitrophenylthio)-N-(2-methoxyphenyl)benzamide 12b as yellow solid in 90% yield; $^1$H NMR (400 MHz, CDCl$_3$) δ 8.42 (br. s, 1H), 8.36 (dd, J=8.0, 1.6 Hz, 1H), 8.15 (d, J=2.4 Hz, 1H), 7.90 (dd, J=8.8, 2.4 Hz, 1H), 7.84 (dd, J=7.6, 1.2 Hz, 1H), 7.62-7.52 (m, 3H), 7.05 (ddd, J=9.2, 8.0, 1.6 Hz, 1H), 6.94 (m, 2H), 6.85 (dd, J=8.0, 0.8 Hz, 1H), 3.79 (s, 3H); $^{13}$C NMR (100 MHz, CDCl$_3$) δ 165.04, 148.21, 146.62, 145.85, 141.54, 136.70, 132.02, 131.88, 130.69, 129.79, 128.50, 127.87, 127.37, 124.65, 124.51, 122.14, 121.20, 120.03, 110.12, 55.80; MS (ESI): m/z 437.61 (M+Na)$^+$.

Example 8

Vif-inhibitor 1 Exhibits a Dose Dependent Decrease in RT Activity

To evaluate the efficacy of Vif inhibitor 1 on RT activity, a dose-response experiment was conducted in infected H9 cells.

Briefly, H9 cells plated at 2×10$^5$ per well in a 24 well plate were treated overnight with DMSO, plus 0, 1, 5, 10, 25 or 50 μM Vif inhibitor 1 (all at 0.5% DMSO) then infected with HIV-1 (X4-tropic HIV-1 variant (HIV-1LAI)) at 2×10$^5$ cpm RT per well. All cells were maintained in the presence of DMSO or Vif inhibitor 1 for 14-21 days and viral replication monitored by measurement of reverse transcriptase activity in culture supernatants every second day. Calculation of % relative infectivity was determined on day 7, which was previously determined to be the peak of viral infectivity. Range correction involved fitting cpm data to a 2 parameter equation where the lower limit is 0, i.e. background correction, and the upper data limit is 100, i.e. the data is range corrected. Grafit software was used for the curve fit and calculation of the I.C.50 value.

Figure 20:
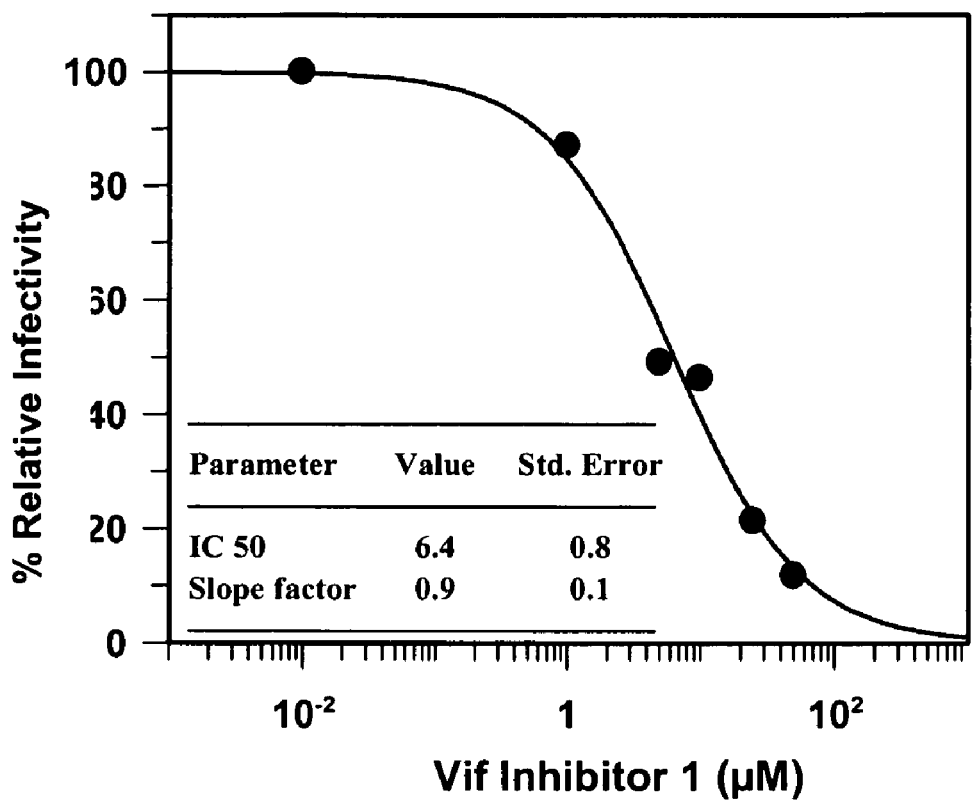
FIG. 20 is a dose-response curve for Vif Inhibitor 1 showing a dose-dependent decrease in infectivity.

The results, shown in FIG. 20, demonstrate that Vif inhibitor 1 inhibits RT activity in a dose dependent manner, with an I.C.50 of about 6.4 μM.

Example 9

Vif-inhibitor 1 decreases Vif Expression and Increases APOBEC3G Expression

To determine the effect of Vif inhibitor 1 on expression of Vif and APOBC3G, 293T cells were transfected with pNL-Luc-E-R-, pVSV-G, and 15 fmoles APOBEC3G-HA. 4 hours post-transfection, the cells were treated with 3.125, 6.25, 12.5, 25, 50 μM Vif inhibitor 1 or DMSO equivalent as a control. Twenty-four hours post-drug addition, 293T total cell lysates (15 ug) were prepared, and protein lysates examined for APOBEC3G, Vif and, cyclin T1. The results, shown in FIG. 21A, indicate that Vif inhibitor 1 decreases Vif expression and increases APOBEC3G expression.

As shown in FIG. 21B, similar results were obtained in 293T cells transfected with pNL-Luc-E-R-, pVSV-G, and increasing concentrations of APOBEC3G-HA (3.75, 7.5 or 15 fmoles) and treated with either DMSO (−) or 50 μM Vif inhibitor 1 (+).

Figure 21A:
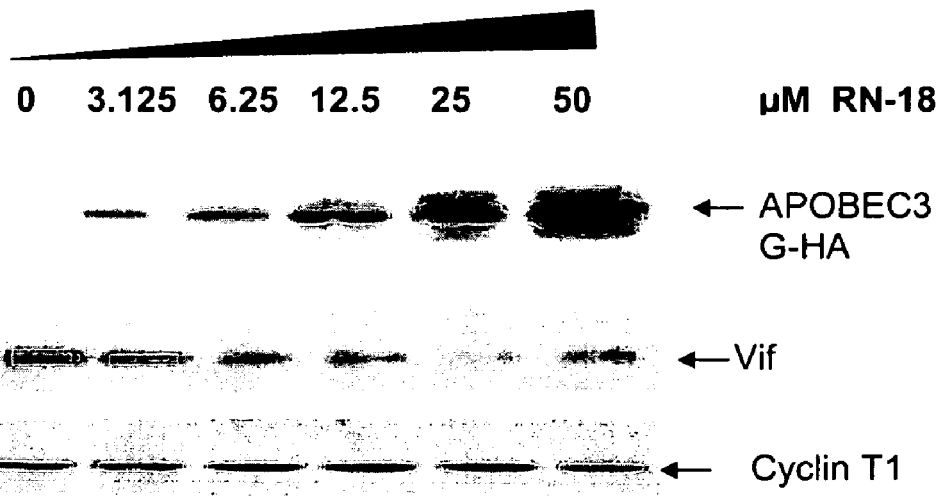
FIG. 21A is a set of Western blots of APOBEC3G, Vif, and cyclin T1 in lysates from 293T cells transfected with pNL-Luc-E-R-, pVSV-G, and 15 fmoles APOBEC3G-HA treated with 3.125, 6.25, 12.5, 25, 50 μM Vif inhibitor 1 or DMSO equivalent (0).

Infectivity was determined by infecting 293T cells for 48 hours with 1 ng virus produced from the producer cells in the experiments shown in FIG. 21A. The infectivity of the sample of virus produced without APOBEC3G was normalized to 100%, and data was representative of three independent experiments. The results are shown in FIG. 21C, and demonstrate that increasing concentrations of Vif inhibitor 1 decrease infectivity in a dose-dependent manner. Infectivity was also determined in the same manner for virus from the producer cells in the experiment shown in FIG. 21B. The results, shown in FIG. 21D, demonstrate that Vif inhibitor 1 decreases Vif expression and increases APOBEC3G expression in 293T cells.

Example 10

Effect of Vif inhibitor 1 on APOBEC3G and APOBEC3F

To evaluate the effect of Vif inhibitor 1 on levels of APOBEC3G and APOBEC3F proteins, a dose-response experiment was performed. pNL4-3-LucE-R- was co-expressed with 3.75, 7.5, 15, or 30 fmoles APOBEC3G-HA (or APOBEC3F-HA) in the absence (DMSO) or presence (5 uM) of Vif inhibitor 1. The pNL4-3-LucE-R- ΔVif with the same amounts of APOBEC3G or F in the presence of DMSO were used as controls. APOBEC3G or APOBEC3F expression was confirmed by Western blot using an α HA anti body, with cyclin T1 used as the internal control.

The results, shown in FIGS. 22A-B, indicate that Vif inhibitor 1 increases APOBEC3G (22A) and APOBEC3F (22B) in a dose-dependent manner. This is particularly interesting, as it indicates that APOBEC3F is also a target of Vif.

Example 11

Effect of Vif inhibitor 1 on Vif Protein Levels in H9 Cells

To evaluate the effect of Vif inhibitor 1 on levels of Vif protein, H9 cells were infected with pNL4-3Luc-E-R- using a spinoculation procedure with the virus equivalent of 1 μg pNL4-3 Luc-E-R- or Δ Vif pNL4-3 Luc-E-R- (as measured using p24 ELISA). Immediately following infection, the H9 cells were washed and incubated in complete RPMI medium with 10% FCS containing DMSO (0.5%) or 50 μM Vif inhibitor 1 (also 0.5% DMSO) for 48 hours. H9 total cell lysates were then prepared, and 20 μg of lysate examined for the presence of cyclin T1, endogenous APOBEC3G, p24, and Vif, the latter two indicative of virus infection.

Figure 23A:
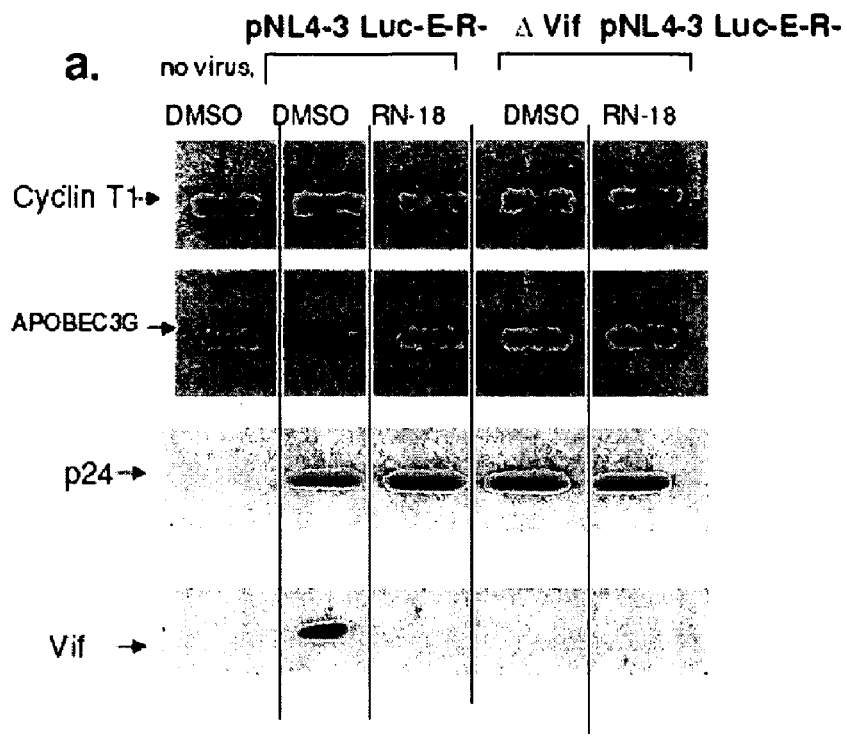
FIGS. 23A-B are Western blots showing levels of cyclin T1, endogenous APOBEC3G, p24, and Vif, the latter two being indicative of virus infection, in H9 cells that were either not infected (mock) or infected with pNL4-3 Luc-E-R- or Δ Vif pNL43Luc-E-R-, then treated with DMSO or 50 μM Vif inhibitor 1 (23A), and in cells infected with pNL4-3 Luc-E-R- then treated with DMSO, 12.5, 25, or 50 μM Vif inhibitor 1 (23B).
Figure 23B:
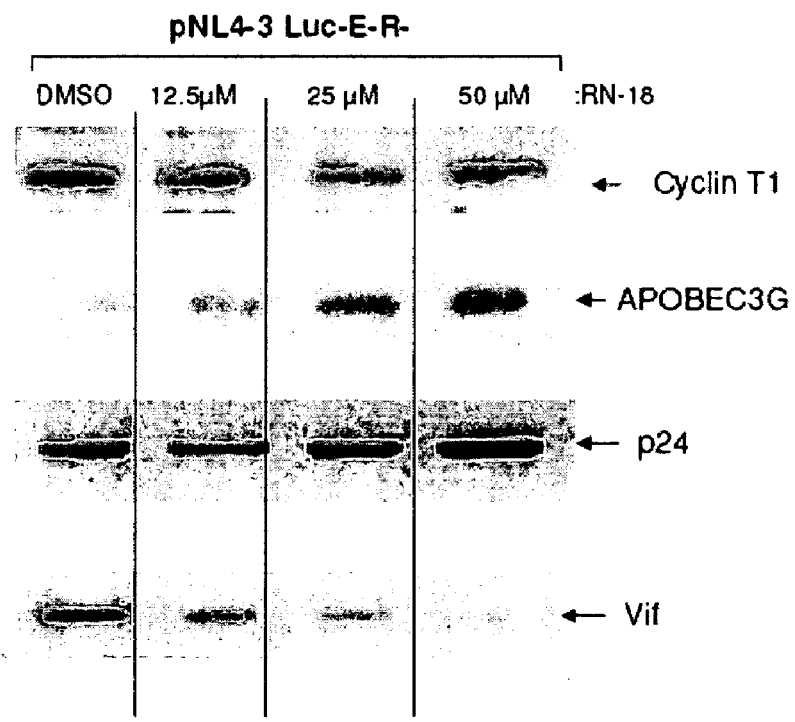

FIG. 23A shows the results in H9 cells that were not infected (mock) or infected with pNL4-3 Luc-E-R- or Δ Vif pNL43Luc-E-R-, then treated with DMSO or 50 μM Vif inhibitor 1. FIG. 23B shows the results in H9 cells that were infected with pNL4-3 Luc-E-R-, then treated with DMSO, 12.5, 25, or 50 μM Vif inhibitor 1.

These results demonstrate that Vif inhibitor 1 significantly reduces levels of Vif protein in H9 cells infected with pNL4-3Luc-E-R-.

Example 12

Effect of Vif inhibitor 1 on Vif Protein Levels in H9 Cells versus MT4 Cells To determine whether there was a difference in the effect of Vif inhibitor 1 on Vif protein levels in permissive versus non-permissive cells, H9 and MT4 cells were infected using a spinoculation procedure with the virus equivalent of 1 μg pNL4-3 Luc-E-R- or Δ Vif pNL4-3 Luc-E-R- (as measured using p24 ELISA). Immediately following infection, H9 or MT4 cells were washed and incubated in complete RPMI medium with 10% FCS containing DMSO (0.5%) or 50 μM Vif inhibitor 1 (also 0.5% DMSO) for 48 hours. H9 or MT4 total cell lysates were then prepared, and 20 μg of lysate was examined for the presence of cyclin T1, endogenous APOBEC3G, p24, and Vif, the latter two being indicative of virus infection.

Figure 24A:
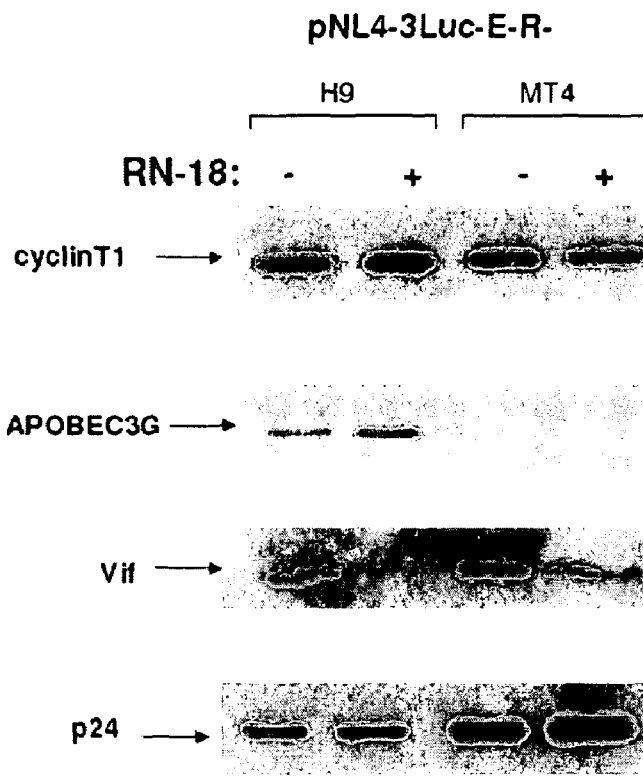
FIGS. 24A-B are Western blots showing levels of cyclin T1, endogenous APOBEC3G, p24, and Vif, the latter two being indicative of virus infection, in H9 and MT4 cells infected using a spinoculation procedure with the virus equivalent of 1 ug pNL4-3 Luc-E-R-(24A) or Δ Vif pNL4-3 Luc-E-R-(24B).
Figure 24B:
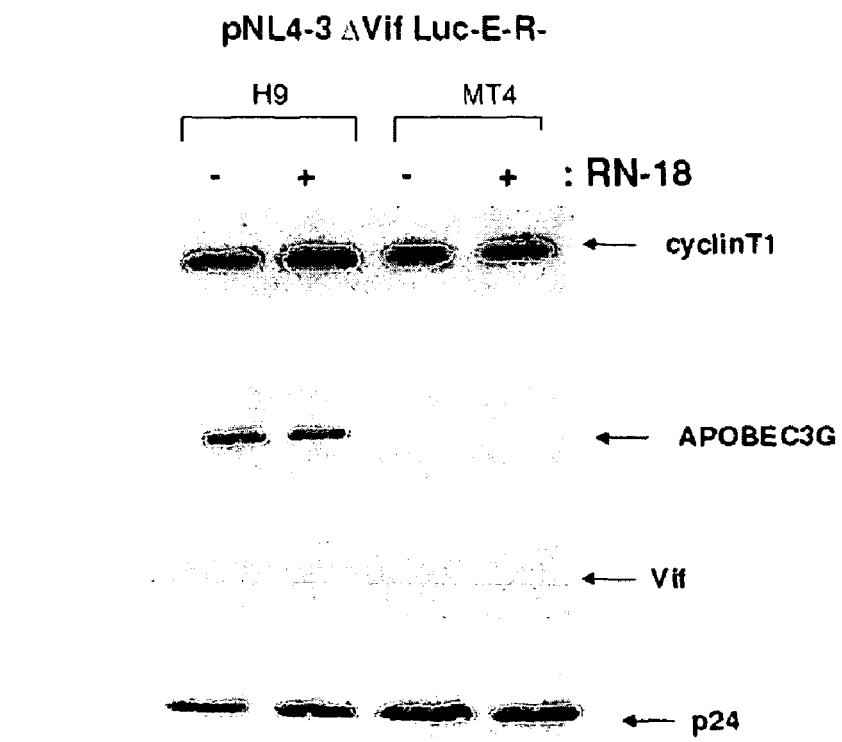

As shown in FIGS. 24A-B, Vif inhibitor 1 significantly reduces levels of Vif protein in non-permissive H9 cells compared to permissive MT4 cells infected with pNL4-3Luc-E-R-.

Example 13

The effect of Vif inhibitor 1 on the Half-Life of Vif Protein

The effect of Vif inhibitor 1 on the half-lives of Vif and APOBEC3G proteins was determined.

Half-lives were calculated for pulse-chase labeling and immunoprecipitation of Vif or APOBEC3G protein, for example, as described in Chu, C, and Rana, T. M. (2006) Translation Repression in Human Cells by Micro RNA-induced Gene Silencing Requires RCK/p54. *PLos Biology*, 4, e210, DOI: 10.1371/journal.pbio.0040210. pNL4-3 (Vif) was used at 50 fmol, and APOBEC3G at 15 fmol. For experiments examining APOBEC3G half life, pNLA-4-3 ΔVif(luc) was substituted for pNL4-3 (also at 50 fmol). DMSO and Vif inhibitor 1 were used at 0.5% final concentration.

The results, shown in Table 1, indicate that Vif inhibitor 1 reduces the half-life of Vif in the presence of APOBEC3G.

TABLE 1

Effect of Vif inhibitor 1 on Half-Life of Vif and APOBEC3G

|  | Minutes |
|---|---|
| Vif half-life | |
| DMSO: | 46.2 |
| 50 μM Vif inhibitor 1: | 45.7 |

TABLE 1-continued

Effect of Vif inhibitor 1 on Half-Life of Vif and APOBEC3G

|  | Minutes |
|---|---|
| DMSO with APOBEC3G: | 57.6 |
| 50 μM Vif inhibitor 1 with APOBEC3G: | 31.0 |
| APOBEC3G half-life | |
| DMSO: | 29.5 |
| DMSO with Vif: | 17.8 |
| 50 μM Vif inhibitor 1 with Vif: | 17.8 |

Example 14

Effect of Vif inhibitor 1 on pNLA1-YFP 293T cells transfected with 50 fmoles pNLA1-YFP or pNLA1-YFP with 15 fmoles pAPOBEC3G-HA were treated 4 HRS post-transfection with 3.125, 6.25, 12.5, 25, 50 μM Vif inhibitor 1 or DMSO equivalent (0). Twenty-four hours post-drug addition, 293T total cell lysates were prepared and normalized to equal protein amounts prior to being monitored, in triplicate, for YFP fluorescence. Curve fits for full dose responses of Vif inhibitor 1 are shown, and calculation of "% Vif activity" for concentration of compound Vif inhibitor 1 was determined using Grafit software.

Figure 25:
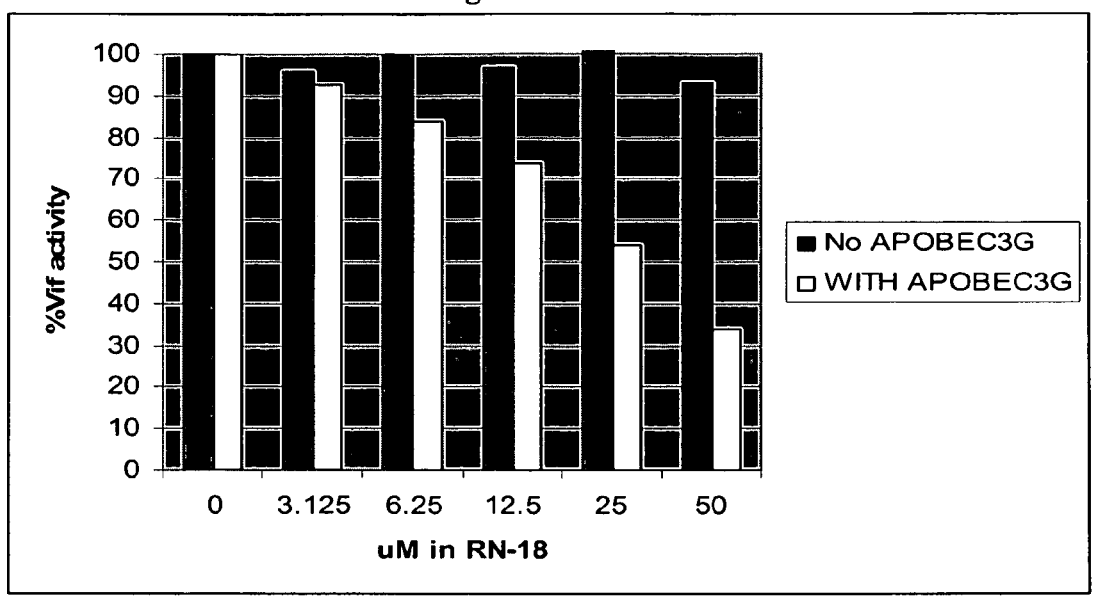
FIG. 25 is a bar graph showing that Vif inhibitor 1 demonstrates a dose-dependent decrease in pNLA1-YFP only in the presence of APOBEC3G.

The results, shown in FIG. 25, demonstrate that Vif inhibitor 1 demonstrates a dose-dependent decrease in pNLA1-YFP only in the presence of APOBEC3G.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a Human Immunodeficiency Virus (HIV) infection in a subject, the method comprising administering to the subject a therapeutically effective amount of a pharmaceutical composition comprising a therapeutically effective amount of a compound having the following formula:

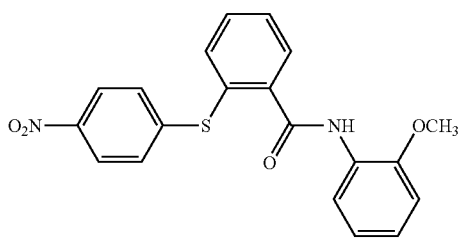

or pharmaceutically acceptable salt thereof.

2. The method of claim 1, further comprising identifying in the subject HIV-infected cells comprising both Virion Infectivity Factor (Vif) and APOBEC3G protein; and then administering the pharmaceutical composition to the subject.

3. The method of claim 1, further comprising identifying in the subject HIV-infected cells comprising at least one compound selected from the group consisting of Virion Infectivity Factor (Vif), APOBEC3G protein and APBEC3F protein; and then administering the pharmaceutical composition to the subject.

4. A method of inhibiting Human Immunodeficiency Virus (HIV) replication in a HIV-infected cell population of HIV-infected human lymphocyte cells, the method comprising contacting the HIV-infected cell population with a compound having the formula:

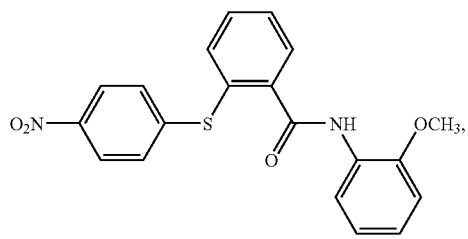

or pharmaceutically acceptable salt thereof.

5. The method of claim 4, wherein the HIV-infected cell population comprises non-permissive cells, and the method further comprises identifying the cell population comprising the HIV-infected non-permissive cells.

6. The method of claim 4, wherein the HIV-infected cell population includes cells comprising Virion Infectivity Factor (Vif), and the method further comprises identifying the cell population comprising the HIV-infected cells comprising Virion Infectivity Factor (Vif).

7. The method of claim 4, wherein the HIV-infected cell population includes cells comprising APOBEC3G protein.

8. The method of claim 4, wherein the HIV-infected cell population includes cells comprising both Virion Infectivity Factor (Vif) and APOBEC3G protein.

9. The method of claim 4, wherein the cell population is selected from one or more cells in the group consisting of H9 cells, MT4 cells, and HUT78 cells.

10. The method of claim 8, wherein the cell population comprises H9 cells.

11. A method of reducing the infectivity of a Human Immunodeficiency Virus (HIV)-infected cell population, the method comprising contacting the HIV-infected cell population with a compound having the formula:

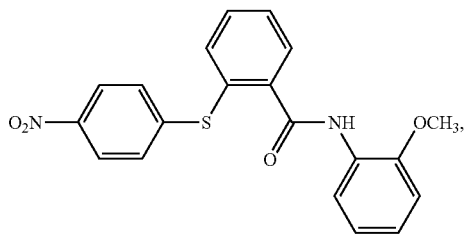

or pharmaceutically acceptable salt thereof.

12. The method of claim 11, wherein the cell population comprises non-permissive cells.

13. The method of claim 11, wherein the cell population is a HIV-infected lymphocytic cell population where at least a portion of the cells in the cell population comprises Virion Infectivity Factor (Vif).

14. The method of claim 11, wherein the cells in the cell population comprise both Virion Infectivity Factor (Vif) and APOBEC3G protein.

15. A method for treating a Human Immunodeficiency Virus (HIV) infection in a subject, the method comprising administering to the subject a therapeutically effective amount of a pharmaceutical composition comprising a therapeutically effective amount of a compound having the following formula:

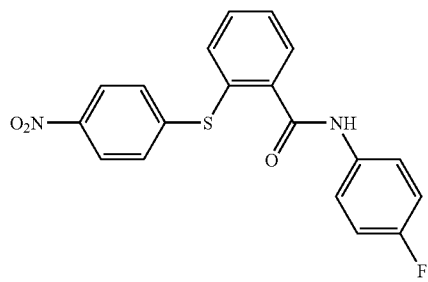

or pharmaceutically acceptable salt thereof.

16. The method of claim 15, further comprising identifying in the subject HIV-infected cells comprising both Virion Infectivity Factor (Vif) and APOBEC3G protein; and then administering the pharmaceutical composition to the subject.

17. The method of claim 15, further comprising identifying in the subject HIV-infected cells comprising at least one compound selected from the group consisting of Virion Infectivity Factor (Vif), APOBEC3G protein and APBEC3F protein; and then administering the pharmaceutical composition to the subject.

* * * * *